US012644104B2

(12) United States Patent
Borlinghaus et al.

(10) Patent No.: US 12,644,104 B2
(45) Date of Patent: Jun. 2, 2026

(54) DETECTION OF ENVIRONMENTAL INFLUENCES BY BIOLUMINESCENCE

(71) Applicant: Rheinisch-Westfälische Technische Hochschule (RWTH) Aachen, Aachen (DE)

(72) Inventors: Jan Borlinghaus, Aachen (DE); Martin Gruhlke, Eschweiler (DE); Jana Foerster, Aachen (DE); Alan Slusarenko, Hergenrath (BE); Michael Eberhard Ries, Langenfeld (DE)

(73) Assignee: Rheinisch-Westfälische Technische Hochschule (RWTH) Aachen, Aachen (DE)

( * ) Notice: Subject to any disclaimer, the term of this patent is extended or adjusted under 35 U.S.C. 154(b) by 418 days.

(21) Appl. No.: 18/028,315

(22) PCT Filed: Nov. 3, 2021

(86) PCT No.: PCT/EP2021/080449
§ 371 (c)(1),
(2) Date: Mar. 24, 2023

(87) PCT Pub. No.: WO2022/096479
PCT Pub. Date: May 12, 2022

(65) Prior Publication Data
US 2023/0374472 A1    Nov. 23, 2023

(30) Foreign Application Priority Data
Nov. 4, 2020    (DE) ..................... 10 2020 129 009.8

(51) Int. Cl.
*C12N 9/02* (2006.01)
*C12N 1/16* (2006.01)
*C12N 9/06* (2006.01)

*C12N 15/52* (2006.01)
*C12Q 1/6897* (2018.01)

(52) U.S. Cl.
CPC ............. *C12N 9/0069* (2013.01); *C12N 1/16* (2013.01); *C12N 9/0028* (2013.01); *C12N 15/52* (2013.01); *C12Q 1/6897* (2013.01); *C12Y 105/01036* (2013.01); *C12Y 113/12007* (2013.01)

(58) Field of Classification Search
CPC ............................... C12N 9/0069; C12N 1/16
USPC .......................................................... 435/8
See application file for complete search history.

(56) References Cited

U.S. PATENT DOCUMENTS

2013/0074221 A1    3/2013    Krichevsky

OTHER PUBLICATIONS

Shi, Zhenyu et al. "Parallel In Vivo DNA Assembly by Recombination: Experimental Demonstration and Theoretical Approaches", Plos One, vol. 8, No. 2, Feb. 2, 2013, p. e56854.

(Continued)

*Primary Examiner* — Robert B Mondesi
(74) *Attorney, Agent, or Firm* — McDonald Hopkins LLC

(57) ABSTRACT

A nucleic acid comprising a continuous nucleotide sequence, containing: (i) a gene encoding LuxA, (ii) a gene encoding LuxB, (iii) a gene encoding LuxC, (iv) a gene encoding LuxD, (v) a gene encoding LuxE, wherein each of the genes is under the control of a promoter heterologous to the respective gene, and wherein all of the genes together with the promoter are contained in a single nucleotide sequence in a row. The vectors and host cells comprise the nucleic acid. Methods of producing a host cell and methods and uses for detecting an environmental effect and a kit therefor.

17 Claims, 6 Drawing Sheets

Specification includes a Sequence Listing.

(56) References Cited

OTHER PUBLICATIONS

Xu, Tingting et al. "A rapid and reagent-free bioassay for the detection of dioxin-like compounds and other aryl hydrocarbon receptor (AhR) agonists using autobioluminescent yeast", vol. 410, No. 4, Dec. 4, 2017, pp. 1247-1256.

Gupta, Rakesh K et al. "Expression of the Photorhabdus luminescens lux genes (luxA, B, C, D, and E) in *Saccharomyces cerevisiae*", FEMS Yeast Research, vol. 4, No. 3, Dec. 1, 2003, pp. 305-313.

International Search Report for PCT/EP2021/080449 dated Feb. 25, 2022.

Written Opinion for PCT/EP2021/080449 dated Feb. 25, 2022.

Ando, A. et al. "Cooperative function of the CHD5-like protein Mdm39p with a P-type ATPase Spf1p in the maintenance of ER homeostasis in *Saccharomyces cerevisiae*" Molecular Genetics and Genomics, 2005, 273(6), pp. 497-506.

Bhaumik, S. et al. "Optical imaging of Renilla luciferase reporter gene expression in living mice." Proceedings of the National Academy of Sciences of the United States of America, Jan. 8, 20023, vol. 99, No. 1, pp. 377-382.

Brachmann C. B., et al. Designer Deletion Strains derived from *Saccharomyces cerevisiae* S288C: A Useful set of Strains and Plasmids for PCR-mediated Gene Disruption and Other Applications. Yeast, Jun. 18, 1997, vol. 14(2), pp. 115-132.

Chien, C. T., et al. "The two-hybrid system: A method to identify and clone genes for proteins that interact with a protein of interest" Proceedings of the National Academy of Sciences, vol. 88(21), pp. 9578-9582.

Close, D. M. et al. "Reporter proteins in whole-cell optical bioreporter detection systems, biosensor integrations, and biosensing applications" Sensors, 2009, vol. 9(11), pp. 9147-9174.

Contag, C. H. et al. "Photonic detection of bacterial pathogens in living hosts" Molecular Microbiology, 1995, vol. 18 (4), pp. 593-603.

Contag, P. R. "Bioluminescent indicators in living mammals" Nature Medicine, 1998, vol. 4(2), pp. 245-247.

Dunlap, P. "Biochemistry and Genetics of Bacterial Bioluminescence" 2014, Bioluminescence: Fundamentals and Applications in Biotechnology—vol. 1, pp. 37-64.

Engebrecht, J. et al. "Bacterial bioluminescence: isolation and genetic analysis of functions from Vibrio fischeri" Mar. 1983, vol. 32, pp. 773-781.

Foran, David R. "Nucleotide sequence of the LuxA and LuxB genes of the bioluminescent marine bacterium Vibrio ischeri" 1988, vol. 16, No. 2, p. 777.

Gietz, R. Daniel et al. "Transformation of yeast by lithium acetate/single-stranded carrier DNA/polyethylene glycol method" Methods in Enzymology, 2002; vol. 350, pp. 87-96.

Gruhlke, Martin C.H. et al. "Yap1p, the central regulator of the *S. cerevisiae* oxidative stress response, is activated by allicin, a natural oxidant and defense substance of garlic" Free Radical Biology and Medicine, May 2017, vol. 108, pp. 793-802.

Pelletier J., et al. "Internal initiation of translation of eukaryotic mRNA directed by a sequence derived from poliovirus RNA" Nature, Jul. 28, 1988, vol. 334(6180), pp. 320-325.

Jansen, Gregor et al. "Drag&Drop cloning in yeast" Gene 2005, vol. 344, pp. 43-51.

Minskaia, Ekaterina et. al. "Optimisation of the foot-and-mouth disease virus 2A co-expression system for biomedical applications" BMC Biotechnology, 2013, vol. 3, No. 67, pp. 1-11.

Mumberg Dominik, et al. "Yeast vectors for the controlled expression of heterologous proteins in different genetic backgrounds" Gene, 1995, vol. 156(1), pp. 119-122.

DETECTION OF ENVIRONMENTAL INFLUENCES BY BIOLUMINESCENCE

CROSS-REFERENCE TO RELATED APPLICATIONS

This is a National Stage application of PCT international application PCT/EP2021/080449, filed on Nov. 3, 2021, which claims the priority of German Patent Application No. 10 2020 129 009.8 filed Nov. 4, 2020, both of which are incorporated herein by reference in their entirety.

SEQUENCE LISTING

The material in the XML text file, named EISEN-67933-Sequence-Listing.txt created Mar. 8, 2023, file size of 102, 400 bytes, is hereby incorporated by reference.

FIELD OF THE INVENTION

The present invention relates to a nucleic acid comprising a continuous nucleotide sequence, containing: (i) a gene encoding LuxA, (ii) a gene encoding LuxB, (iii) a gene encoding LuxC, (iv) a gene encoding LuxD, (v) a gene encoding LuxE, wherein each of the genes is under the control of a promoter heterologous to the respective gene, and wherein all of the genes together with the promoter are contained in a single nucleotide sequence in a row. The invention further relates to vectors and host cells comprising the nucleic acid. Also described are methods of producing a host cell according to the invention and methods and uses for detecting an environmental effect and a kit therefor.

BACKGROUND

Although bioluminescence has evolved in parallel several times, the basic light reaction is the same in all organisms. A luciferase catalyzes the reaction of luciferin with oxygen consumption to form a luciferase-bound peroxy-luciferin intermediate product, which releases its excess energy by emitting light. The use of luciferases such as *Renilla* luciferase from *Renilla reniformis*, Firefly luciferase from Photinus pyralis, or bacterial luciferases, e.g., from *Vibrio*, Photobacterium, or *Photorhabdus luminescens* in bioanaly-sis has been described previously (Bhaumik & Gambhir, 2002; Contag et al., 1995; Contag et al., 1998).

The bacterial luciferase is a heterodimer and is encoded by the luxA and luxB genes (Foran & Brown, 1988). The luxC, luxD, and luxE genes encode a transferase (LuxD) and a synthetase/reductase (LuxCE) that are necessary for the synthesis of the aldehyde substrate required in the light reaction. These genes are part of the bacterial lux operon (Close et al., 2009).

However, the different genetic organization of bacterial genes compared to eukaryotic genes makes direct gene transfer from bacteria to fungi or other eukaryotes difficult. Several approaches to express the bacterial system in yeast have been described in the state of the art (Gupta et al., 2003; Xu et al., 2018). For the expression of the bacterial lux system in eukaryotes, the prokaryotic operon structure was previously mimicked using specific gene-linking sequences. This was the only way to regulate all genes using only one promoter and one terminator. In both publications, the genes of the lux operon are arranged in a gene cassette one after the other, wherein the coding gene sequences are linked by IRES (internal ribosomal entry sites) or 2A sequences.

The biggest and broadest application potential of bioluminescence exists currently in the field of biosensors. By introducing a luciferase fused to a regulatory DNA sequence, which induces luciferase expression only in the presence of a specific stimulus, an inducible reporter system can be established. Such a system can be automated and used for high-throughput screening.

However, the disadvantages associated with IRES (decreasing expression of genes after each IRES sequence) or 2A sequences (retention of the 2A sequence C-terminally at the cleavage site and a proline N-terminally at the cleavage site) make the luciferase systems known from the prior art less efficient for this purpose. The task of the present invention was therefore to provide an improved luciferase system suitable for use as a biosensor.

SUMMARY OF THE INVENTION

The inventors could unexpectedly demonstrate that combining all the genes of the lux operon on a single nucleic acid, wherein each gene has its own promoter and terminator, was advantageous over the luciferase systems described in the prior art, whereby the technical problem was solved.

The present invention therefore relates to a nucleic acid comprising a continuous nucleotide sequence containing: (i) a gene encoding LuxA, (ii) a gene encoding LuxB, (iii) a gene encoding LuxC, (iv) a gene encoding LuxD, (v) a gene encoding LuxE, wherein each of the genes is under the control of a promoter heterologous to the respective gene, and wherein all genes together with the promoter are contained in a single nucleotide sequence in a row.

Preferably, the heterologous promoter is a eukaryotic promoter. Preferably, the heterologous promoters mediate approximately equal expression strength. Each gene may be followed by a terminator.

LuxA and LuxB are preferably from *Photorhabdus luminescens* or *Vibrio harveyi*, preferably *P. luminescens*. In the nucleic acid according to the invention, the genes encoding LuxA (i) and LuxB (ii) are preferably present as one gene luxAB encoding the LuxA/LuxB fusion protein and wherein LuxA and LuxB are preferably connected by a linker. The fusion protein or gene encoding the fusion protein is under the control of its own heterologous promoter and can thereby replace genes (i) and (ii) including their associated heterologous promoters in the nucleic acid according to the invention. LuxA preferably has an amino acid sequence that is at least 70%, at least 80%, at least 90%, at least 95%, at least 97.5%, at least 99% or 100% identical to SEQ ID NO: 1 or a functional fragment thereof. LuxB preferably has an amino acid sequence that is at least 70%, at least 80%, at least 90%, at least 95%, at least 97.5%, at least 99%, or 100% identical to SEQ ID NO: 2 or a functional fragment thereof.

LuxC, luxD and luxE are preferably from *P. luminescens*. LuxC preferably has an amino acid sequence that is at least 70%, at least 80%, at least 90%, at least 95%, at least 97.5%, at least 99%, or 100% identical to SEQ ID NO: 3 or a functional fragment thereof. LuxD preferably has an amino acid sequence that is at least 70%, at least 80%, at least 90%, at least 95%, at least 97.5%, at least 99%, or 100% identical to SEQ ID NO: 4 or a functional fragment thereof. LuxE preferably has an amino acid sequence that is at least 70%, at least 80%, at least 90%, at least 95%, at least 97.5%, at least 99%, or 100% identical to SEQ ID NO: 5 or a functional fragment thereof.

The nucleic acid preferably additionally comprises (vi) a gene encoding an NADPH-flavin oxidoreductase. The NADPH-flavin oxidoreductase is preferably frp, preferably from *V. harveyi*, wherein the NADPH-flavin oxidoreductase preferably has an amino acid sequence that is at least 70%, at least 80%, at least 90%, at least 95%, at least 97.5%, at least 99%, or 100% identical to SEQ ID NO: 6 or a functional fragment thereof.

The nucleic acid preferably does not contain an internal ribosomal entry site (IRES) and/or self-cleaving peptides, e.g., 2A peptides, between any of genes (i) to (vi).

LuxA and luxB or the LuxA/LuxB fusion protein are preferably under the control of a regulatable promoter, wherein the promoter is preferably regulatable by an environmental influence, (wherein the environmental influence) is preferably selected from the group consisting of medicaments, drugs, hormones, environmental toxins, bioavailable compounds and physical influences.

LuxC, luxD, luxE and optionally the NADPH-flavin oxidoreductase may be constitutively expressed or be under the control of an inducible promoter, wherein the promoter of luxC is preferably the TEF2 promoter, the promoter of luxD is preferably the CDC19 promoter, the promoter of luxE is preferably the ENO2 promoter, and/or the promoter of the NADPH-flavin oxidoreductase is preferably the PDC1 promoter. In one embodiment, luxC, luxD, luxE and optionally the NADPH-flavin oxidoreductase are under the control of an inducible promoter.

The present invention further relates to a vector, e.g., a plasmid, comprising the nucleic acid of the invention.

The present invention further relates to a host cell comprising the nucleic acid according to the invention or the vector according to the invention, wherein the host cell is preferably a eukaryotic host cell. Preferably, the host cell is a yeast, preferably a yeast selected from the group consisting of *Komagataella phaffii* (*Pichia pastoris*), *Hansenula polymorpha*, *Trichoderma reesei*, *Aspergillus niger*, *Saccharomyces cerevisiae*, *Kluyveromyces lactis*, *Yarrowia lipolytica*, *Pichia methanolica*, *Candida boidinii*, *Komagataella* spp., *Schizosaccharomyces pombe* and *Blastobotrys adeninivorans* (also known as *Arxula adeninivorans*), preferably *Saccharomyces cerevisiae*. The nucleic acid according to the invention may be integrated into a chromosome of the host cell.

The present invention further relates to a method of producing a host cell according to the invention comprising introducing the nucleic acid according to the invention or the vector according to the invention into a host cell.

The present invention further relates to a method for detecting an environmental agent comprising: (i) contacting an environmental sample with the host cell according to the invention; (ii) determining the luminescence of the host cell; wherein luxA and luxB or the LuxA/LuxB fusion protein are under the control of a regulatable promoter that is regulated by the environmental agent and wherein a change in bioluminescence compared to a control sample is indicative of the presence of the environmental agent, wherein the environmental agent is preferably selected from the group consisting of medicaments, drugs, hormones, environmental toxins, bioavailable compounds and physical agents.

The present invention further relates to a use of a host cell according to the invention as a biosensor or in a method for detecting an environmental effect according to the invention or for detecting protein-protein interactions.

The present invention further relates to the use of a host cell according to the invention as a vitality sensor, wherein the reduction or loss of bioluminescence is indicative of reduced vitality of the host cell.

The present invention further relates to a kit comprising the nucleic acid according to the invention, the vector according to the invention, or the host cell according to the invention.

FIGURES

FIG. 1 shows the measurement of luminescence (black) and growth (gray) of *S. cerevisiae* strain BY4742 containing plasmid pRS426-Lux, a nucleic acid according to the invention.

FIGS. 2A, 2B, 2C, and 2D show the bioluminescence of the host cell according to the invention. FIG. 2A shows the CSM-URA plate photographed at daylight and FIG. 2B in complete darkness. FIG. 2C is a schematic representation of the invention. FIG. 2D shows a comparison of the host cell according to the invention ("prototype", top line) with Firefly luciferase (middle line) and empty vector pRS426 (bottom line).

DETAILED DESCRIPTION

Figure 1:
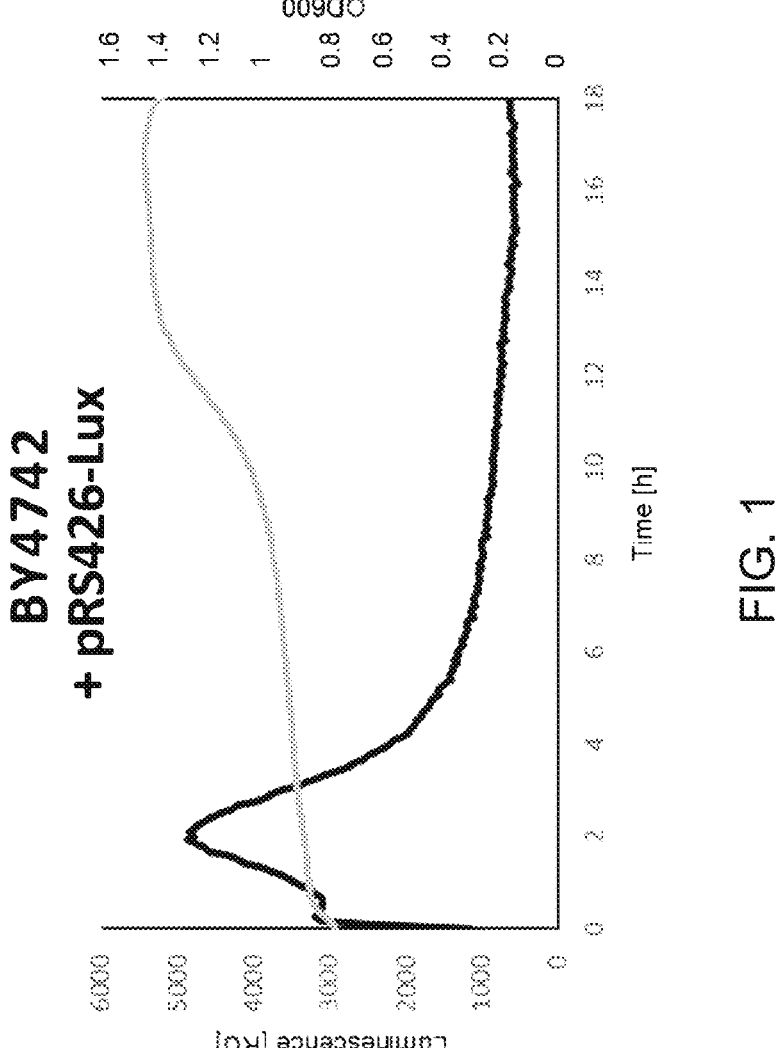
Figure 2C:
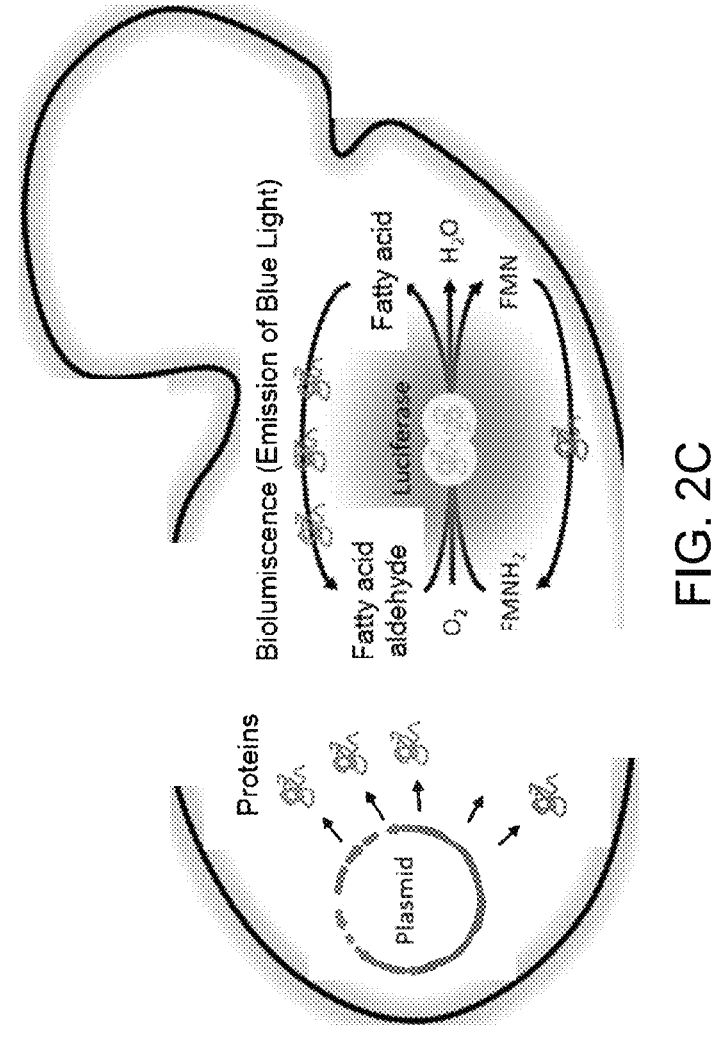
Figure 2A:
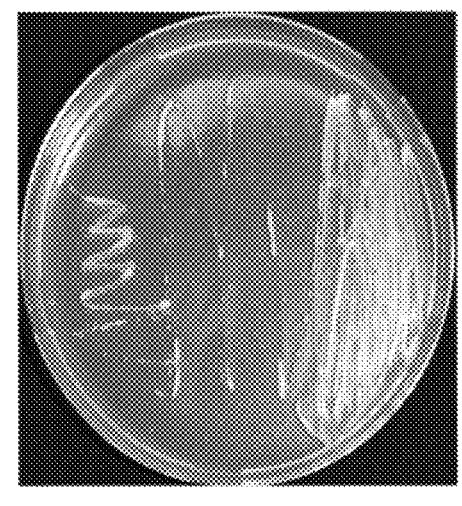
Figure 2B:
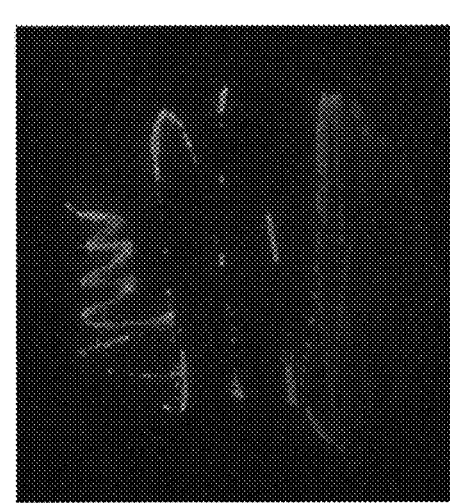
Figure 2D:
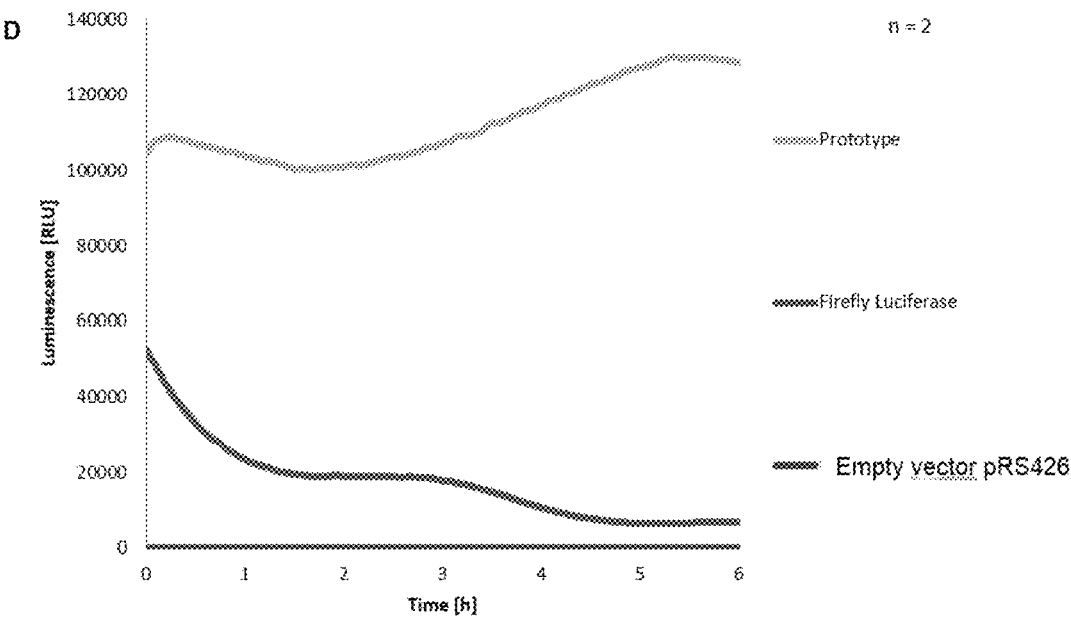

In 2018, the research group of Xu et al. reported that they had developed a bioluminescent reporter that could detect dioxins and dioxin-like substances. For this, the lux operon and frp were placed under control of a dioxin-sensitive promoter and the individual genes were linked via different viral 2A elements to allow expression with a single promoter. The 2A peptides were used due to their small sequence size (54-174 bp) (Xu et al., 2018). However, the use of these sequences also comes with some crucial disadvantages. For example, the 2A peptide remains as a C-terminal extension on the product located upstream, and the N-terminus of the downstream product is extended to include the amino acid proline. This C-terminal extension can cause the conformation of the protein to be compromised, resulting in limited or complete loss of activity (Minskaia et al., 2013). In addition, in certain cases, the C-terminal sequence of the upstream gene can completely inhibit the cutting of the 2A peptide. This can lead to aggregation of the proteins in the organism (Minskaia et al., 2013).

Another example known from the prior art of lux operon expression in *S. cerevisiae* was also relied on the use of viral elements. In this work, IRES sequences were used to bicistronically express luxE and frp and luxD and luxC. LuxAB and luxCDE+frp were also each cloned onto their own vectors (Gupta et al., 2003). However, IRES sequences have even greater disadvantages compared with 2A peptides. These sequences provide an additional binding site to ribosomes and recruit ribosomes independently of elongation factors inhibited by the viruses (Pelletier & Sonenberg, 1988). However, the required binding factors differ from cell to cell. In addition, the protein encoded downstream by IRES is usually expressed only 20%-50% in contrast to the protein encoded upstream (Mizuguchi et al., 2000).

The associated drawbacks therefore prevent a widespread applicability and reliability in the use of eukaryotic cells as biosensors. The solution found by the inventors avoids the use of viral factors. The nucleic acid according to the invention differs from the prior art in that, first, all of the genes of the lux operon are encompassed on a single nucleic acid and each of the genes of the lux operon is under the control of its own promoter. Host cells comprising the nucleic acid according to the invention can be used for a variety of different purposes, which we will discuss below.

As the inventors were able to show, the system they used is surprisingly clearly superior to a system split between two nucleic acids and the Firefly luciferase (see Example 3, FIG. 2). FIG. 2D shows the comparison of the plasmids pRS426-Lux, i.e. the nucleic acid according to the invention, and pRS426-FBA1::Firefly from the prior art, which have the same regulatory elements, during growth in appropriate deficiency medium. In the case of pRS426-Lux, no luciferin was added externally, whereas luciferin had to be added in excess to the Firefly plasmid. It can be seen that the luminescence signal of Firefly luciferase decreases very rapidly as the luciferin is simply consumed. In contrast, the bacterial luciferase produces a constant signal that is also more than twice as strong (FIG. 2D). This also allows a comparison with Xu et al. who report the luminescence intensity in "fold of induction" (FOI). FOI is the ratio of the average luminescence signal at time t to a negative control, which is also referred to as background lighting. Xu et al. obtain a maximum value of 13.8 FOI. Calculating the FOI for the highest value obtained in this disclosure (FIG. 2D), one would obtain an induction of 738 FOI (130,000 RLU signal versus 176 RLU background lights). This would mean a light signal more than 50 times stronger than that obtained by Xu et al, highlighting the clear superiority of the system according to the invention. Furthermore, another advantage of the bacterial lux system according to the invention is that the substrate can be produced by the host cell itself. By eliminating the addition and purchase of luciferin, labor time and costs can be reduced.

Accordingly, the present invention relates to a nucleic acid comprising a continuous nucleotide sequence containing: (i) a gene encoding LuxA, (ii) a gene encoding LuxB, (iii) a gene encoding LuxC, (iv) a gene encoding LuxD, (v) a gene encoding LuxE, wherein each of the genes is under the control of a promoter heterologous to the respective gene, and wherein all of the genes together with the promoter are contained in a single nucleotide sequence in a row.

The nucleic acid thus contains all essential genes that enable bioluminescence. The nucleic acid is continuous, i.e. all genes are located on a single, continuous nucleic acid. In other words, they are included together with the promoter in a single nucleotide sequence in a row. However, this does not necessarily preclude the possibility of non-coding regions or genes that are not from the lux operon being located between the individual genes. Also, it does not necessarily mean that the sequence of genes (i) through (vi) as described herein must be present on the nucleic acid in the order of their numbering.

As explained earlier, the nucleic acid contains genes encoding the lux operon. The genes responsible for prokaryotic bioluminescence were isolated and characterized from *Vibrio harveyi* by Engebrecht et al. (1983). These are referred to within this disclosure as the "lux operon". The genes contained in the lux operon are referred to as luxC, luxD, luxE, luxA, and luxB.

The bacterial luciferase is a heterodimer, which is formed by LuxA and LuxB (Foran and Brown, 1988). LuxA and LuxB hereby can be from *Photorhabdus luminescens* or *Vibrio harveyi*, wherein LuxA and LuxB preferably being from *P. luminescens*. In a preferred embodiment, LuxA has an amino acid sequence that is at least 70%, at least 80%, at least 90%, at least 95%, at least 97.5%, at least 99%, or 100% identical to SEQ ID NO: 1 or a functional fragment thereof. In a preferred embodiment, LuxB has an amino acid sequence that is at least 70%, at least 80%, at least 90%, at least 95%, at least 97.5%, at least 99%, or 100% identical to SEQ ID NO: 2 or a functional fragment thereof.

Another embodiment relates to a nucleic acid according to the present invention, wherein the genes encoding LuxA (i) and LuxB (ii) are present as a gene luxAB encoding the LuxA/LuxB fusion protein, and wherein LuxA and LuxB are preferably connected by a linker.

This means, according to this particular embodiment, LuxA and LuxB are present as a fusion protein (LuxA/LuxB fusion protein). Within the fusion protein, LuxA and LuxB may be connected by a linker, e.g. a serine-threonine linker or a serine-arginine linker, preferably a serine-arginine linker. The fusion protein or the gene encoding the fusion protein is under the control of its own heterologous promoter and can thereby replace genes (i) and (ii) including their associated heterologous promoters in the nucleic acid according to the invention. An exemplary fusion protein of LuxA and LuxB is shown in SEQ ID NO: 8. The LuxA/LuxB fusion protein may be under the control of an FBA1 promoter (as shown, for example, in SEQ ID NO: 13). Alternatively, the LuxA/LuxB fusion protein may be under the control of the OSI1 promoter (as shown, for example, in SEQ ID NO: 19). Consequently, the present invention accordingly also relates to a nucleic acid comprising a continuous nucleotide sequence containing: (i) a gene encoding a LuxA/LuxB fusion protein, (iii) a gene encoding LuxC, (iv) a gene encoding LuxD, (v) a gene encoding LuxE, wherein each of the genes is under the control of a promoter heterologous to the respective gene, and wherein all of the genes together with the promoter are contained in a single nucleotide sequence in a row.

The remaining genes of the lux operon luxC, luxD, and luxE are coding for a transferase (LuxD) and for a synthetase/reductase (LuxCE), which ensure that the aldehyde substrate required for the light reaction is present in a sufficient amount (Close et al., 2009). The aldehyde substrate for the bacterial luciferase is also referred to as bacterial luciferin in this context. The Lux operon is also the basis for other bioluminescent bacteria such as *Photobacterium phosphoreum* (Dunlap, 2014). LuxC, LuxD, and LuxE are preferably from *P. luminescens*. In a preferred embodiment, LuxC has an amino acid sequence that is at least 70%, at least 80%, at least 90%, at least 95%, at least 97.5%, at least 99%, or 100% identical to SEQ ID NO: 3 or a functional fragment thereof. In a preferred embodiment, LuxD has an amino acid sequence that is at least 70%, at least 80%, at least 90%, at least 95%, at least 97.5%, at least 99%, or 100% identical to SEQ ID NO: 4 or a functional fragment thereof. In a preferred embodiment, LuxE has an amino acid sequence that is at least 70%, at least 80%, at least 90%, at least 95%, at least 97.5%, at least 99%, or 100% identical to SEQ ID NO: 5 or a functional fragment thereof.

To support luciferin synthesis in the context of the invention, a NAPDH-flavin oxidoreductase may additionally be overexpressed or additionally expressed. This may be comprised on an additional nucleic acid or on the nucleic acid according to the invention. Preferably, the nucleic acid according to the invention (vi) comprises a gene encoding an NADPH-flavin oxidoreductase. Preferably, the NADPH-flavin oxidoreductase is frp, preferably frp from *Vibrio harveyi*. In a special embodiment, the NADPH-flavin oxidoreductase has an amino acid sequence that is at least 70%, at least 80%, at least 90%, at least 95%, at least 97.5%, at least 99% or 100% identical to SEQ ID NO: 6 or a functional fragment thereof.

A "functional fragment" in the context of the present invention means a fragment of each protein that has an activity of at least 50%, at least 60%, at least 70%, at least 80%, at least 90%, or at least 95% of the unmodified protein, i.e., the sequence recited in the present disclosure. Determining the activity of a protein is within the capabilities of the skilled person. For this purpose, the activity, e.g., luminescence, between the respective reference sequence and the fragment to be tested can be compared under otherwise identical conditions.

Sequence identity can be determined by any known method, but computer programs are useful for determining the degree of identity of sequences. Multiple sequence alignment and % identity calculations can be performed using standard BLAST parameters (use sequences from all available organisms, matrix BLOSUM 62, gap costs: existence 11, extension1). Alternatively, the program Align Plus 4, version 4.10 (Sci Ed Central Clone Manager Professional Suite) can be used with the following parameters: DNA comparison: Global comparison, Standard Linear Scoring Matrix, Mismatch Penalty=2, Open Gap Penalty=4, Extend Gap Penalty=1/Amino Acid Comparison: Global Comparison, BLOSUM 62 Scoring Matrix.

"Nucleic acid" as used herein describes macromolecules built from individual building blocks, the nucleotides, which in all organisms contain the genetic information. Alternating single sugars and phosphoric acid esters form a chain, wherein a nucleic base is attached to each sugar. The nucleic acid can be DNA or RNA, wherein DNA is preferred. When a nucleic acid is expressed, it leads to the production of the peptide or protein encoded by the respective gene.

In the nucleic acid according to the invention, each of the genes is under the control of an (own) promoter heterologous to the respective gene. The respective heterologous promoter is preferably a eukaryotic promoter. The promoters of the individual genes (i) to (v) or (i) to (vi) may be the same, but are preferably different. Preferably at least one promoter is different compared to the other promoters used, more preferably at least two promoters are different compared to the other promoters, wherein also the two promoters are different compared to each other, even more preferably at least three promoters are different compared to the other promoters, wherein also the three promoters are different compared to each other, most preferably all promoters used are different compared to each other. The term eukaryotic promoter may include synthetic promoters. The term eukaryotic promoter may include the cauliflower mosaic virus 35S promoter or other viral promoters.

Since the genes of the lux operon are equivalently expressed in bacteria, an attempt can be made to mimic this by using promoters of equal strength in eukaryotes. However, this is not essential for the feasibility of the invention. Therefore, the heterologous promoters preferably mediate equal expression strength. "Expression strength" in this context means the amount (e.g., number) of mRNA transcribed and/or the amount (e.g., mass) of proteins translated. "Equal" in this context may include a deviation of 25% or less, 10% or less, or 5% or less. Methods for determining the amount of mRNA and proteins are well known to those skilled in the art and are described, for example, in Sun et al. (2012), Biotechnology and Bioengineering 2012, 109:2082-2092. For example, quantitative PCR can be used to compare the transcribed amount of mRNA of the same gene, e.g., gfp, as a function of different promoters. Alternatively or additionally, a gene encoding a fluorescent protein such as GFP can be placed under the control of different promoters and the respective fluorescence determined as a function of the promoter.

The bioluminescence mediated by the expression products of the nucleic acid according to the invention can be used to detect a wide variety of factors, e.g. environmental influence. For this purpose, luxA and luxB or the LuxA/LuxB fusion protein are preferably under the control of a regulatable promoter. "Regulatable" in this context may mean induction of gene expression or repression of gene expression in response to an environmental influence. Thus, the regulatable promoter is preferably regulatable by an environmental influence.

In the context of the invention, it is advantageous if luxC, luxD, luxE and optionally the NADPH oxidoreductase are already expressed before the expression of the luciferase luxA/luxB. This has the advantage that the substrate luciferin can already be available in the host cell before the expression of the luciferase luxA/luxB is started. This may allow for a faster availability of bioluminescence, since the proteins that produce the substrate of luciferase do not have to be additionally expressed first. Accordingly, luxC, luxD, luxE, and optionally NADPH-flavin oxidoreductase may be constitutively expressed or under the control of a regulatable promoter. In one embodiment, luxC, luxD, luxE and optionally the NADPH-flavin oxidoreductase are under the control of an inducible promoter. In the case of a regulatable or inducible promoter, the promoters of luxC, luxD, luxE and optionally the NADPH-flavin oxidoreductase are preferably different from the (inducible) promoters of luxA and luxB. The promoter of luxC is preferably the TEF2 promoter (e.g. as shown in SEQ ID NO: 9), the promoter of luxD is preferably the CDC19 promoter (e.g. as shown in SEQ ID NO: 10), the promoter of luxE is preferably the ENO2 promoter (e.g. as shown in SEQ ID NO: 11) and/or the promoter of NADPH-flavin oxidoreductase is preferably the PDC1 promoter (e.g. as shown in SEQ ID NO: 12).

Each of genes (i) to (v) or (i) to (vi) may be followed by a terminator. A "terminator" or "transcription terminator" may refer to a segment of genetic sequence on DNA that marks the end of a gene or operon as it leads to the termination (termination) of transcription. Examples of terminators include, but are not limited to, the TEF2 terminator (as shown in SEQ ID NO: 14), the CDC19 terminator (as shown in SEQ ID NO: 15), the ENO2 terminator (as shown in SEQ ID NO: 16), the PDC1 terminator (as shown in SEQ ID NO: 17), or the FBA1 terminator (as shown in SEQ ID NO: 18).

As explained above, it is an advantage of the present invention that the nucleic acid according to the invention does not need to contain an IRES sequence or 2A peptide sequence. In cell biology, an internal ribosomal entry site, abbreviated IRES, is a specifically folded portion of the secondary structure of an RNA single strand that mediates binding to ribosomes. This allows translation to be initiated in the synthesis of proteins in eukaryotes independently of the 5'-cap structure, for example, even starting from the middle of a messenger RNA (mRNA). IRES have previously been found in the RNA of viruses as well as described in the mRNA for some genes of cells. 2A-self-cleaving peptides or 2A-peptides form a class of 18-22 amino acid long peptides that can induce cleavage of a recombinant protein in a host cell. For example, 2A peptides are derived from the 2A region of foot-and-mouth disease virus. In one embodiment, the nucleic acid of the invention does not contain an IRES sequence and/or a 2A peptide sequence between any of genes (i) to (vi).

The present invention further relates to a vector comprising the nucleic acid according to the invention. A "vector" or also "plasmid" refers to a nucleic acid that is suitable as a transport vehicle for transferring a foreign nucleic acid (e.g., DNA) into a (living) host cell by transfection or transduction. Exemplary for this purpose can be mentioned the pRS426 plasmid, which is described e.g. in (Mumberg et al., 1995) et al. The vector preferably contains one or more replication origins that allow for propagation or persistence in a host cell. These can be adapted by the skilled person depending on the intended host cell. A vector according to the invention is exemplified in SEQ ID NO: 7.

Methods for producing the nucleic acid or vector according to the invention are sufficiently known to those skilled in the art. In addition to cloning the individual genes into a nucleic acid or vector, the nucleic acid or vector may alternatively be produced by total synthesis. The genes may be codon-optimized depending on the host cell.

The present invention further relates to a host cell comprising the nucleic acid according to the invention or the vector according to the invention. Preferably, the host cell is a eukaryotic host cell. Especially preferably, the host cell is a yeast, wherein the yeast is preferably selected from the group consisting of *Komagataella phaffii* (*Pichia pastoris*), *Hansenula polymorpha, Trichoderma reesei, Aspergillus niger, Saccharomyces cerevisiae, Kluyveromyces lactis, Yarrowia lipolytica, Pichia methanolica, Candida boidinii, Komagataella* spp., *Schizosaccharomyces pombe*, and *Blastobotrys adeninivorans* (also known as *Arxula adeninivorans*). In a particularly preferred embodiment according to the invention, the host cell is *Saccharomyces cerevisiae*. In a particular embodiment, the host cell is *S. cerevisiae* strain BY4742, as described, for example, in Brachmann et al. 1998. The nucleic acid or vector according to the invention may be integrated into a chromosome of the host cell.

The present invention further relates to a method of producing a host cell according to the invention comprising introducing the nucleic acid according to the invention or the vector according to the invention into a host cell. Methods for introducing nucleic acids or vectors into a host cell are well known to those skilled in the art. For example, the host cell may be transformed or transduced with the nucleic acid or vector according to the invention.

The nucleic acid, the vector, or the host cell according to the invention can be used for a variety of purposes. One such purpose is to detect an environmental influence. In the context of using a regulatable promoter to control luxA and luxB or the LuxA/LuxB fusion protein, the change in bioluminescence can be observed and used to infer the presence or absence of the environmental influence. The strength of the luminescence can also be used for concentration determination (see also Example 4). Consequently, the present invention also relates to a method for detecting an environmental influence, comprising: (i) contacting an environmental sample with the host cell according to the invention; (ii) determining the luminescence of the host cell;

wherein luxA and luxB or the LuxA/LuxB fusion protein are optionally under the control of a regulatable promoter that is activated or influenced by the environmental influence and wherein an increase in bioluminescence compared to a control sample is indicative of the presence of the environmental influence (in the context of an inducible promoter) or wherein a decrease in bioluminescence compared to a control sample is indicative of the presence of the environmental influence (when using a repressible promoter). Such a method for detecting an environmental influence may be the basis for using the host cell as an environmental sensor. Preferably, no substrate for LuxA/LuxB luciferase is added externally to the host cell. In one embodiment, luxA and luxB or the LuxA/LuxB fusion protein are not under the control of a regulatable promotor, but under the control of a constitutive promoter. In this case, if the environmental influence alters (strengthen or weaken) the growth of the host cell, the change in bioluminescence can be used to detect the environmental influence. Consequently, the present invention also relates to a method for detecting an environmental influence comprising: (i) contacting an environmental sample with the host cell according to the invention; (ii) determining the luminescence of the host cell; wherein luxA and luxB or the LuxA/LuxB fusion are optionally under the control of a constitutive promoter, and wherein a change in bioluminescence compared to a control sample is indicative of the presence of the environmental influence.

An "environmental influence" in the context of the present disclosure means any influence that is capable of altering gene expression of a gene under the control of a regulatable promoter, and/or is lethal or growth inhibitory to the host cell. This can be in terms of an analyte, a synthetic or natural compound, bioavailable compound (such as nutrients, amino acids, nucleic acids, nitrogen, phosphorus, sulfur), a physical influence that can act directly or indirectly (indirect meaning, for example, when an analyte activates a signaling pathway that ultimately acts on the regulatory element) on the regulatory element. Thus, the system can be used as an indicator of environmental influences, as well as for gene expression and regulation, and monitoring of bioavailable compounds, as bioluminescence is altered/regulated in response to metabolism (protein synthesis, DNA synthesis) or growth. Examples of environmental influences include medicaments, drugs, hormones, environmental toxins, bioavailable compounds, and physical influences.

"Medicaments" may include substances and preparations used in humans or animals and intended to cure, alleviate, or prevent disease or pathological conditions, or to restore, correct, or influence physiological functions. They can also serve as a basis for medical diagnoses. The environmental influence can be an antibiotic.

"Drugs" may include the following: benzodiazepines, thienodiazepines, indole alkaloids (e.g., LSD), opioids (e.g., morphine, diacetylmorphine, methadone), arylcyclohexylamines (e.g., ketamine), phenylethylamines (e.g., amphetamines), tropane alkaloids (e.g., cocaine, scopolamine), xanthines, or cannibinoids (e.g., cannabidiol, THC).

"Hormones" can be endogenous or non-endogenous, but hormone-like substances. Examples are estrogens, gestagens, but also substances that have hormone-like effects such as DDT, PCB, PBDE or phthalates.

As "environmental toxins" can be understood substances or preparations which themselves or their transformation products are capable of changing the condition of the natural balance, water, soil or air, climate, animals, plants or microorganisms in such a way that hazards to the environment can be brought about immediately or later. Environmental toxins can be chemical substances that are classified as "environmentally hazardous" under the GHS labeling. Examples include dichlorodiphenyltrichloroethane (DDT), volatile halogenated hydrocarbons (VHHs such as dichloromethane, trichloromethane, trichloroethane), pentachlorophenol (PCP), polybrominated diphenyl ethers (PBDEs), polychlorinated biphenyls (PCBs), polychlorinated dibenzodioxins and dibenzofurans, polycyclic aromatic hydrocarbons (PAHs such as. e.g. benzo[a]pyrene), propenal, sulfur trioxide, heavy metals (e.g. arsenic, antimony, lead, cadmium, chromium, copper, nickel, thallium, mercury) or TMDD.

A "bioavailable compound" can be understood as a substance or mixture of substances that can be metabolized by organisms without harming them. Examples include nutrients, nitrogen and nitrogen compounds, phosphorus and phosphorus compounds, and sulfur and sulfur compounds.

A "physical influence" may refer to an environmental influence that can affect a host cell via parameters such as heat, cold, or osmotic concentration. Another physical influence may be oxidative stress. To detect oxidative stress, the OSI1 promoter can be used to control the expression of luxA/luxB.

An "environmental sample" may refer to a sample obtained from the environment, i.e., not from an animal, for example. Exemplary environmental samples are water samples (e.g., sea, lakes, streams, wastewater, drinking water) or soil samples, preferably water samples.

Methods for measuring bioluminescence are sufficiently known to the skilled person. They include, for example, the use of a photometer e.g. within a (micro) plate reader. The basis of these methods is the measurement of light emitted by the host cell. The activity of the bacterial LuxA/LuxB luciferase described in this disclosure can be measured at about 490 nm.

As mentioned herein, the host cell according to the invention can be used as a biosensor. Consequently, the invention also relates to the use of the host cell as a biosensor. "Biosensor" in the context of the invention may refer to the use of the host cell according to the invention to detect an environmental effect, e.g., in a method of detecting an environmental effect as described herein. Preferably, no substrate for LuxA/LuxB luciferase is added externally to the host cell.

The host cell according to the invention can additionally be used as a vitality sensor. In an exemplary embodiment, luxA and luxB or the LuxA/LuxB fusion protein are under the control of a constitutively active promoter. That is, the luminescence of the host cell remains constant. If the vitality of the host cell decreases, e.g., due to the influence of an environmental toxin, the host cell may restrict the protein production or die, causing the luminescence to decrease. That is, the level of luminescence may serve as an indicator of the vitality of the host cell. Consequently, the present invention relates to the use of the host cell according to the invention as a vitality sensor, wherein the decrease or loss of (bio)luminescence is indicative of decreased vitality of the host cell. Preferably, no substrate for LuxA/LuxB luciferase is added externally to the host cell.

The nucleic acid according to the invention may also be used to detect protein-protein interactions. For this purpose, a system similar to a yeast two-hybrid system (Y2H) may be used. In an exemplary embodiment, the substrate for the LuxA/LuxB luciferase can be produced by the genes luxC, luxD, luxE and optionally NAPDH-flavin oxidoreductase, which are under the control of a constitutive promoter. At the same time, the luxA/luxB genes or the LuxA/LuxB fusion protein are under the control of a promoter activated by the binding of the reconstituted transcription factor in the Y2H system. A Gal4 promoter is often used for this purpose, which is activated by the reconstituted Gal4 transcription factor in the presence of protein-protein interaction. A luciferase-based system is described in Massoud et al. 2007.

Preferably, no substrate for LuxA/LuxB luciferase is added externally to the host cell.

The present invention further relates to a kit comprising the nucleic acid according to the invention, the vector according to the invention, or the host cell according to the invention. The kit may additionally comprise instructions. Other components may include sample collection containers, culture media, or means for transfecting the nucleic acid.

The present invention also relates to the following objects:

Nucleic acid comprising a continuous nucleotide sequence containing:

a gene encoding LuxA, (ii) a gene encoding LuxB, (iii) a gene encoding LuxC, (iv) a gene encoding LuxD, (v) a gene encoding LuxE, wherein each of the genes is under the control of a promoter heterologous to the respective gene, and wherein all of the genes together with the promoter are contained in a single nucleotide sequence in a row.

2. Nucleic acid according to object 1, wherein the heterologous promoter is a eukaryotic promoter.

3. Nucleic acid according to object 1 or 2, wherein the heterologous promoters mediate approximately equal expression levels.

4. Nucleic acid according to any of the preceding objects, wherein each gene is followed by a terminator.

5. Nucleic acid according to any of the preceding objects, wherein LuxA and LuxB are from *Photorhabdus luminescens* or *Vibrio harveyi*, preferably *P. luminescens*.

6. Nucleic acid according to any one of the preceding objects, wherein the genes encoding LuxA (i) and LuxB (ii) are present as a gene luxAB encoding the LuxA/LuxB fusion protein, and wherein LuxA and LuxB are preferably connected by a linker.

7. Nucleic acid of any one of the preceding objects, wherein LuxA has an amino acid sequence that is at least 70%, at least 80%, at least 90%, at least 95%, at least 97.5%, at least 99%, or 100% identical to SEQ ID NO: 1 or a functional fragment thereof.

8. Nucleic acid of any one of the preceding objects, wherein LuxB has an amino acid sequence that is at least 70%, at least 80%, at least 90%, at least 95%, at least 97.5%, at least 99%, or 100% identical to SEQ ID NO: 2 or a functional fragment thereof.

9. Nucleic acid according to any one of the preceding items, wherein LuxC, LuxD and LuxE are from *P. luminescens*.

10. Nucleic acid of any one of the preceding objects, wherein LuxC has an amino acid sequence that is at least 70%, at least 80%, at least 90%, at least 95%, at least 97.5%, at least 99%, or 100% identical to SEQ ID NO: 3 or a functional fragment thereof.

11. Nucleic acid of any one of the preceding objects, wherein LuxD has an amino acid sequence that is at least 70%, at least 80%, at least 90%, at least 95%, at least 97.5%, at least 99%, or 100% identical to SEQ ID NO: 4 or a functional fragment thereof.

12. Nucleic acid of any one of the preceding objects, wherein LuxE has an amino acid sequence that is at least 70%, at least 80%, at least 90%, at least 95%, at least 97.5%, at least 99%, or 100% identical to SEQ ID NO: 5 or a functional fragment thereof.

13. Nucleic acid according to any one of the preceding objects, wherein the nucleic acid additionally comprises (vi) a gene encoding an NADPH-flavin oxidoreductase.

14. Nucleic acid of object 13, wherein the NADPH-flavin oxidoreductase is frp, preferably from *V. harveyi*, wherein the NADPH-flavin oxidoreductase preferably has an amino acid sequence that is at least 70%, at least 80%, at least 90%, at least 95%, at least 97.5%, at least 99%, or 100% identical to SEQ ID NO: 6 or a functional fragment thereof.

15. Nucleic acid according to any one of the preceding objects, wherein the nucleic acid does not contain an internal ribosomal entry site (IRES) and/or does not contain self-cutting peptides, e.g. 2A peptides, between any of genes (i) to (vi).

16. Nucleic acid according to any one of the preceding objects, wherein luxA and luxB or the luxA/LuxB fusion protein are under the control of a regulatable promoter, wherein the promoter is preferably regulatable by an environmental influence, preferably selected from the group consisting of medicaments, drugs, hormones, environmental toxins, bioavailable compounds and physical influences.

17. Nucleic acid according to any one of the preceding objects, wherein luxC, luxD, luxE and optionally the NADPH flavin oxidoreductase are constitutively expressed or under the control of a regulatable promoter, wherein the promoter of luxC is preferably the TEF2 promoter, the promoter of luxD is preferably the CDC19 promoter, the promoter of luxE is preferably the ENO2 promoter, and/or the promoter of NADPH-flavin oxidoreductase is preferably the PDC1 promoter.

18. Vector, e.g. a plasmid, comprising the nucleic acid of any one of objects 1 to 17.

19. Host cell comprising the nucleic acid of any one of objects 1 to 17 or the vector of object 18, wherein the host cell is preferably a eukaryotic host cell.

20. Host cell according to object 19, wherein the host cell is a yeast, preferably a yeast selected from the group consisting of *Komagataella phaffii* (*Pichia pastoris*), *Hansenula polymorpha*, *Trichoderma reesei*, *Aspergillus niger*, *Saccharomyces cerevisiae*, *Kluyveromyces lactis*, *Yarrowia lipolytica*, *Pichia methanolica*, *Candida boidinii*, *Komagataella* spp., *Schizosaccharomyces pombe* and *Blastobotrys adeninivorans*, preferably *Saccharomyces cerevisiae*.

21. Method of making a host cell according to object 19 or 20 comprising introducing the nucleic acid according to any one of articles 1 to 17 or the vector according to article 18 into a host cell.

22. Method for detecting an environmental effect, comprising:

Contacting an environmental sample with the host cell according to object 19 or 20;

(ii) Determining the luminescence of the host cell;

wherein luxA and luxB or the luxA/LuxB fusion protein are optionally under the control of a regulatable promoter that is regulated by the environmental influence and wherein a change in bioluminescence compared to a control sample is indicative of the presence of the environmental influence.

23. Method according to object 22, wherein the environmental influence is selected from the group consisting of medicaments, drugs, hormones, environmental toxins, bioavailable compounds and physical influences.

24. Use of a host cell according to objects 19 or 20 as a biosensor, in a method according to subject matter 22 or 23, or for detecting protein-protein interactions.

25. Use of a host cell according to any one of objects 19 or 20 as a vitality sensor, wherein the reduction or loss of bioluminescence is indicative of reduced vitality of the host cell.

26. Kit comprising the nucleic acid according to any one of objects 1 to 17, the vector according to object 18, or the host cell according to object 19 or 20.

We note that the singular forms "a", and the" used herein include plural references unless the context clearly indicates otherwise. For example, reference to "a reagent" includes one or more such different reagents, and reference to "the method" includes reference to equivalent steps and methods known to those skilled in the art that could modify or replace the methods described herein.

Unless otherwise indicated, the term "at least" before a series of elements should be understood to refer to each element in the series. Those skilled in the art may recognize or be able to find through routine experimentation many equivalents to the specific embodiments of the invention described herein. Such equivalents are intended to be encompassed by the present invention.

The term "and/or" includes the meanings of "and", "or", and "all or any other combination of the elements connected by this term".

The term "less than" or, conversely, "more than" does not include the specific number specified. For example, "less than 20" means less than the specified number. Similarly, "more than" or "greater than" means the specified number, e.g. "more than 80%" means more than or greater than the specified number of 80%.

In this description and in the following claims, unless the context indicates otherwise, the word "including" and variations such as "include" are understood to mean the inclusion of a specified integer or steps or group of integers or steps, but not the exclusion of any other integer or step or group of integers or steps. When used herein, the term "includes" may be substituted for the term "contains" or "includes" or sometimes, when used herein, for the term "has". When used herein, "consisting of" excludes any element, step, or ingredient not specified.

The term "including" means "including but not limited to". The terms "including" and "including but not limited to" are used interchangeably.

It should be understood that the present invention is not limited to the particular methodology, protocols, material, reagents and substances, etc., described herein and as such may vary. The terminology used herein is for the purpose of describing specific embodiments only and is not intended to limit the scope of the present invention, which is defined solely by the claims.

All publications cited throughout the text of this description (including all patents, patent applications, scientific publications, instructions, etc.), whether cited before or after, are hereby incorporated by reference in their entirety. Nothing herein shall be construed as an admission that the invention is not entitled to such prior disclosure by virtue of any prior invention. To the extent that the disclosure incorporated by reference contradicts or is inconsistent with this description, the description supersedes any such disclosure.

The following examples, which are provided for illustrative purposes only, are intended to aid in understanding the present invention and its advantages. The examples are not intended to limit the scope of the present invention in any way.

EXAMPLES

Materials and Methods

Yeast and Bacteria Strains

In this work, *Saccharomyces cerevisiae* strain BY4742 (genotype: MATα his3 Δ1 leu2 Δ0 lys2Δ0 ura3 Δ0) was used, which originated from the gene knockout collection of Euroscarf in Oberursel, Germany (Ando & Suzuki, 2005; Brachmann et al., 1998).

Media Used

YPD (for *S. cerevisiae*)

| Components | Final concentration |
| --- | --- |
| Peptone | 20 g/L |
| D-glucose | 20 g/L |
| Yeast extract | 10 g/L |
| Agar (for solid medium) | 15 g/L |

SD-URA Medium (for *S. cerevisiae*)

| Components | Final concentration |
| --- | --- |
| D-glucose | 20 g/L |
| Ammonium sulfate | 5 g/L |
| Yeast Nitrogen Base | 1.7 g/L |
| CSM -URA | 0.77 g/L |
| Agar (for solid medium) | 15 g/L |

SD-Leu Medium (for *S. cerevisiae*)

| Components | Final concentration |
| --- | --- |
| D-glucose | 20 g/L |
| Ammonium sulfate | 5 g/L |
| Yeast Nitrogen Base | 1.7 g/L |
| CSM -Leu | 0.69 g/L |
| Agar (for solid medium) | 15 g/L |

SD-Leu-URA Medium (for *S. cerevisiae*)

| Components | Final concentration |
| --- | --- |
| D-glucose | 20 g/L |
| Ammonium sulfate | 5 g/L |
| Yeast Nitrogen Base | 1.7 g/L |
| CSM-Leu-URA | 0.67 g/L |
| Agar (for solid medium) | 15 g/L |

Plasmids

| Name | Property | Reference |
| --- | --- | --- |
| pRS426 | High-copy plasmid containing f1 ori, ColE1, beta-lactamase sequence and URA3 sequence. | (Mumberg et al., 1995). |
| pGADT7 AD | yeast two-hybrid "prey" plasmid for the expression of proteins associated with the GAL4 domain. | (Chien et al., 1991) |

Transformation of Yeasts

Transformation is based on the protocol of Gietz and Woods (2002) and on Jansen et al. (2005) with some modifications: Yeasts were incubated on YPD agar plates overnight for 1-2 days at 28° C. Cell layers corresponding to a 1-μl inoculation loop were added to 50 μl of previously boiled and then cooled herring sperm (2 mg/ml in 10 mM TRIS-HCl, 1 mM Na2 EDTA, pH 8) and mixed. Then, first the DNA to be transformed—and a mixture of 240 μl of 50% polyethylene glycol 6000 (weight/volume) and 36 μl of 1 M lithium acetate were added. After incubation at 30° C. for 30 minutes, heat shock was performed at 42° C. for 30 minutes. Cells were then pelleted at 3000×g for 10 minutes at room temperature. The supernatant was discarded and the cell pellet was taken up in 100 μl of distilled and sterilized water and spread on selection medium with appropriate selection. These plates were incubated at 28° C. until transformants appeared.

Luminescence Measurement

D-Luciferin sodium salt (Carl Roth, Germany) was dissolved in 0.1 M Na2 HPO4-citrate buffer pH 5 to a final luciferin concentration of 1 mM. 100 μl of an overnight yeast culture was adjusted depending on the experimental question to a suitable starting OD600 of around 1.0 or less in CSM medium. 100 μl of yeast cells, 25 μl of a test solution (e.g., amino acid), and 25 μl of 1 mM luciferin solution were added in this order to a well of a black 96-well microtiter plate with a transparent bottom (Microplate, 96 well, PS, F-Bottom (Chimney Well) μClear®, Black, Med. Binding; Greiner bio-one, Germany) for a measurement. Measurements were performed using a Tristar2S Platereader (Berthold, Germany) at a constant temperature of 28° C.

Figure 5:
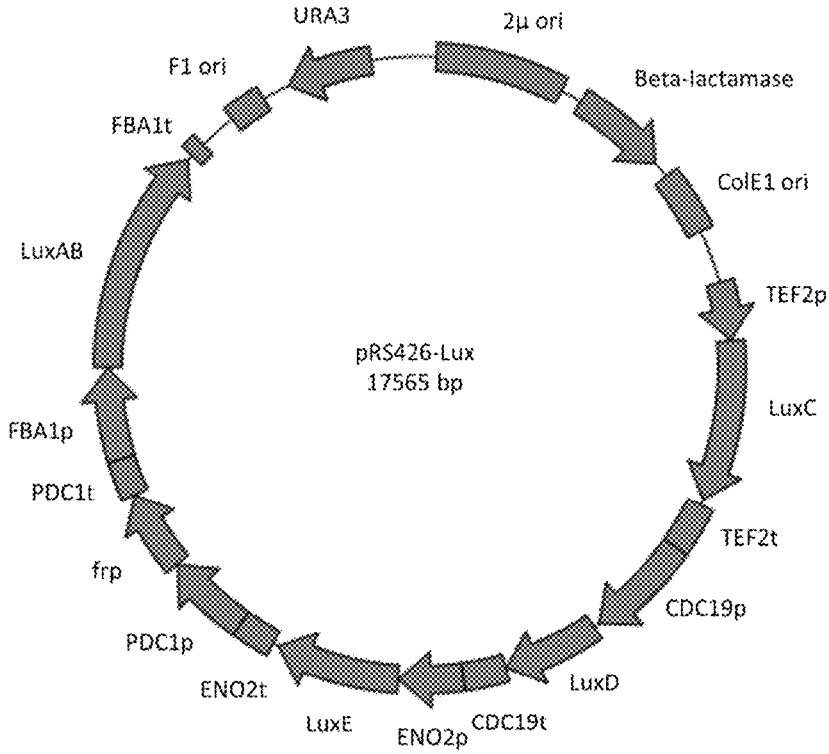
FIG. 5 shows an example of a nucleic acid according to the invention based on the pRS426 plasmid (see also SEQ ID NO: 7).

Example 1: Transformation of Plasmid pRS426-Lux into BY4742 and Growth and Luminescence Comparison Measurement Plasmid pRS426-Lux (SEQ ID NO: 7, see also FIG. 5) was chemically transformed into *S. cerevisiae* strain BY4742. After two days, 86 colonies were obtained. After the colonies were separated on CSM-Ura selection plates, luminescence was successfully measured (FIG. 1). FIG. 1 shows strain BY4742 starting at a luminescence of about 3000 RLU, increasing to a maximum of 5000 RLU. Thus, the nucleic acid according to the invention can generate bioluminescence in yeast without the addition of external luciferase substrate.

Figure 6:
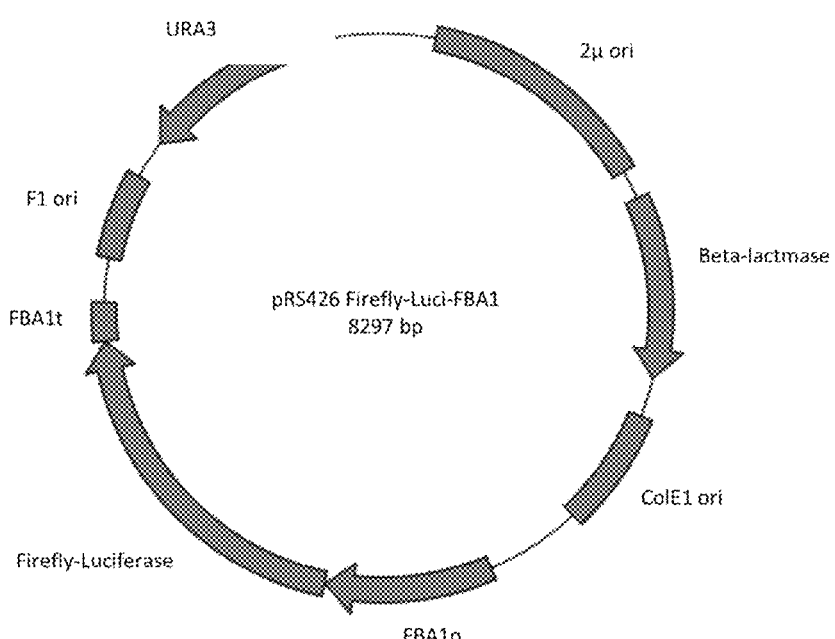
FIG. 6 shows an exemplary plasmid encoding Firefly luciferase (SEQ ID NO: 20).

Example 2: Comparison of the Bacterial Luciferase According to the Invention with the Firefly Luciferase To compare the generated construct according to the invention pRS426-Lux (SEQ ID NO: 7) in terms of growth behavior and luminescence, a luciferase was placed under the same promoter and terminator as the bacterial luciferase LuxAB (SEQ ID NO: 20) to establish comparable conditions. The luciferase from Photinus pyralis was chosen for comparison because it is most commonly used in bioanalysis (see FIG. 6).

After both plasmids have the same genetic requirements, such as FBA1 promoter and terminator, the same vector backbone and were also transformed into BY4742, both plasmids could be directly compared. The experiment was performed twice with three technical replicates each time. The cultures were grown overnight at 28° C. and were each diluted with 50 μl of fresh medium (YPD medium). For the produced prototype (nucleic acid according to the invention, SEQ ID NO: 7), water was added instead of 50 μl of the luciferin solution (2 mM final concentration).

The nucleic acid according to the invention ("prototype") shows an initial luminescence of about 100,000 RLU and slowly rises to 130,000 RLU after 5.4 h. The luminescence of the Firefly luciferase is about 100,000 RLU. In contrast, the Firefly luciferase starts at only 52,475 RLU and decreases to 19,143 RLU after only 1.7 h. The luminescence of the Firefly luciferase is very low. After 5.4 h, only a low luminescence of 6893 can be measured (see FIG. 2D). The CSM-URA plates were photographed in daylight (FIG. 2A) and in complete darkness (FIG. 2B) by a commercial photographic camera. The naked eye was also able to perceive the light produced by the yeasts.

Based on these data, it is clear that the nucleic acid of the present invention is far superior to conventional Firefly luciferase.

Figure 3:
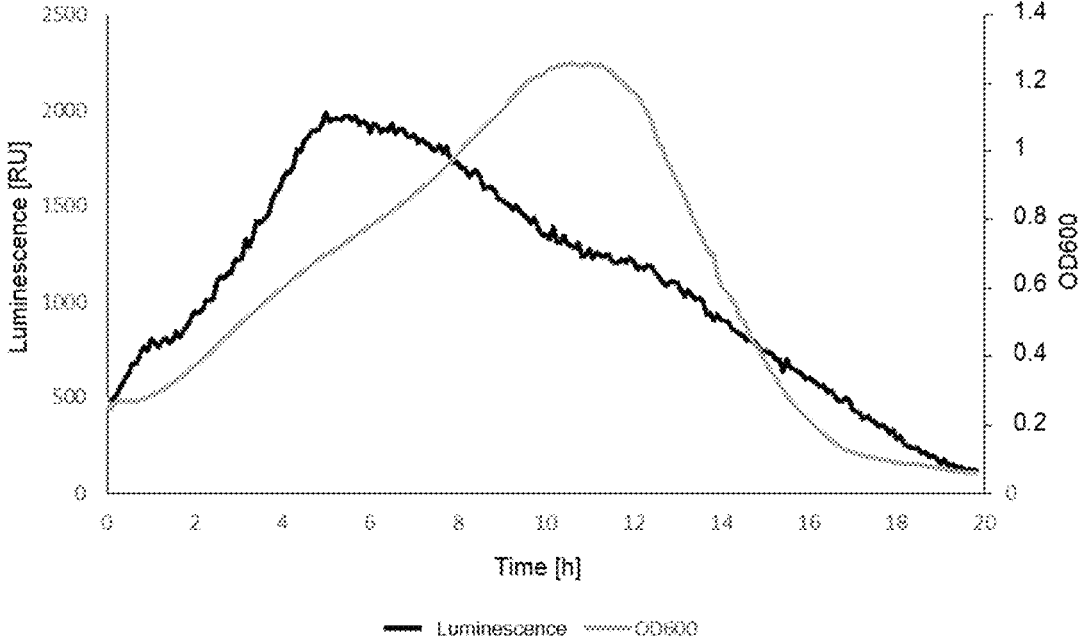
FIG. 3 shows a luminescence measurement of *S. cerevisiae* (dark line) as well as the OD600 (light line), which were transformed with plasmids pRS426-Leu2-LuxAB and pRS426-Ura3-LuxCDE-frp.
Figure 7:
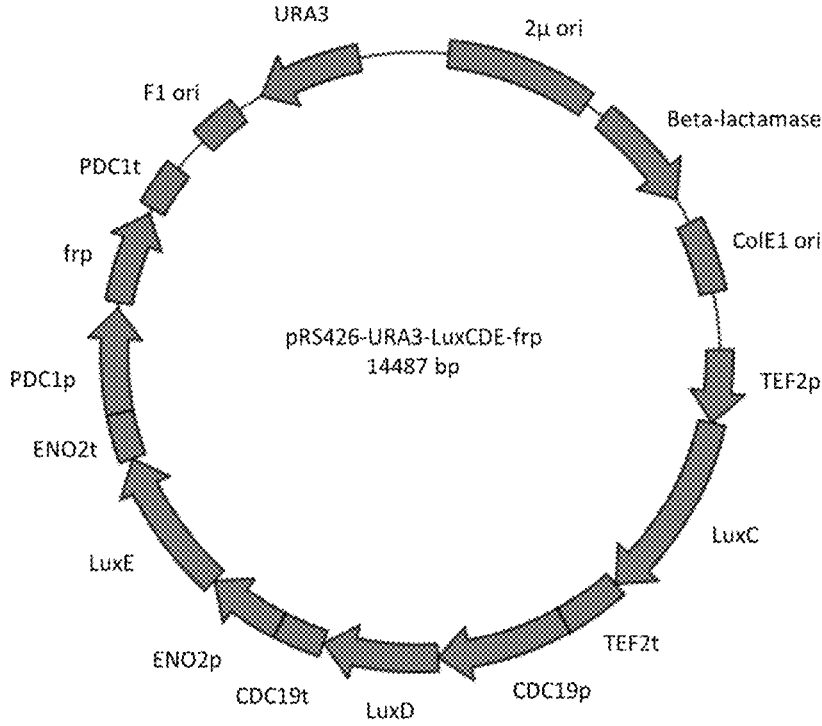
FIG. 7 shows two example plasmids encoding LuxA/B (SEQ ID NO: 22) and LuxC/D/E (SEQ ID NO: 21) on two different plasmids.
Figure 7:
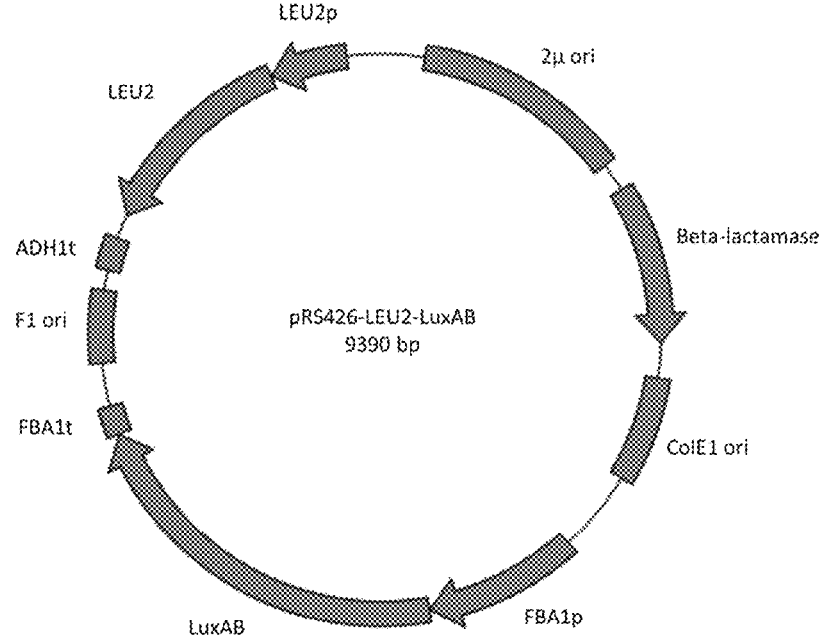

Example 3: Construction of a Biosensor Based on Lux Bioluminescence Plasmids A plasmid was cloned, which constitutively expresses luciferase. Thus, the luminescence of the plasmid pRS426-Lux (SEQ ID NO: 7), which combines luciferin and luciferase synthesis on a single plasmid (FIG. 5), was to be compared with a system based on the two plasmids pRS426-Leu2-FBA1::LuxAB (SEQ ID NO: 22) and pRS426-URA3-LuxCDE-frp (SEQ ID NO: 21, FIG. 7). After the transformed yeasts were grown overnight, luminescence could be measured. 100 μl of the yeast culture and 50 μl of fresh culture medium were added to a measurement well (FIG. 3).

Contrary to the expectations, it was surprisingly shown that splitting the luciferin and luciferase synthesis between two plasmids did not result in higher luminescence. On the contrary—a significantly lower luminescence was measured here (FIG. 3) in contrast to the nucleic acid pRS426-Lux according to the invention. In the system based on two plasmids, the luminescence peaked after 5.3 h at only 1948 RLU.

Thus, the inventors were completely surprised to find that splitting into two plasmids had no positive effect on luminescence, but on the contrary, that expression of the lux operon from one nucleic acid according to the invention was beneficial.

Example 4: Detection of Leucine Using the System According to the Invention

There are many possibilities to use the luciferase system of the invention as a biosensor. As an example, this will be demonstrated by detecting the leucine concentration in a leucine deficiency medium.

Figure 4:
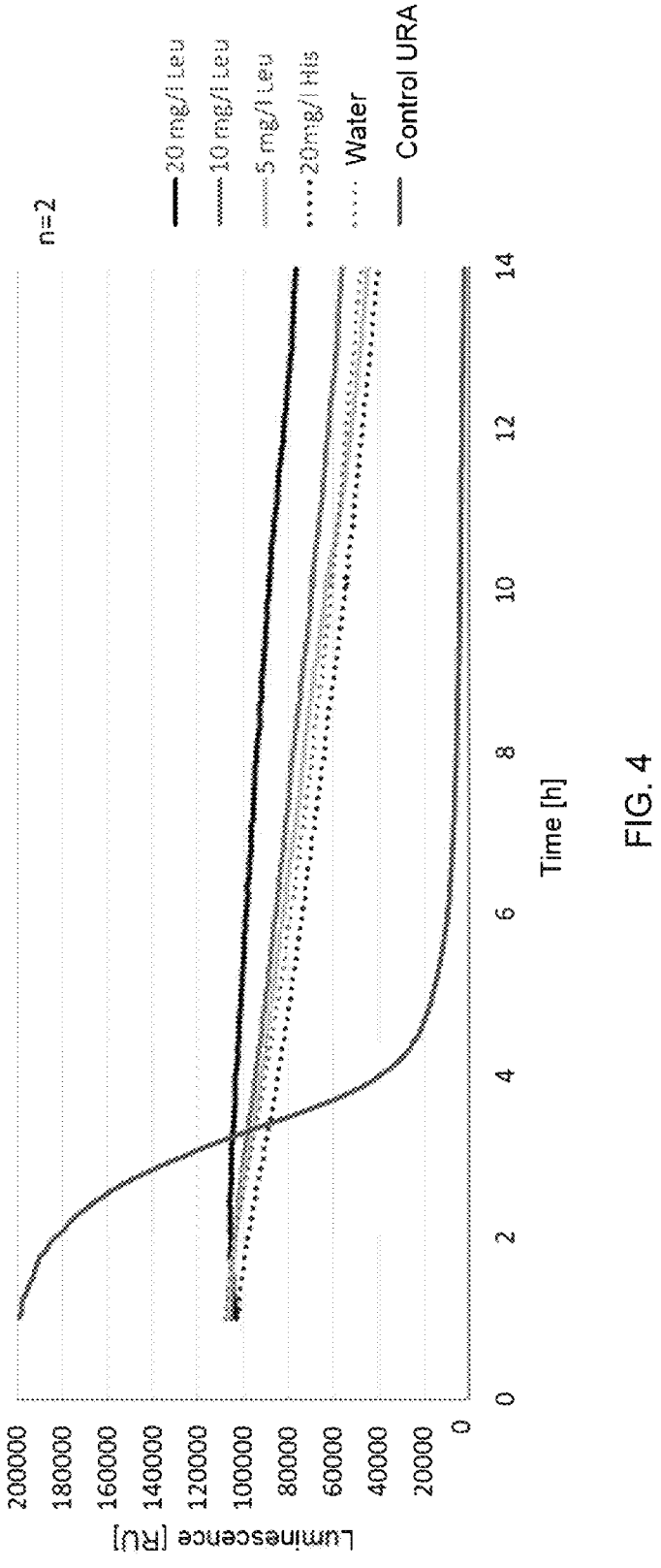
FIG. 4 shows the course of luminescence at different concentrations of leucine and controls (water, URA and histidine), respectively.

The yeast strain BY4742 used by the inventors has several auxotrophies, including leucine auxotrophy, which makes this strain useful for leucine detection. For this purpose, the strain was grown overnight in CSM-URA medium. Since the vector pRS426-Lux (SEQ ID NO: 7, see also FIG. 5) contains a URA3 marker, normal growth is possible for these yeast cells. The next day, the cells were centrifuged and included in CSM-Leu-URA medium, i.e., medium without leucine. Consequently, these cells could not grow due to absence of the amino acid leucine. After 5 h of incubation, a defined amount of leucine was added and luminescence was subsequently measured (FIG. 4). However, it was observed that from a leucine concentration >49 mg/L, the organisms grow and the light signal increases regardless of the concentration. However, if less than 20 mg/L leucine is added, this amount has a limiting effect on cell metabolism, and thus on the maximum possible bioluminescence. By consuming the available leucine, it becomes more and more limited, causing cell metabolism and thus bioluminescence to decrease over time (FIG. 4). The relationship between available leucine and measured bioluminescence behaves in a concentration-dependent manner within a certain concentration range, so that the leucine concentration can be correlated and measured with the bioluminescence.

The nucleic acid according to the invention can thus be used with the aid of a host cell (according to the invention) to detect and quantify environmental influences such as leucine.

REFERENCES

Ando, A., & Suzuki, C. (2005). Cooperative function of the CHD5-like protein Mdm39p with a P-type ATPase Spf1p in the maintenance of ER homeostasis in *Saccharomyces cerevisiae*. *Molecular Genetics and Genomics*, 273(6), 497-506. https://doi.org/10.1007/s00438-005-1153-6

Bhaumik, S., & Gambhir, S. S. (2002). Optical imaging of *Renilla* luciferase reporter gene expression in living mice. *Proceedings of the National Academy of Sciences of the United States of America*, 99(1), 377-82. https://doi.org/10.1073/pnas.012611099

Brachmann, C. B., Davies, A., Cost, G. J., Caputo, E., Li, J., Hieter, P., & Boeke, J. D. (1998). Designer deletion strains derived from *Saccharomyces cerevisiae* S288C: A useful set of strains and plasmids for PCR-mediated gene disruption and other applications. *Yeast*, 14(2), 115-132. https://doi.org/10.1002/(SICI)1097-0061(19980130)14:2<115::AID-YEA204>3.0.CO;2-2

Chien, C. T., Bartel, P. L., Sternglanz, R., & Fields, S. (1991). The two-hybrid system: a method to identify and clone genes for proteins that interact with a protein of interest. *Proceedings of the National Academy of Sciences*, 88(21), 9578-9582. https://doi.org/10.1073/pnas.88.21.9578

Close, D. M., Ripp, S., & Sayler, G. S. (2009). Reporter proteins in whole-cell optical bioreporter detection systems, biosensor integrations, and biosensing applications. *Sensors*, 9(11), 9147-9174. https://doi.org/10.3390/s91109147

Contag, C. H., Contag, P. R., Mullins, J. I., Spilman, S. D., Stevenson, D. K., & Benaron, D. A. (1995). Photonic detection of bacterial pathogens in living host cells. *Molecular Microbiology*, 18, 593-603.

Contag, P. R., Olomu, I. N., Stevenson, D. K., & Contag, C. H. (1998). Bioluminescent indicators in living mammals. *Nature Medicine*, 4(2), 245-247.

Dunlap P. 2014. Biochemistry and Genetics of Bacterial Bioluminescence. In *Bioluminescence: Fundamentals and Applications in Biotechnology-Volume* 1, pp. 37-64, Springer-Verlag Berlin Heidelberg.

Engebrecht J, Nealson K, Silverman M. 1983. Bacterial bioluminescence: isolation and genetic analysis of functions from *Vibrio fischeri. Cell* 32: 773-781.

Foran, D. R., & Brown, W. M. (1988). Nucleotide sequence of the LuxA and LuxB genes of the bioluminescent marine bacterium *Vibrio fischeri,* 16(2), 777.

Daniel Gietz, R.; Woods, R. A. Transformation of yeast by lithium acetate/single-stranded carrier DNA/polyethylene glycol method. In *Methods in Enzymology*; Guthrie, C., Fink, G. R., Eds; Academic Press, 2002; Vol. 350, pp. 87-96.

Gruhlke, M. C. H., Schlembach, I., Leontiev, R., Uebachs, A., Gollwitzer, P. U. G., Weiss, A., Delaunay, A., Toledano, M., Slusarenko, A. J. (2017). Yap1p, the central regulator of the *S. cerevisiae* oxidative stress response, is activated by allicin, a natural oxidant and defense substance of garlic. *Free Radical Biology and Medicine,* 108, 793-802. https://doi.org/10.1016/j.freeradbiomed.2017.05.004

Gupta, R. K., Patterson, S. S., Ripp, S., Simpson, M. L., & Sayler, G. S. (2003). Expression of the *Photorhabdus*

*luminescens* lux genes (luxA, B, C, D, and E) in *Saccharomyces cerevisiae. FEMS Yeast Research,* 4(3), 305-313.

Jansen, G.; Wu, C.; Schade, B.; Thomas, D. Y.; Whiteway, M. Drag&Drop cloning in yeast. *Gene* 2005, 344, 43-51, doi:10.1016/j.gene.2004.10.016.

Minskaia, E., Nicholson, J., & Ryan, M. D. (2013). Optimisation of the foot-and-mouth disease virus 2A co-expression system for biomedical applications. *BMC Biotechnology,* 13, 1-11. https://doi.org/10.1186/1472-6750-13-67

Mumberg, D., Müller, R., & Funk, M. (1995). Yeast vectors for the controlled expression of heterologous proteins in different genetic backgrounds. *Gene,* 156 (1), 119-122. https://doi.org/10.1016/0378-1119(95) 00037-7.

Pelletier, J., & Sonenberg, N. (1988). Internal initiation of translation of eukaryotic mRNA directed by a sequence derived from poliovirus RNA. *Nature,* 334(6180), 320-325. https://doi.org/10.1038/334320a0

Xu, T., Young, A., Marr, E., Sayler, G., Ripp, S., & Close, D. (2018). A rapid and reagent-free bioassay for the detection of dioxin-like compounds and other aryl hydrocarbon receptor (AhR) agonists using autobioluminescent yeast. *Analytical and Bioanalytical Chemistry,* 410(4), 1247-1256. https://doi.org/10.1007/s00216-017-0780-1

What is claimed is:

1. A nucleic acid comprising a continuous nucleotide sequence containing:

(i) a gene encoding LuxA, (ii) a gene encoding LuxB, (iii) a gene encoding LuxC, (iv) a gene encoding LuxD, and (v) a gene encoding LuxE, wherein each of the genes is under the control of a yeast, animal, viral or synthetic promoter heterologous to the respective gene, wherein all of the genes together with the promoter are contained in a single nucleotide sequence in a row, wherein the promoters mediate approximately equal expression levels, wherein each gene is followed by a terminator, and/or the nucleic acid does not contain an internal ribosomal entry site and/or self-cutting peptides between any of genes (i) to (vi).

2. The nucleic acid according to claim 1, wherein the gene encoding LuxA and the gene encoding LuxB are from *Photorhabdus luminescens* or *Vibrio harveyi*, (i) wherein LuxA has an amino acid sequence that is at least 70% identical to SEQ ID NO: 1; and/or (ii) wherein LuxB has an amino acid sequence that is at least 70%, identical to SEQ ID NO: 2.

3. The nucleic acid according to claim 1, wherein the genes encoding LuxA (i) and LuxB (ii) are present as a gene luxAB encoding the LuxA/LuxB fusion protein and wherein LuxA and LuxB are connected by a linker.

4. The nucleic acid according to claim 1, wherein LuxC, LuxD and LuxE are from *P. luminescens* (i) wherein LuxC has an amino acid sequence that is at least 70% identical to SEQ ID NO: 3;

(ii) wherein LuxD has an amino acid sequence that is at least 70% identical to SEQ ID NO: 4; and/or (iii) wherein LuxE has an amino acid sequence that is at least 70% identical to SEQ ID NO: 5.

5. The nucleic acid according to claim 1, wherein the nucleic acid additionally comprises (vi) a gene encoding an NADPH flavin oxidoreductase, wherein said NADPH flavin oxidoreductase is frp, from *V. harveyi*, wherein the NADPH-flavin oxidoreductase has an amino acid sequence that is at least 70% identical to SEQ ID NO: 6.

6. The nucleic acid according to claim 1, wherein luxA and luxB or the LuxA/LuxB fusion protein are under the control of a regulatable yeast, animal, viral, or synthetic promoter, wherein the regulatable yeast, animal, viral, or synthetic promoter is regulatable by an environmental influence selected from the group consisting of medicaments, drugs, hormones, environmental toxins, bioavailable compounds and physical influences.

7. The nucleic acid according to claim 1, wherein luxC, luxD, luxE and optionally the NADPH-flavin oxidoreductase are constitutively expressed or under the control of a regulatable yeast, animal viral, or synthetic promoter, wherein the yeast, animal, viral, or synthetic promoter of luxC is the TEF2 promoter, the promoter of luxD is the CDC19 promoter, the promoter of luxE is the ENO2 promoter and/or the promoter of the NADPH-flavin oxidoreductase is the PDC1 promoter.

8. A vector comprising the nucleic acid according to claim 1.

9. A host cell comprising the nucleic acid according to claim 1, wherein the host cell is a yeast selected from the group consisting of *Komagataella phaffii* (*Pichia pastoris*), *Hansenula polymorpha*, *Trichoderma reesei*, *Aspergillus niger*, *Saccharomyces cerevisiae*, *Kluyveromyces lactis*, *Yar-* rowia lipolytica, Pichia methanolica, Candida boidinii, Komagataella spp., Schizosaccharomyces pombe and Blastobotrys adeninivorans.

10. A method of making a host cell, wherein the host cell is a yeast selected from the group consisting of Komagataella phaffii (Pichia pastoris), Hansenula polymorpha, Trichoderma reesei, Aspergillus niger, Saccharomyces cerevisiae, Kluyveromyces lactis, Yarrowia lipolytica, Pichia methanolica, Candida boidinii, Komagataella spp., Schizosaccharomyces pombe and Blastobotrys adeninivorans, said method comprising introducing the nucleic acid according to claim 1 into a host cell.

11. A method for detecting an environmental influence, the method comprising:
   (i) Contacting an environmental sample with the host cell according to claim 9;
   (ii) Determining the luminescence of the host cell,
   wherein luxA and luxB or the LuxA/LuxB fusion protein are optionally under the control of a regulatable promoter that is regulated by the environmental influence and wherein a change in bioluminescence compared to a control sample is indicative of the presence of said environmental influence,
   wherein the environmental influence is selected from the group consisting of medicaments, drugs, hormones, environmental toxins, bioavailable compounds, and physical influences.

12. A biosensor for detecting protein-protein interactions comprising a host cell according to claim 9.

13. A vitality sensor for indicating reduced vitality of a host cell comprising a host cell according to claim 9, wherein reduction or loss of bioluminescence is indicative of reduced vitality of the host cell.

14. A kit comprising the nucleic acid according to claim 1.

15. A host cell comprising the vector according to claim 9, wherein the host cell is a yeast selected from the group consisting of Komagataella phaffii (Pichia pastoris), Hansenula polymorpha, Trichoderma reesei, Aspergillus niger, Saccharomyces cerevisiae, Kluyveromyces lactis, Yarrowia lipolytica, Pichia methanolica, Candida boidinii, Komagataella spp., Schizosaccharomyces pombe and Blastobotrys adeninivorans.

16. A method of making a host cell, wherein the host cell is a yeast, preferably a yeast selected from the group consisting of Komagataella phaffii (Pichia pastoris), Hansenula polymorpha, Trichoderma reesei, Aspergillus niger, Saccharomyces cerevisiae, Kluyveromyces lactis, Yarrowia lipolytica, Pichia methanolica, Candida boidinii, Komagataella spp., Schizosaccharomyces pombe and Blastobotrys adeninivorans, preferably Saccharomyces cerevisiae, said method comprising introducing the vector according to claim 8 into a host cell.

17. A nucleic acid comprising a continuous nucleotide sequence containing:
   (i) a gene encoding LuxA,
   (ii) a gene encoding LuxB,
   (iii) a gene encoding LuxC,
   (iv) a gene encoding LuxD, and
   (v) a gene encoding LuxE,
   wherein each of the genes is under the control of a yeast promoter heterologous to the respective gene, wherein all of the genes together with the promoter are contained in a single nucleotide sequence in a row, wherein promoters mediate approximately equal expression levels, wherein each gene is followed by a terminator, and/or the nucleic acid does not contain an internal ribosomal entry site and/or self-cutting peptides between any of genes (i) to (vi).

\* \* \* \* \*

SEQUENCE LISTING

```
<160> NUMBER OF SEQ ID NOS: 22

<210> SEQ ID NO 1
<211> LENGTH: 359
<212> TYPE: PRT
<213> ORGANISM: Photorhabdus luminescens

<400> SEQUENCE: 1

Met Lys Phe Gly Asn Phe Leu Leu Thr Tyr Gln Pro Pro Gln Phe Ser
1               5                   10                  15

Gln Thr Glu Val Met Lys Arg Leu Val Lys Leu Gly Arg Ile Ser Glu
            20                  25                  30

Glu Cys Gly Phe Asp Thr Val Trp Leu Leu Glu His His Phe Thr Glu
        35                  40                  45

Phe Gly Leu Leu Gly Asn Pro Tyr Val Ala Ala Ala Tyr Leu Leu Gly
    50                  55                  60

Ala Thr Lys Lys Leu Asn Val Gly Thr Ala Ala Ile Val Leu Pro Thr
65                  70                  75                  80

Ala His Pro Val Arg Gln Leu Glu Asp Val Asn Leu Leu Asp Gln Met
                85                  90                  95

Ser Lys Gly Arg Phe Arg Phe Gly Ile Cys Arg Gly Leu Tyr Asn Lys
            100                 105                 110

Asp Phe Arg Val Phe Gly Thr Asp Met Asn Asn Ser Arg Ala Leu Thr
        115                 120                 125

Glu Cys Trp Tyr Gly Leu Ile Lys Asn Gly Met Thr Glu Gly Tyr Met
    130                 135                 140

Glu Ala Asp Asn Glu His Ile Lys Phe His Lys Val Lys Val Asn Pro
145                 150                 155                 160

Thr Ala Tyr Ser Lys Gly Gly Ala Pro Val Tyr Val Val Ala Glu Ser
                165                 170                 175

Ala Ser Thr Thr Glu Trp Ala Ala Gln Phe Gly Leu Pro Met Ile Leu
            180                 185                 190
```

-continued

```
Ser Trp Ile Ile Asn Thr Asn Glu Lys Lys Ala Gln Leu Glu Leu Tyr
        195                 200                 205

Asn Glu Val Ala Gln Glu Tyr Gly His Asp Ile His Asn Ile Asp His
        210                 215                 220

Cys Leu Ser Tyr Ile Thr Ser Val Asn Tyr Asp Ser Asn Lys Ala Gln
225                 230                 235                 240

Glu Ile Cys Arg Asp Phe Leu Gly His Trp Tyr Asp Ser Tyr Val Asn
                245                 250                 255

Ala Thr Thr Ile Phe Asp Asp Ser Asp Lys Thr Arg Gly Tyr Asp Phe
                260                 265                 270

Asn Lys Gly Gln Trp Arg Asp Phe Val Leu Lys Gly His Arg Asp Thr
        275                 280                 285

Asn Arg Arg Ile Asp Tyr Ser Tyr Glu Ile Asn Pro Val Gly Thr Pro
        290                 295                 300

Gln Glu Cys Ile Asp Ile Ile Gln Lys Asp Ile Asp Ala Thr Gly Ile
305                 310                 315                 320

Ser Asn Ile Cys Cys Gly Phe Glu Ala Asn Gly Thr Val Asp Glu Ile
                325                 330                 335

Ile Ala Ser Met Lys Leu Phe Gln Ser Asp Val Met Pro Phe Leu Lys
                340                 345                 350

Glu Lys Gln Arg Ser Leu Leu
        355
```

```
<210> SEQ ID NO 2
<211> LENGTH: 324
<212> TYPE: PRT
<213> ORGANISM: Photorhabdus luminescens

<400> SEQUENCE: 2

Met Lys Phe Gly Leu Phe Phe Leu Asn Phe Ile Asn Ser Thr Thr Val
1                 5                   10                  15

Gln Glu Gln Ser Ile Val Arg Met Gln Glu Ile Thr Glu Tyr Val Asp
        20                  25                  30

Lys Leu Asn Phe Glu Gln Ile Leu Val Tyr Glu Asn His Phe Ser Gly
        35                  40                  45

Asn Gly Val Val Gly Ala Pro Leu Thr Val Ser Gly Phe Leu Leu Gly
        50                  55                  60

Leu Thr Glu Lys Ile Lys Ile Gly Ser Leu Asn His Ile Ile Thr Thr
65                  70                  75                  80

His His Pro Val Arg Ile Ala Glu Glu Ala Cys Leu Leu Asp Gln Leu
                85                  90                  95

Ser Glu Gly Arg Phe Ile Leu Gly Phe Ser Asp Cys Glu Lys Lys Asp
        100                 105                 110

Glu Met Arg Leu Phe Asn Arg Pro Val Glu Tyr Gln Gln Gln Leu Phe
        115                 120                 125

Glu Glu Cys Tyr Glu Ile Ile Asn Asp Ala Leu Thr Thr Gly Tyr Cys
        130                 135                 140

Asn Pro Asp Asn Asp Phe Tyr Ser Phe Pro Lys Ile Ser Val Asn Pro
145                 150                 155                 160

His Ala Tyr Thr Gln Gly Gly Pro Arg Arg Tyr Val Thr Ala Thr Ser
                165                 170                 175

His His Ile Val Glu Trp Ala Ala Lys Lys Gly Ile Pro Leu Ile Phe
                180                 185                 190

Lys Trp Asp Asp Ser Asn Asp Val Arg Tyr Glu Tyr Ala Glu Arg Tyr
```

-continued

```
            195                 200                 205
Lys Ala Val Ala Asp Lys Tyr Gly Ile Asp Leu Ser Ala Ile Asp His
    210                 215                 220
Gln Leu Met Val Leu Val Asn Tyr Asn Glu Asp Ser His Lys Ala Lys
225                 230                 235                 240
Gln Glu Thr Arg Ala Phe Ile Arg Asp Tyr Val Leu Glu Met Tyr Pro
                245                 250                 255
Asn Glu Asn Leu Glu Asn Lys Leu Glu Glu Ile Ile Thr Glu Asn Ala
                260                 265                 270
Val Gly Asp Tyr Thr Glu Cys Ile Ala Ala Ala Lys Leu Ala Ile Glu
                275                 280                 285
Lys Cys Gly Ala Lys Ser Val Leu Leu Ser Phe Glu Pro Met Asn Asp
    290                 295                 300
Leu Met His Gln Lys Asn Val Ile Asn Ile Val Asn Asp Asn Ile Lys
305                 310                 315                 320
Lys Tyr His Met

<210> SEQ ID NO 3
<211> LENGTH: 480
<212> TYPE: PRT
<213> ORGANISM: Photorhabdus luminescens

<400> SEQUENCE: 3

Met Thr Lys Lys Ile Ser Phe Ile Ile Asn Gly Gln Val Glu Ile Phe
1               5                   10                  15
Pro Glu Ser Asp Asp Leu Val Gln Ser Ile Asn Phe Gly Asp Asn Ser
                20                  25                  30
Val Tyr Leu Pro Ile Leu Asn Asn Ser His Val Lys Asn Ile Ile Asp
            35                  40                  45
Tyr Asn Glu Asn Asn Lys Leu Arg Leu His Asn Ile Val Asn Phe Leu
    50                  55                  60
Tyr Thr Val Gly Gln Arg Trp Lys Asn Glu Glu Tyr Ser Arg Arg Arg
65                  70                  75                  80
Thr Tyr Ile Arg Asp Leu Lys Lys Tyr Met Gly Tyr Ser Glu Ala Met
                85                  90                  95
Ala Lys Leu Glu Ala Asn Trp Ile Ser Met Ile Leu Cys Ser Lys Gly
            100                 105                 110
Gly Leu Tyr Asp Val Val Glu Asn Glu Leu Gly Ser Arg His Ile Met
            115                 120                 125
Asp Glu Trp Leu Pro Gln Asp Glu Ser Tyr Ile Lys Ala Phe Pro Lys
    130                 135                 140
Gly Lys Ser Ile His Leu Leu Ala Gly Asn Val Pro Leu Ser Gly Ile
145                 150                 155                 160
Met Ser Ile Leu Arg Ala Ile Leu Thr Lys Asn Gln Cys Ile Ile Lys
                165                 170                 175
Thr Ser Ser Thr Asp Pro Phe Thr Ala Asn Ala Leu Ala Leu Ser Phe
            180                 185                 190
Ile Asp Val Asp Pro Asn His Pro Ile Thr Arg Ser Leu Ser Val Val
            195                 200                 205
Tyr Trp Pro His Gln Gly Asp Thr Ser Leu Ala Lys Glu Ile Met Gln
    210                 215                 220
His Met Asp Val Ile Val Ala Trp Gly Gly Glu Asp Ala Ile Asn Trp
225                 230                 235                 240
Ala Val Glu His Ala Pro Pro Tyr Ala Asp Val Ile Lys Phe Gly Ser
```

```
                    245             250             255

Lys Lys Ser Phe Cys Ile Ile Asp Asn Pro Val Asp Leu Thr Ser Ala
            260             265             270

Ala Thr Gly Ala Ala His Asp Ile Cys Phe Tyr Asp Gln Arg Ala Cys
            275             280             285

Phe Ser Ala Gln Asn Ile Tyr Tyr Met Gly Asn Gln Tyr Glu Glu Phe
            290             295             300

Lys Leu Ala Leu Ile Glu Lys Leu Asn Leu Tyr Ala His Ile Leu Pro
305             310             315             320

Asn Ala Lys Lys Asp Phe Asp Glu Lys Ala Ala Tyr Ser Leu Val Gln
            325             330             335

Lys Glu Ser Leu Phe Ala Gly Leu Lys Val Glu Val Asp Val His Gln
            340             345             350

Arg Trp Met Ile Ile Glu Ser Asn Ala Gly Val Glu Phe Asn Gln Pro
            355             360             365

Leu Gly Arg Cys Val Tyr Leu His His Val Asp Asn Ile Glu Gln Val
            370             375             380

Leu Pro Tyr Val Gln Lys Asn Lys Thr Gln Thr Ile Ser Ile Phe Pro
385             390             395             400

Trp Glu Ser Ala Phe Lys Tyr Arg Asp Ala Leu Ala Leu Arg Gly Ala
                405             410             415

Glu Arg Ile Val Glu Ala Gly Met Asn Asn Ile Phe Arg Val Gly Gly
            420             425             430

Ser His Asp Gly Met Arg Pro Leu Gln Arg Leu Val Thr Tyr Ile Ser
            435             440             445

His Glu Arg Pro Ser His Tyr Thr Ala Lys Asp Val Ala Val Glu Ile
        450             455             460

Glu Gln Thr Arg Phe Leu Glu Glu Asp Lys Phe Leu Val Phe Val Pro
465             470             475             480

<210> SEQ ID NO 4
<211> LENGTH: 307
<212> TYPE: PRT
<213> ORGANISM: Photorhabdus luminescens

<400> SEQUENCE: 4

Met Glu Asn Lys Ser Lys Tyr Lys Thr Ile Asp His Val Leu Cys Val
1               5               10              15

Glu Gly Asn Lys Lys Ile His Val Trp Glu Thr Leu Pro Glu Glu Asn
            20              25              30

Ser Pro Lys Arg Lys Asn Thr Ile Ile Ile Ala Ser Gly Phe Ala Arg
            35              40              45

Arg Met Asp His Phe Ala Gly Leu Ala Glu Tyr Leu Ser Arg Asn Gly
        50              55              60

Phe His Val Ile Arg Tyr Asp Ser Leu His His Val Gly Leu Ser Ser
65              70              75              80

Gly Thr Ile Asp Glu Phe Thr Met Ser Ile Gly Lys Gln Ser Leu Leu
                85              90              95

Ala Val Val Asp Trp Leu Asn Thr Arg Lys Ile Asn Asn Arg Gly Ile
            100             105             110

Leu Ala Ser Ser Leu Ser Ala Arg Ile Val Tyr Ala Ser Leu Ser Glu
            115             120             125

Ile Asn Val Ser Phe Leu Ile Thr Ala Val Gly Val Val Asn Leu Arg
        130             135             140
```

-continued

```
Tyr Thr Leu Glu Arg Ala Leu Gly Phe Asp Tyr Leu Ser Leu Pro Ile
145                 150                 155                 160

Asn Glu Leu Pro Asn Asn Leu Asp Phe Glu Gly His Lys Leu Gly Ala
                165                 170                 175

Glu Val Phe Ala Arg Asp Cys Leu Asp Phe Gly Trp Glu Asp Leu Thr
                180                 185                 190

Ser Thr Ile Asn Ser Met Met Tyr Leu Asp Ile Pro Phe Ile Ala Phe
                195                 200                 205

Thr Ala Asn Asn Asp Asn Trp Val Lys Gln Asp Glu Val Ile Thr Leu
                210                 215                 220

Leu Ser Asn Ile Arg Ser Asn Arg Cys Lys Ile Tyr Ser Leu Leu Gly
225                 230                 235                 240

Ser Ser His Asp Leu Gly Glu Asn Leu Val Val Leu Arg Asn Phe Tyr
                245                 250                 255

Gln Ser Val Thr Lys Ala Ala Ile Ala Met Asp Asn Asp Arg Leu Asp
                260                 265                 270

Ile Asp Val Asp Ile Ile Glu Pro Ser Phe Glu His Leu Thr Ile Ala
                275                 280                 285

Thr Val Asn Glu Arg Arg Met Lys Ile Glu Ile Glu Asn Gln Ala Ile
                290                 295                 300

Ser Leu Ser
305
```

```
<210> SEQ ID NO 5
<211> LENGTH: 370
<212> TYPE: PRT
<213> ORGANISM: Photorhabdus luminescens

<400> SEQUENCE: 5

Met Thr Ser Tyr Val Asp Lys Gln Glu Ile Ile Ala Ser Ser Glu Ile
1                   5                   10                  15

Asp Asp Leu Ile Phe Ser Ser Asp Pro Leu Ala Trp Ser Tyr Asp Glu
                20                  25                  30

Gln Glu Lys Ile Arg Asn Lys Phe Val Leu Asp Ala Phe Arg Asn His
                35                  40                  45

Tyr Lys His Cys Gln Glu Tyr Arg His Tyr Cys Gln Val His Lys Val
                50                  55                  60

Asp Asp Asn Ile Thr Glu Ile Asp Asp Ile Pro Val Phe Pro Thr Ser
65                  70                  75                  80

Val Phe Lys Phe Thr Arg Leu Leu Thr Ser Gln Glu Asn Glu Ile Glu
                85                  90                  95

Ser Trp Phe Thr Ser Ser Gly Thr Ser Gly Leu Lys Ser Gln Val Ala
                100                 105                 110

Arg Asn Arg Leu Ser Ile Glu Arg Leu Leu Gly Ser Val Ser Tyr Gly
                115                 120                 125

Met Lys Tyr Val Gly Ser Trp Phe Asp His Gln Ile Glu Leu Val Asn
                130                 135                 140

Leu Gly Pro Asp Arg Phe Asn Ala His Asn Ile Trp Phe Lys Tyr Val
145                 150                 155                 160

Met Ser Leu Val Glu Leu Leu Tyr Pro Thr Thr Phe Thr Val Met Glu
                165                 170                 175

Glu Arg Ile Asp Phe Val Lys Thr Leu Asn Ser Leu Glu Arg Ile Lys
                180                 185                 190

Asn Gln Gly Lys Asp Ile Cys Leu Ile Gly Ser Pro Tyr Phe Ile Tyr
                195                 200                 205
```

```
Leu Leu Cys Gln Tyr Met Lys Asp Lys Asn Ile Ser Phe Tyr Gly Asp
    210             215             220

Lys Asn Leu Tyr Ile Ile Thr Gly Gly Gly Trp Lys Ser Tyr Glu Lys
225             230             235             240

Glu Ser Leu Lys Arg Asp Asp Phe Asn His Leu Leu Phe Asp Thr Phe
                245             250             255

Asn Leu Asn Asn Ile Ser Gln Ile Arg Asp Ile Phe Asn Gln Val Glu
                260             265             270

Leu Asn Thr Cys Phe Phe Glu Asp Glu Met Gln Arg Lys Arg Val Pro
            275             280             285

Pro Trp Val Tyr Ala Arg Ala Leu Asp Pro Glu Thr Leu Lys Pro Val
    290             295             300

Pro Asp Gly Met Pro Gly Leu Met Ser Tyr Met Asp Ala Ser Ser Thr
305             310             315             320

Ser Tyr Pro Ala Phe Ile Val Thr Asp Asp Val Gly Ile Met Ser Arg
                325             330             335

Glu Tyr Gly Gln Tyr Pro Gly Val Leu Val Glu Ile Leu Arg Arg Val
                340             345             350

Asn Thr Arg Ala Gln Lys Gly Cys Ala Leu Ser Leu Asn Gln Ala Phe
            355             360             365

Asn Ser
    370

<210> SEQ ID NO 6
<211> LENGTH: 240
<212> TYPE: PRT
<213> ORGANISM: Vibrio harveyi

<400> SEQUENCE: 6

Met Asn Asn Thr Ile Glu Thr Ile Leu Ala His Arg Ser Ile Arg Lys
1               5               10              15

Phe Thr Ala Val Pro Ile Thr Asp Glu Gln Arg Gln Thr Ile Ile Gln
                20              25              30

Ala Gly Leu Ala Ala Ser Ser Ser Ser Met Leu Gln Val Val Ser Ile
            35              40              45

Val Arg Val Thr Asp Ser Glu Lys Arg Asn Glu Leu Ala Gln Phe Ala
    50              55              60

Gly Asn Gln Ala Tyr Val Glu Ser Ala Ala Glu Phe Leu Val Phe Cys
65              70              75              80

Ile Asp Tyr Gln Arg His Ala Thr Ile Asn Pro Asp Val Gln Ala Asp
                85              90              95

Phe Thr Glu Leu Thr Leu Ile Gly Ala Val Asp Ser Gly Ile Met Ala
            100             105             110

Gln Asn Cys Leu Leu Ala Ala Glu Ser Met Gly Leu Gly Gly Val Tyr
        115             120             125

Ile Gly Gly Leu Arg Asn Ser Ala Ala Gln Val Asp Glu Leu Leu Gly
    130             135             140

Leu Pro Glu Asn Ser Ala Val Leu Phe Gly Met Cys Leu Gly His Pro
145             150             155             160

Asp Gln Asn Pro Glu Val Lys Pro Arg Leu Pro Ala His Val Val Val
                165             170             175

His Glu Asn Gln Tyr Gln Glu Leu Asn Leu Asp Asp Ile Gln Ser Tyr
            180             185             190

Asp Gln Thr Met Gln Ala Tyr Tyr Ala Ser Arg Thr Ser Asn Gln Lys
```

```
           195              200              205
Leu Ser Thr Trp Ser Gln Glu Val Thr Gly Lys Leu Ala Gly Glu Ser
    210              215              220

Arg Pro His Ile Leu Pro Tyr Leu Asn Ser Lys Gly Leu Ala Lys Arg
225              230              235              240

<210> SEQ ID NO 7
<211> LENGTH: 17565
<212> TYPE: DNA
<213> ORGANISM: Artificial
<220> FEATURE:
<223> OTHER INFORMATION: pRS426-URA3-Lux-Plasmid

<400> SEQUENCE: 7
gacgaaaggg cctcgtgata cgcctatttt tataggttaa tgtcatgata ataatggttt      60
cttagtatga tccaatatca aaggaaatga tagcattgaa ggatgagact aatccaattg     120
aggagtggca gcatatagaa cagctaaagg gtagtgctga aggaagcata cgatacctcg     180
catggaatgg gataatatca caggaggtac tagactacct ttcatcctac ataaatagac     240
gcatataagt acgcatttaa gcataaacac gcactatgcc gttcttctca tgtatatata     300
tatacaggca acacgcagat ataggtgcga cgtgaacagt gagctgtatg tgcgcagctc     360
gcgttgcatt ttcggaagcg ctcgttttcg gaaacgcttt gaagttccta ttccgaagtt     420
cctattctct agaaagtata ggaacttcag agcgcttttg aaaaccaaaa gcgctctgaa     480
gacgcacttt caaaaaacca aaaacgcacc ggactgtaac gagctactaa aatattgcga     540
ataccgcttc cacaaacatt gctcaaaagt atctctttgc tatatatctc tgtgctatat     600
ccctatataa cctacccatc caccttttcgc tccttgaact tgcatctaaa ctcgacctct     660
acatttttta tgtttatctc tagtattact ctttagacaa aaaaattgta gtaagaacta     720
ttcatagagt gaatcgaaaa caatacgaaa atgtaaacat ttcctatacg tagtatatag     780
agacaaaata gaagaaaccg ttcataattt tctgaccaat gaagaatcat caacgctatc     840
actttctgtt cacaaagtat gcgcaatcca catcggtata gaatataatc ggggatgcct     900
ttatcttgaa aaaatgcacc cgcagcttcg ctagtaatca gtaaacgcgg gaagtggagt     960
caggcttttt ttatggaaga gaaaatagac accaaagtag ccttcttcta accttaacgg    1020
acctacagtg caaaaagtta tcaagagact gcattataga gcgcacaaag gagaaaaaaa    1080
gtaatctaag atgctttgtt agaaaaatag cgctctcggg atgcattttt gtagaacaaa    1140
aaagaagtat agattctttg ttggtaaaat agcgctctcg cgttgcattt ctgttctgta    1200
aaaatgcagc tcagattctt tgtttgaaaa attagcgctc tcgcgttgca ttttttgtttt    1260 acaaaaatga agcacagatt cttcgttggt aaaatagcgc tttcgcgttg catttctgtt    1320
ctgtaaaaat gcagctcaga ttctttgttt gaaaaattag cgctctcgcg ttgcattttt    1380
gttctacaaa atgaagcaca gatgcttcgt tcaggtggca ctttctcgggg aaatgtgcgc    1440 ggaaccccta tttgtttatt tttctaaata cattcaaata tgtatccgct catgagacaa    1500
taaccctgat aaatgcttca ataatattga aaaaggaaga gtatgagtat tcaacatttc    1560
cgtgtcgccc ttattccctt ttttgcggca ttttgccttc ctgttttttgc tcacccagaa    1620 acgctggtga aagtaaaaga tgctgaagat cagttgggtg cacgagtggg ttacatcgaa    1680
ctggatctca acagcggtaa gatccttgag agttttcgcc ccgaagaacg ttttccaatg    1740
atgagcactt ttaaagttct gctatgtggc gcggtattat cccgtattga cgccgggcaa    1800
gagcaactcg gtcgccgcat acactattct cagaatgact tggttgagta ctcaccagtc    1860
```

-continued

```
acagaaaagc atcttacgga tggcatgaca gtaagagaat tatgcagtgc tgccataacc   1920
atgagtgata acactgcggc caacttactt ctgacaacga tcggaggacc gaaggagcta   1980
accgcttttt tgcacaacat gggggatcat gtaactcgcc ttgatcgttg ggaaccggag   2040
ctgaatgaag ccataccaaa cgacgagcgt gacaccacga tgcctgtagc aatggcaaca   2100
acgttgcgca aactattaac tggcgaacta cttactctag cttcccggca acaattaata   2160
gactggatgg aggcggataa agttgcagga ccacttctgc gctcggccct tccggctggc   2220
tggtttattg ctgataaatc tggagccggt gagcgtgggt ctcgcggtat cattgcagca   2280
ctggggccag atggtaagcc ctcccgtatc gtagttatct acacgacggg gagtcaggca   2340
actatggatg aacgaaatag acagatcgct gagataggtg cctcactgat taagcattgg   2400
taactgtcag accaagttta ctcatatata ctttagattg atttaaaact tcattttttaa   2460 tttaaaagga tctaggtgaa gatccttttt gataatctca tgaccaaaat cccttaacgt   2520
gagttttcgt tccactgagc gtcagacccc gtagaaaaga tcaaaggatc ttcttgagat   2580
cctttttttc tgcgcgtaat ctgctgcttg caaacaaaaa aaccaccgct accagcggtg   2640
gtttgtttgc cggatcaaga gctaccaact ctttttccga aggtaactgg cttcagcaga   2700
gcgcagatac caaatactgt ccttctagtg tagccgtagt taggccacca cttcaagaac   2760
tctgtagcac cgcctacata cctcgctctg ctaatcctgt taccagtggc tgctgccagt   2820
ggcgataagt cgtgtcttac cgggttggac tcaagacgat agttaccgga taaggcgcag   2880
cggtcgggct gaacggggg ttcgtgcaca gcccagct tggagcgaac gacctacacc   2940
gaactgagat acctacagcg tgagctatga aaagcgcca cgcttcccga agggagaaag   3000
gcggacaggt atccggtaag cggcagggtc ggaacaggag agcgcacgag ggagcttcca   3060
gggggaaacg cctggtatct ttatagtcct gtcgggtttc gccacctctg acttgagcgt   3120
cgatttttgt gatgctcgtc aggggggcgg agcctatgga aaaacgccag caacgcggcc   3180
tttttacggt tcctggcctt ttgctggcct tttgctcaca tgttctttcc tgcgttatcc   3240
cctgattctg tggataaccg tattaccgcc tttgagtgag ctgataccgc tcgccgcagc   3300
cgaacgaccg agcgcagcga gtcagtgagc gaggaagcgg aagagcgccc aatacgcaaa   3360
ccgcctctcc ccgcgcgttg gccgattcat taatgcagct ggcacgacag gtttcccgac   3420
tggaaagcgg gcagtgagcg caacgcaatt aatgtgagtt acctcactca ttaggcaccc   3480
caggctttac actttatgct tccggctcct atgttgtgtg gaattgtgag cggataacaa   3540
tttcacacag gaaacagcta tgaccatgat tacgccaagc gcgcaattaa ccctcactaa   3600
agggaacaaa agctggagct ggggccgtat acttacatat agtagatgtc aagcgtaggc   3660 gcttccctg ccggctgtga gggcgccata accaaggtat ctatagaccg ccaatcagca   3720
aactacctcc gtacattcat gttgcaccca cacatttata cacccagacc gcgacaaatt   3780
acccataagg ttgtttgtga cggcgtcgta caagagaacg tgggaacttt ttaggctcac   3840
caaaaaagaa agaaaaaata cgagttgctg acagaagcct caagaaaaaa aaaattcttc   3900
ttcgactatg ctggaggcag agatgatcga gccggtagtt aactatatat agctaaattg   3960
gttccatcac cttcttttct ggtgtcgctc cttctagtgc tatttctggc ttttcctatt   4020
tttttttttc cattttttctt tctctctttc taatatataa attctcttgc attttctatt   4080
tttctctcta tctattctac ttgtttattc ccttcaaggt ttttttttaa ggagtacttg   4140
tttttagaat atacggtcaa cgaactataa ttaactaaac atgactaaaa aaatttcatt   4200
```

```
cattattaac ggccaggttg aaatttttcc cgaaagtgat gatttagtgc aatccattaa      4260
ttttggtgat aatagtgttt acctgccaat attgaataat tctcatgtaa aaaacattat      4320
tgattataat gaaaataata aattacggtt gcataatatt gtcaattttc tctatacggt      4380
agggcaaaga tggaaaaatg aagaatattc aagacgcagg acatacattc gtgatttaaa      4440
aaaatatatg ggatattcag aagcaatggc caagttagag gccaactgga tatctatgat      4500
tttatgttct aaaggtggcc tttatgatgt tgtagaaaat gaacttggtt ctcgccatat      4560
catggatgaa tggctacctc aggatgaaag ttatattaag gcttttccga aaggtaagtc      4620
tatacatctg ttggcaggta atgttccatt atctgggatc atgtctatat tacgcgcaat      4680
tttaaccaag aatcagtgta ttataaaaac atcgtcaacc gatcccttta ccgctaatgc      4740
attagcgtta agctttatcg atgtagaccc taatcatccg ataacgcgct ctttgtctgt      4800
tgtatattgg ccacaccaag gtgatacatc actcgcaaaa gaaattatgc aacatatgga      4860
tgttattgtc gcttggggag gggaagatgc gattaattgg gctgtagaac atgcaccacc      4920
ctatgctgac gtgattaaat ttggctctaa aaagagtttt tgcattattg ataatccagt      4980
tgatttaacg tcagcagcta ccggtgcggc tcatgatatt tgttttttacg atcagcgcgc      5040 ttgttttttct gcccaaaaca tatattacat gggaaatcag tatgaggaat ttaagttagc      5100
gttgatagaa aaacttaatc tatatgcgca tatattacca aacgccaaaa aagattttga      5160
tgaaaaggcg gcctattctt tagtccaaaa agagagctta tttgctggat taaaagtaga      5220
ggtggatgtt catcaacgtt ggatgattat tgagtcaaat gcgggtgtgg aatttaatca      5280
accacttggc agatgtgtgt atcttcatca cgtcgataat attgagcaag tattgcctta      5340
tgttcaaaaa aataagacac aaaccatatc tattttttcct tgggaatccg catttaagta      5400
tcgagatgcg ttggcattaa gaggtgcgga aaggattgta gaagcaggaa tgaataatat      5460
atttcgagtt ggtggatctc atgacggaat gaggccgtta caacgattag tgacatatat      5520
ttctcatgag aggccatctc attatactgc taaggatgtt gcggttgaaa tagaacagac      5580
tcgattcctg gaagaagata agttccttgt atttgtcccg taagagtaat aattattgct      5640
tccatataat attttttatat acctcttatt tttatgtatt agttaattaa gtattttttat      5700 ctatctgctt atcattttct tttcatatag ggggggttgg tgttttcttg cccatcagat      5760
tgatgtcctc caactcggca ctattttaca aagggttttt ttgtaagaga aggagaagac      5820
agatactaaa ccatacgtta ctcgaaacaa aaaaaaaaaa aatggaaaaa gctgctatca      5880 acaaagacg gcctcatcaa acctaaagaa accatgtcag cgtatgtata taccttgtaa       5940
tttacgtttc cttaaatctt ctttctacta acgtttttcat tattctatac tctatgacca      6000
ataaaaacag actgtacttt caaaatttac ccagtaggcc agcaaataaa gaaaattata      6060
ccagattact tctgaaacac attaatccca acaacaagta tgccattaat ccgtcgctac      6120
cccaatgcta gtattttgga gattaatctc agtacaaaac aatattaaaa agaggtgaat      6180 tattttttccc ccccttatttt ttttttgtta gaattgatcc aaatgtaaat aaacaatcac      6240
aaggaaaaaa aaaaaaaaaa aaaaatagc cgccatgacc ccggatcgtc ggttgtgata      6300
cggtcagggt agcgccctgg tcaaacttca gaactaaaaa aataataagg aagaaaaaaa      6360
tagctaattt ttccggcaga agatttttcg ctacccgaaa gttttttccgg caagctaaat      6420 ggaaaaagga aagattattg aaagagaaag aaagaaaaaa aaaaaatgta cacccagaca      6480
tcgggcttcc acaatttcgg ctctattgtt ttccatctct cgcaacggcg ggattcctct      6540
atggcgtgtg atgtctgtat ctgttactta atccagaaac tggcacttga cccaactctg      6600
```

-continued

```
ccacgtgggt cgttttgcca tcgacagatt gggagatttt catagtagaa ttcagcatga    6660
tagctacgta aatgtgttcc gcaccgtcac aaagtgtttt ctactgttct ttcttctttc    6720
gttcattcag ttgagttgag tgagtgcttt gttcaatgga tcttagctaa aatgcatatt    6780 tttctcttg gtaaatgaat gcttgtgatg tcttccaagt gatttccttt ccttcccata    6840
tgatgctagg tacctttagt gtcttcctaa aaaaaaaaa aggctcgcca tcaaaacgat    6900
attcgttggc tttttttct gaattataaa tactctttgg taacttttca tttccaagaa    6960 cctcttttt ccagttatat catggtcccc tttcaaagtt attctctact cttttcata    7020 ttcattcttt ttcatccttt ggtttttat tcttaacttg tttattattc tctcttgttt    7080
ctatttacaa gacaccaatc aaaacaaata aacatcatc acaatggaaa ataaatccaa    7140
atataaaacc atcgaccatg ttctttgtgt tgaaggaaat aaaaaaattc atgtttggga    7200
aacgctgcca gaagaaaaca gcccaaagag aaagaatacc attattattg cgtcgggttt    7260
tgcccgaagg atggatcatt ttgctggttt agcggaatat ttatcgcgga atgggtttca    7320
tgtgattcgc tatgattcac ttcaccacgt tgggttgagt tcaggacaa ttgatgaatt    7380 tacaatgtct ataggaaaac agagcctatt agccgtggtt gattggttaa atacacgaaa    7440
aataaataac cgtggtattt tggcttcaag cttatctgca cggatagttt atgcaagtct    7500
atctgaaatt aatgtttcat tttaatcac cgcagtcggt gttgttaact taagatatac    7560
gcttgaaaga gctttaggat ttgattatct cagtttaccc attaatgaat tgccgaataa    7620
tttggatttt gaaggccata aattgggtgc tgaagtcttt gcgagagatt gccttgattt    7680
tggctgggaa gatttaactt ctacaatcaa tagcatgatg tatcttgata taccgtttat    7740
tgcttttact gcaaataacg acaattgggt aaagcaagat gaagttatca cattgttatc    7800
aaatattcgt agtaatcgat gcaagatata ttctttgcta gggagttcgc atgacttggg    7860
tgaaaactta gtggtcctgc gcaattttta tcaatcggtt acgaaggctg ctatcgcgat    7920
ggataatgat cgtctggata ttgatgttga tattattgaa ccatcattcg aacatctaac    7980
tattgcgaca gtcaatgaac gtcgaatgaa aattgagatt gaaaatcaag cgatttcgct    8040
gtcttaaaaa aagaatcatg attgaatgaa gatattattt ttttgaatta tattttttaa    8100
attttatata aagacatggt ttttcttttc aactcaaata aagatttata agttacttaa    8160
ataacataca ttttataagg tattctataa aaagagtatt atgttattgt taacctttt    8220 gtctccaatt gtcgtcataa cgatgaggtg ttgcattttt ggaaacgaga ttgacataga    8280
gtcaaaattt gctaaatttg atccctccca tcgcaagata atcttccctc aaggttatca    8340
tgattatcag gatggcgaaa ggatacgcta aaaattcaat aaaaaattca atataatttt    8400
cgtttcccaa gaactaactt ggaaggttat acatgggtac ataaatgcgt gtcgacgctg    8460
cgggtataga aagggttctt tactctatag tacctcctcg ctcagcatct gcttcttccc    8520
aaagatgaac gcggcgttat gtcactaacg acgtgcacca acttgcggaa agtggaatcc    8580
cgttccaaaa ctggcatcca ctaattgata catctacaca ccgcacgcct tttttctgaa    8640
gcccactttc gtggactttg ccatatgcaa aattcatgaa gtgtgatacc aagtcagcat    8700
acacctcact agggtagttt ctttggttgt attgatcatt tggttcatcg tggttcatta    8760 atttttttc tccattgctt tctggctttg atcttactat catttggatt tttgtcgaag    8820
gttgtagaat tgtatgtgac aagtggcacc aagcatatat aaaaaaaaa agcattatct    8880 tcctaccaga gttgattgtt aaaaacgtat ttatagcaaa cgcaattgta attaattctt    8940
```

-continued

```
attttgtatc ttttcttccc ttgtctcaat cttttatttt tattttattt ttcttttctt    9000
agtttctttc ataacaccaa gcaactaata ctataacata caataataat gacttcatat    9060
gttgataaac aagagatcat agcaagctca gaaattgatg atttgatttt ttccagcgat    9120
ccattagctt ggtcttacga tgaacaggaa aaaatcagaa acaaatttgt tcttgatgca    9180
tttcgtaatc actataaaca ttgtcaagaa taccgtcact actgtcaggt acacaaagta    9240
gacgacaata ttacggaaat tgatgacata cctgtattcc caacatcagt tttttaagttt   9300 actcgcttat taacttctca ggagaacgag attgaaagtt ggtttaccag cagcggcacg    9360
agtggtttaa aaagtcaggt ggcgcgtaac agactaagta ttgagagact cttaggctct    9420
gtgagttatg gcatgaaata tgttggtagt tggtttgatc atcaaataga gttggtcaac    9480
ttagggccag atagatttaa tgctcataac atttggttta aatatgttat gagcttggta    9540
gaattattat atcccacgac atttaccgta atggaagaac gaatagattt tgttaagaca    9600
ttgaatagcc ttgagcgaat aaaaaatcaa ggaaaagata tttgtcttat cggctcacca    9660
tactttattt atttgctctg ccagtatatg aaagataaaa atatctcatt ttatggggat    9720
aaaaaccttt atatcataac ggggggcggc tggaaaagtt atgaaaaaga gtccctaaaa    9780
cgcgatgatt tcaatcatct tttattcgac acgttcaacc tcaataatat tagtcaaatc    9840
cgcgatatat ttaatcaagt tgaactcaac acttgtttct ttgaggatga aatgcaacgt    9900
aaacgtgttc cgccgtgggt atatgcgcga gcacttgatc ctgaaacatt gaaacctgta    9960
cctgatggaa tgccgggttt gatgagttat atggatgcgt catcaacgag ttatccggca    10020
tttattgtta ccgatgatgt cgggataatg agcagagaat atggtcaata tcctggtgta    10080
cttgttgaga ttttacgtcg cgtcaatacg agggcacaga aagggtgtgc tttaagctta    10140
aaccaagcat ttaatagttg aagtgctttt aactaagaat tattagtctt ttctgcttat    10200
tttttcatca tagtttagaa cactttatat taacgaatag tttatgaatc tatttaggtt    10260
taaaaattga tacagttta taagttactt tttcaaagac tcgtgctgtc tattgcataa     10320
tgcactggaa ggggaaaaaa aaggtgcaca cgcgtggctt tttcttgaat ttgcagtttg    10380
aaaaataact acatggatga taagaaaaca tggagtacag tcactttgag aaccttcaat    10440
cagctggtaa cgtcttcgtt aattggatac tcaaaaaaga tggatagcat gaatcacaag    10500
atggaaggaa atgcgggcca cgaccacagt gatatgcata tgggagatgg agatgatacc    10560
tcatgcgact gggtgagcat atgttccgct gatgtgatgt gcaagataaa caagcaaggc    10620
agaaactaac ttcttcttca tgtaataaac acaccccgcg tttatttacc tatctctaaa    10680
cttcaacacc ttatatcata actaatattt cttgagataa gcacactgca cccatacctt    10740
ccttaaaaac gtagcttcca gtttttggtg gttccggctt ccttcccgat tccgcccgct    10800
aaacgcatat ttttgttgcc tggtggcatt tgcaaaatgc ataacctatg catttaaaag    10860
attatgtatg ctcttctgac ttttcgtgtg atgaggctcg tggaaaaaat gaataattta    10920
tgaatttgag aacaattttg tgttgttacg gtattttact atggaataat caatcaattg    10980
aggattttat gcaaatatcg tttgaatatt tttccgaccc tttgagtact tttcttcata    11040
attgcataat attgtccgct gcccctttt ctgttagacg gtgtcttgat ctacttgcta     11100
tcgttcaaca ccaccttatt ttctaactat ttttttttta gctcatttga atcagcttat    11160
ggtgatggca catttttgca taaacctagc tgtcctcgtt gaacatagga aaaaaaaata    11220
tataaacaag gctctttcac tctccttgca atcagatttg ggtttgttcc ctttatttc     11280 atatttcttg tcatattcct ttctcaatta ttattttcta ctcataacct cacgcaaaat    11340
```

-continued

```
aacacagtca aatcaatcaa aatgaacaat acgattgaaa ccattcttgc tcatcgctct    11400
atccgaaaat tcaccgcagt tcctattact gatgaacaaa gacaaaccat cattcaagca    11460
ggtttagctg cgtcttcttc tagtatgctt caagtcgtct caatcgttcg agtgactgac    11520
tctgaaaagc gtaacgaatt ggctcaattt gctggtaacc aagcttatgt tgaaagtgcg    11580
gctgagttct tagtgttttg tattgattat cagcgccatg caaccatcaa tcctgatgta    11640
caggcagact ttacagaact aactctgatt ggagcagtag attctggaat catggcacaa    11700
aactgcttgc ttgcagccga gtctatggga ttaggtggcg tatatattgg aggactaagg    11760
aatagcgcag ctcaagttga tgagctattg ggcttaccgg aaaatagcgc ggtgttgttt    11820
ggtatgtgct tagggcatcc cgatcaaaat cccgaagtaa agccacgcct acctgcacat    11880
gtggttgttc atgaaaatca ataccaagag ctaaatttag atgatattca gagctacgat    11940
caaactatgc aagcgtatta tgcgagccgt acaagcaatc aaaaactgag tacatggtcg    12000
caagaagtca ctgggaagct tgctggtgag tcgcgacctc atattctgcc gtacttgaac    12060
agtaaggggc tagcaaaacg ctaagcgatt taatctctaa ttattagtta aagttttata    12120
agcattttta tgtaacgaaa aataaaattgg ttcatattat tactgcactg tcacttacca    12180
tggaaagacc agacaagaag ttgccgacag tctgttgaat tggcctggtt aggcttaagt    12240
ctgggtccgc ttctttacaa atttggagaa tttctcttaa acgatatgta tattcttttc    12300
gttggaaaag atgtcttcca aaaaaaaaac cgatgaatta gtggaaccaa ggaaaaaaaa    12360
agaggtatcc ttgattaagg aacactgttt aaacagtgtg gtttccaaaa ccctgaaact    12420
gcattagtgt aatagaagac tagacacctc gatacaaata atggttactc aattcaaaac    12480
tgctccaact ggcaccgctg gcttgaacaa caataccagc cttccaactt ctgtaaataa    12540
cggcggtacg ccagtgccac cagtaccgtt acctttcggt atacctcctt tccccatgtt    12600
tccaatgccc ttcatgcctc caacggctac tatcacaaat cctcatcaag ctgacgcaag    12660
ccctaagaaa tgaataacaa tactgacagt actaaataat tgcctacttg gcttcacata    12720
cgttgcatac gtcgatatag ataataatga taatgacagc aggattatcg taatacgtaa    12780
tagttgaaaa tctcaaaaat gtgtgggtca ttacgtaaat aatgatagga atgggattct    12840
tctatttttc ctttttccat tctagcagcc gtcgggaaaa cgtggcatcc tctctttcgg    12900
gctcaattgg agtcacgctg ccgtgagcat cctctctttc catatctaac aactgagcac    12960
gtaaccaatg gaaagcatg agcttagcgt tgctccaaaa aagtattgga tggttaatac    13020
catttgtctg ttctcttctg actttgactc ctcaaaaaaa aaaatctac aatcaacaga    13080 tcgcttcaat tacgccctca caaaaacttt tttccttctt cttcgcccac gttaaatttt    13140
atccctcatg ttgtctaacg gatttctgca cttgatttat tataaaaaga caaagacata    13200
atacttctct atcaatttca gttattgttc ttccttgcgt tattcttctg ttcttctttt    13260
tcttttgtca tatataacca taaccaagta atacatattc aaaatgaaat ttggaaactt    13320
tttgcttaca taccaacccc cccaattttc tcaaacagaa gtaatgaaac gtttggttaa    13380
attaggtcgt atttctgagg agtgtggttt tgatactgta tggttactgg agcatcattt    13440
cacggagttt ggtttgcttg gtaaccctta tgtcgctgct gcatatttac ttggtgcaac    13500
caaaaaattg aatgtaggga ctgcggctat tgttcttccc accgctcatc cagtgcgcca    13560
acttgaagat gtgaatttat tggatcaaat gtcaaaagga cgatttcggt ttggtatttg    13620
tcgggggctt tacaataaag actttcgcgt atttggcacg gatatgaata acagtcgcgc    13680
```

-continued

```
tttaacggag tgctggtacg ggttgataaa aaatggcatg acagagggat atatggaagc    13740
tgataatgaa catatcaagt tccataaggt aaaagtaaac ccgacagcat atagtaaagg    13800
tggagcccct gtttatgtgg ttgctgaatc agcctcgaca actgaatggg ccgctcaatt    13860
tggtttaccg atgatattaa gttggattat aaatactaac gaaaagaaag cacagcttga    13920
gctttataac gaggtggctc aagaatatgg gcacgatatt cataatatcg accattgctt    13980
atcatatata acatctgtaa attatgactc aaataaagcg caagagattt gtcgggattt    14040
tctagggcat tggtatgatt cttatgtgaa tgccacgacc attttttgatg attcagacaa    14100 aacaagaggt tatgatttca ataaagggca gtggcgtgac tttgtattaa agggacatag    14160
agatactaat cgccgcattg attacagtta cgaaatcaat cccgtgggaa ccccgcagga    14220
atgcattgac ataattcaaa aagacattga tgccacggga atatcaaata tctgttgtgg    14280
gtttgaagcg aatggaacag tagacgaaat tattgcttcc atgaagctct tccagtctga    14340
tgtcatgccg tttcttaaag aaaaacaacg ttcgctatta tctagaatga aatttggatt    14400
gttcttcctt aacttcatca attcaacaac tgttcaagaa caaagtatag ttcgcatgca    14460
ggaaataaca gagtatgttg ataagttgaa ttttgaacag attttggtgt atgaaaatca    14520
tttttcaggt aatggtgttg tcggtgctcc tctgactgtt tctggttttt tgctcggttt    14580
aacagaaaaa attaaaattg gctcattgaa tcacatcatt acaactcatc atcctgtccg    14640
aatagcggag gaggcttgct tattggatca attaagcgaa gggagattta ttttagggtt    14700
tagtgattgt gaaaaaaaag atgaaatgcg tcttttttaat cgccctgttg aatatcaaca    14760
gcaactattt gaagagtgtt atgaaatcat taacgatgct ttaacaacag gctattgtaa    14820
tcccgataat gattttttata gtttccctaa aatatcggta aaccccccacg cttatacccca    14880 aggcgggcct cggagatatg tcacagcaac cagtcatcat attgttgagt gggcggctaa    14940
aaaaggcatt cctctcatct ttaagtggga tgactccaat gatgttagat atgaatatgc    15000
tgaaaggtat aaagccgttg ctgataaata tggtattgac ttatcagcga tagatcatca    15060
gttaatggta ttggttaact ataacgaaga tagtcacaaa gctaaacaag agacgcgtgc    15120
atttatccgt gattatgttc ttgaaatgta tcctaatgaa aatctcgaaa ataaacttga    15180
agagataatc acagaaaacg ctgtcggaga ttatacggaa tgtatagctg cggctaagct    15240
ggcaattgaa aagtgcggtg caaaaagtgt attgttatct tttgaaccaa tgaatgactt    15300
gatgcaccaa aaaaacgtaa tcaatattgt taatgataat attaaaaagt accacatgta    15360
ggttaattca aattaattga tatagttttt taatgagtat tgaatctgtt tagaaataat    15420
ggaatattat ttttatttat ttatttatat tattggtcgg ctcttttctt ctgaaggtca    15480
atgcaaaaat gatatgaagg aaataatgat ttctaaaatt ttacaacgta agatattttt    15540
acaaaagcct agctcatctt tccaattcgc cctatagtga gtcgtattac gcgcgctcac    15600
tggccgtcgt tttacaacgt cgtgactggg aaaaccctgg cgttacccaa cttaatcgcc    15660
ttgcagcaca tccccctttc gccagctggc gtaatagcga gaggcccgc accgatcgcc    15720 cttcccaaca gttgcgcagc ctgaatggcg aatggcgcga cgcgccctgt agcggcgcat    15780
taagcgcggc gggtgtggtg gttacgcgca gcgtgaccgc tacacttgcc agcgccctag    15840
cgcccgctcc tttcgctttc ttcccttcct ttctcgccac gttcgccggc tttccccgtc    15900
aagctctaaa tcgggggctc cctttagggt tccgatttag tgctttacgg cacctcgacc    15960
ccaaaaaact tgattagggt gatggttcac gtagtgggcc atcgccctga tagacggttt    16020
ttcgcccttt gacgttggag tccacgttct ttaatagtgg actcttgttc caaactggaa    16080
```

-continued

```
caacactcaa ccctatctcg gtctattctt ttgatttata agggattttg ccgatttcgg   16140
cctattggtt aaaaaatgag ctgatttaac aaaaatttaa cgcgaatttt aacaaaatat   16200
taacgtttac aatttcctga tgcggtattt tctccttacg catctgtgcg gtatttcaca   16260
ccgcataggg taataactga tataattaaa ttgaagctct aatttgtgag tttagtatac   16320
atgcatttac ttataataca gttttttagt tttgctggcc gcatcttctc aaatatgctt   16380
cccagcctgc ttttctgtaa cgttcaccct ctaccttagc atcccttccc tttgcaaata   16440
gtcctcttcc aacaataata atgtcagatc ctgtagagac cacatcatcc acggttctat   16500
actgttgacc caatgcgtct cccttgtcat ctaaacccac accgggtgtc ataatcaacc   16560
aatcgtaacc ttcatctctt ccacccatgt ctctttgagc aataaagccg ataacaaaat   16620
ctttgtcgct cttcgcaatg tcaacagtac ccttagtata ttctccagta gatagggagc   16680
ccttgcatga caattctgct aacatcaaaa ggcctctagg ttcctttgtt acttcttctg   16740
ccgcctgctt caaaccgcta acaatacctg ggcccaccac accgtgtgca ttcgtaatgt   16800
ctgcccattc tgctattctg tatacacccg cagagtactg caatttgact gtattaccaa   16860
tgtcagcaaa ttttctgtct tcgaagagta aaaaattgta cttggcggat aatgcctta    16920 gcggcttaac tgtgccctcc atggaaaaat cagtcaagat atccacatgt gttttagta    16980 aacaaatttt gggacctaat gcttcaacta actccagtaa ttccttggtg gtacgaacat   17040
ccaatgaagc acacaagttt gtttgctttt cgtgcatgat attaaatagc ttggcagcaa   17100
caggactagg atgagtagca gcacgttcct tatatgtagc tttcgacatg atttatcttc   17160
gtttcctgca ggtttttgtt ctgtgcagtt gggttaagaa tactgggcaa tttcatgttt   17220
cttcaacact acatatgcgt atatatacca atctaagtct gtgctccttc cttcgttctt   17280
ccttctgttc ggagattacc gaatcaaaaa aatttcaaag aaaccgaaat caaaaaaaag   17340
aataaaaaaa aaatgatgaa ttgaattgaa aagctgtggt atggtgcact ctcagtacaa   17400
tctgctctga tgccgcatag ttaagccagc cccgacaccc gccaacaccc gctgacgcgc   17460
cctgacgggc ttgtctgctc ccggcatccg cttacagaca agctgtgacc gtctccggga   17520
gctgcatgtg tcagaggttt tcaccgtcat caccgaaacg cgcga                   17565
```

<210> SEQ ID NO 8
<211> LENGTH: 685
<212> TYPE: PRT
<213> ORGANISM: Artificial
<220> FEATURE:
<223> OTHER INFORMATION: LuxA/LuxB Fusion

<400> SEQUENCE: 8

```
Met Lys Phe Gly Asn Phe Leu Leu Thr Tyr Gln Pro Pro Gln Phe Ser
1               5                   10                  15

Gln Thr Glu Val Met Lys Arg Leu Val Lys Leu Gly Arg Ile Ser Glu
            20                  25                  30

Glu Cys Gly Phe Asp Thr Val Trp Leu Leu Glu His His Phe Thr Glu
        35                  40                  45

Phe Gly Leu Leu Gly Asn Pro Tyr Val Ala Ala Ala Tyr Leu Leu Gly
    50                  55                  60

Ala Thr Lys Lys Leu Asn Val Gly Thr Ala Ala Ile Val Leu Pro Thr
65                  70                  75                  80

Ala His Pro Val Arg Gln Leu Glu Asp Val Asn Leu Leu Asp Gln Met
                85                  90                  95
```

-continued

```
Ser Lys Gly Arg Phe Arg Phe Gly Ile Cys Arg Gly Leu Tyr Asn Lys
            100                 105                 110

Asp Phe Arg Val Phe Gly Thr Asp Met Asn Asn Ser Arg Ala Leu Thr
            115                 120                 125

Glu Cys Trp Tyr Gly Leu Ile Lys Asn Gly Met Thr Glu Gly Tyr Met
    130                 135                 140

Glu Ala Asp Asn Glu His Ile Lys Phe His Lys Val Lys Val Asn Pro
145                 150                 155                 160

Thr Ala Tyr Ser Lys Gly Gly Ala Pro Val Tyr Val Val Ala Glu Ser
                165                 170                 175

Ala Ser Thr Thr Glu Trp Ala Ala Gln Phe Gly Leu Pro Met Ile Leu
            180                 185                 190

Ser Trp Ile Ile Asn Thr Asn Glu Lys Lys Ala Gln Leu Glu Leu Tyr
            195                 200                 205

Asn Glu Val Ala Gln Glu Tyr Gly His Asp Ile His Asn Ile Asp His
    210                 215                 220

Cys Leu Ser Tyr Ile Thr Ser Val Asn Tyr Asp Ser Asn Lys Ala Gln
225                 230                 235                 240

Glu Ile Cys Arg Asp Phe Leu Gly His Trp Tyr Asp Ser Tyr Val Asn
                245                 250                 255

Ala Thr Thr Ile Phe Asp Asp Ser Asp Lys Thr Arg Gly Tyr Asp Phe
            260                 265                 270

Asn Lys Gly Gln Trp Arg Asp Phe Val Leu Lys Gly His Arg Asp Thr
            275                 280                 285

Asn Arg Arg Ile Asp Tyr Ser Tyr Glu Ile Asn Pro Val Gly Thr Pro
    290                 295                 300

Gln Glu Cys Ile Asp Ile Ile Gln Lys Asp Ile Asp Ala Thr Gly Ile
305                 310                 315                 320

Ser Asn Ile Cys Cys Gly Phe Glu Ala Asn Gly Thr Val Asp Glu Ile
                325                 330                 335

Ile Ala Ser Met Lys Leu Phe Gln Ser Asp Val Met Pro Phe Leu Lys
            340                 345                 350

Glu Lys Gln Arg Ser Leu Leu Ser Arg Met Lys Phe Gly Leu Phe Phe
            355                 360                 365

Leu Asn Phe Ile Asn Ser Thr Thr Val Gln Glu Gln Ser Ile Val Arg
    370                 375                 380

Met Gln Glu Ile Thr Glu Tyr Val Asp Lys Leu Asn Phe Glu Gln Ile
385                 390                 395                 400

Leu Val Tyr Glu Asn His Phe Ser Gly Asn Gly Val Val Gly Ala Pro
                405                 410                 415

Leu Thr Val Ser Gly Phe Leu Leu Gly Leu Thr Glu Lys Ile Lys Ile
            420                 425                 430

Gly Ser Leu Asn His Ile Ile Thr Thr His His Pro Val Arg Ile Ala
            435                 440                 445

Glu Glu Ala Cys Leu Leu Asp Gln Leu Ser Glu Gly Arg Phe Ile Leu
    450                 455                 460

Gly Phe Ser Asp Cys Glu Lys Lys Asp Glu Met Arg Leu Phe Asn Arg
465                 470                 475                 480

Pro Val Glu Tyr Gln Gln Gln Leu Phe Glu Glu Cys Tyr Glu Ile Ile
                485                 490                 495

Asn Asp Ala Leu Thr Thr Gly Tyr Cys Asn Pro Asp Asn Asp Phe Tyr
            500                 505                 510

Ser Phe Pro Lys Ile Ser Val Asn Pro His Ala Tyr Thr Gln Gly Gly
```

-continued

```
              515                520                525
Pro Arg Arg Tyr Val Thr Ala Thr Ser His His Ile Val Glu Trp Ala
    530                535                540

Ala Lys Lys Gly Ile Pro Leu Ile Phe Lys Trp Asp Asp Ser Asn Asp
545                550                555                560

Val Arg Tyr Glu Tyr Ala Glu Arg Tyr Lys Ala Val Ala Asp Lys Tyr
              565                570                575

Gly Ile Asp Leu Ser Ala Ile Asp His Gln Leu Met Val Leu Val Asn
          580                585                590

Tyr Asn Glu Asp Ser His Lys Ala Lys Gln Glu Thr Arg Ala Phe Ile
          595                600                605

Arg Asp Tyr Val Leu Glu Met Tyr Pro Asn Glu Asn Leu Glu Asn Lys
    610                615                620

Leu Glu Glu Ile Ile Thr Glu Asn Ala Val Gly Asp Tyr Thr Glu Cys
625                630                635                640

Ile Ala Ala Ala Lys Leu Ala Ile Glu Lys Cys Gly Ala Lys Ser Val
              645                650                655

Leu Leu Ser Phe Glu Pro Met Asn Asp Leu Met His Gln Lys Asn Val
          660                665                670

Ile Asn Ile Val Asn Asp Asn Ile Lys Lys Tyr His Met
          675                680                685

<210> SEQ ID NO 9
<211> LENGTH: 560
<212> TYPE: DNA
<213> ORGANISM: Saccharomyces cerevisiae

<400> SEQUENCE: 9
ggggccgtat acttacatat agtagatgtc aagcgtaggc gcttccctg ccggctgtga      60 gggcgccata accaaggtat ctatagaccg ccaatcagca aactacctcc gtacattcat     120
gttgcaccca cacatttata cacccagacc gcgacaaatt acccataagg ttgtttgtga     180
cggcgtcgta caagagaacg tgggaactt ttaggctcac caaaaaagaa agaaaaaata      240
cgagttgctg acagaagcct caagaaaaaa aaaattcttc ttcgactatg ctggaggcag     300
agatgatcga gccggtagtt aactatatat agctaaattg gttccatcac cttcttttct     360
ggtgtcgctc cttctagtgc tatttctggc ttttcctatt ttttttttc cattttttctt    420 tctctctttc taatatataa attctcttgc attttctatt tttctctcta tctattctac     480
ttgtttattc ccttcaaggt ttttttttaa ggagtacttg tttttagaat atacggtcaa     540
cgaactataa ttaactaaac                                                 560

<210> SEQ ID NO 10
<211> LENGTH: 1000
<212> TYPE: DNA
<213> ORGANISM: Saccharomyces cerevisiae

<400> SEQUENCE: 10
aatgctagta ttttggagat taatctcagt acaaacaat attaaaaaga ggtgaattat       60
ttttcccccc ttatttttt tttgttagaa ttgatccaaa tgtaaataaa caatcacaag      120
gaaaaaaaaa aaaaaaaaaa aaatagccgc catgacccg gatcgtcggt tgtgatacgg      180
tcagggtagc gccctggtca aacttcagaa ctaaaaaaat aataaggaag aaaaaaatag     240
ctaatttttc cggcagaaag attttcgcta cccgaaagtt tttccggcaa gctaaatgga     300
aaaaggaaag attattgaaa gagaaagaaa gaaaaaaaaa aaatgtacac ccagacatcg     360
```

-continued

```
ggcttccaca atttcggctc tattgttttc catctctcgc aacggcggga ttcctctatg      420
gcgtgtgatg tctgtatctg ttacttaatc cagaaactgg cacttgaccc aactctgcca      480
cgtgggtcgt tttgccatcg acagattggg agattttcat agtagaattc agcatgatag      540
ctacgtaaat gtgttccgca ccgtcacaaa gtgttttcta ctgttctttc ttctttcgtt      600
cattcagttg agttgagtga gtgctttgtt caatggatct tagctaaaat gcatattttt      660
tctcttggta aatgaatgct tgtgatgtct tccaagtgat ttcctttcct tcccatatga      720
tgctaggtac ctttagtgtc ttcctaaaaa aaaaaaaagg ctcgccatca aaacgatatt      780
cgttggcttt ttttctgaa ttataaatac tctttggtaa cttttcattt ccaagaacct      840
cttttttcca gttatatcat ggtccccttt caaagttatt ctctactctt tttcatattc      900
attctttttc atcctttggt ttttattct taacttgttt attattctct cttgtttcta      960
tttacaagac accaatcaaa acaaataaaa catcatcaca                          1000
```

<210> SEQ ID NO 11
<211> LENGTH: 600
<212> TYPE: DNA
<213> ORGANISM: Saccharomyces cerevisiae

<400> SEQUENCE: 11

```
gtgtcgacgc tgcgggtata gaaagggttc tttactctat agtacctcct cgctcagcat       60
ctgcttcttc ccaaagatga acgcggcgtt atgtcactaa cgacgtgcac caacttgcgg      120
aaagtggaat cccgttccaa aactggcatc cactaattga tacatctaca caccgcacgc      180
cttttttctg aagcccactt tcgtggactt tgccatatgc aaaattcatg aagtgtgata      240
ccaagtcagc atacacctca ctagggtagt ttctttggtt gtattgatca tttggttcat      300
cgtggttcat taattttttt tctccattgc tttctggctt tgatcttact atcatttgga      360
tttttgtcga aggttgtaga attgtatgtg acaagtggca ccaagcatat ataaaaaaaa      420
aaagcattat cttcctacca gagttgattg ttaaaaacgt atttatagca aacgcaattg      480
taattaattc ttattttgta tcttttcttc ccttgtctca atcttttatt tttattttat      540
ttttcttttc ttagtttctt tcataacacc aagcaactaa tactataaca tacaataata      600
```

<210> SEQ ID NO 12
<211> LENGTH: 800
<212> TYPE: DNA
<213> ORGANISM: Saccharomyces cerevisiae

<400> SEQUENCE: 12

```
catgcgactg ggtgagcata tgttccgctg atgtgatgtg caagataaac aagcaaggca       60
gaaactaact tcttcttcat gtaataaaca caccccgcgt ttatttacct atctctaaac      120
ttcaacacct tatatcataa ctaatatttc ttgagataag cacactgcac ccataccttc      180
cttaaaaacg tagcttccag ttttttggtgg ttccggcttc cttcccgatt ccgcccgcta      240
aacgcatatt tttgttgcct ggtggcattt gcaaaatgca taacctatgc atttaaaaga      300
ttatgtatgc tcttctgact tttcgtgtga tgaggctcgt ggaaaaaatg aataatttat      360
gaatttgaga acaattttgt gttgttacgg tattttacta tggaataatc aatcaattga      420 ggatttttatg caaatatcgt ttgaatattt ttccgaccct ttgagtactt ttcttcataa      480
ttgcataata ttgtccgctg cccctttttc tgttagacgg tgtcttgatc tacttgctat      540
cgttcaacac caccttattt tctaactatt ttttttttag ctcatttgaa tcagcttatg      600
```

-continued

```
gtgatggcac attttttgcat aaacctagct gtcctcgttg aacataggaa aaaaaaatat    660
ataaacaagg ctctttcact ctccttgcaa tcagatttgg gtttgttccc tttatttca     720 tatttcttgt catattcctt tctcaattat tattttctac tcataacctc acgcaaaata    780
acacagtcaa atcaatcaaa                                                800

<210> SEQ ID NO 13
<211> LENGTH: 820
<212> TYPE: DNA
<213> ORGANISM: Saccharomyces cerevisiae

<400> SEQUENCE: 13
tccaactggc accgctggct tgaacaacaa taccagcctt ccaacttctg taaataacgg     60
cggtacgcca gtgccaccag taccgttacc tttcggtata cctcctttcc ccatgtttcc    120
aatgcccttc atgcctccaa cggctactat cacaaatcct catcaagctg acgcaagccc    180
taagaaatga ataacaatac tgacagtact aaataattgc ctacttggct tcacatacgt    240
tgcatacgtc gatatagata ataatgataa tgacagcagg attatcgtaa tacgtaatag    300
ttgaaaatct caaaaatgtg tgggtcatta cgtaaataat gataggaatg ggattcttct    360 attttttcctt tttccattct agcagccgtc gggaaaacgt ggcatcctct ctttcgggct    420
caattggagt cacgctgccg tgagcatcct ctctttccat atctaacaac tgagcacgta    480
accaatggaa aagcatgagc ttagcgttgc tccaaaaaag tattggatgg ttaataccat    540
ttgtctgttc tcttctgact ttgactcctc aaaaaaaaaa aatctacaat caacagatcg    600
cttcaattac gccctcacaa aaacttttt ccttcttctt cgcccacgtt aaattttatc    660
cctcatgttg tctaacggat ttctgcactt gatttattat aaaaagacaa agacataata    720
cttctctatc aatttcagtt attgttcttc cttgcgttat tcttctgttc ttctttttct    780
tttgtcatat ataaccataa ccaagtaata catattcaaa                          820

<210> SEQ ID NO 14
<211> LENGTH: 500
<212> TYPE: DNA
<213> ORGANISM: Saccharomyces cerevisiae

<400> SEQUENCE: 14
gagtaataat tattgcttcc atataatatt tttatatacc tcttattttt atgtattagt     60
taattaagta ttttttatcta tctgcttatc attttctttt catataggg gggttggtgt    120 tttcttgccc atcagattga tgtcctccaa ctcggcacta ttttacaaag ggttttttg    180 taagagaagg agaagacaga tactaaacca tacgttactc gaaacaaaaa aaaaaaaat    240 ggaaaaagct gctatcaaca aaagacggcc tcatcaaacc taaagaaacc atgtcagcgt    300
atgtatatac cttgtaattt acgtttcctt aaatcttctt tctactaacg ttttcattat    360
tctatactct atgaccaata aaaacagact gtactttcaa aatttaccca gtaggccagc    420
aaataaagaa aattatacca gattacttct gaaacacatt aatcccaaca acaagtatgc    480
cattaatccg tcgctacccc                                                500

<210> SEQ ID NO 15
<211> LENGTH: 401
<212> TYPE: DNA
<213> ORGANISM: Saccharomyces cerevisiae

<400> SEQUENCE: 15
aaaaagaatc atgattgaat gaagatatta ttttttttgaa ttatatttt taaattttat     60
```

```
ataaagacat ggttttctt ttcaactcaa ataaagattt ataagttact taaataacat      120
acattttata aggtattcta taaaaagagt attatgttat tgttaacctt tttgtctcca      180
attgtcgtca taacgatgag gtgttgcatt tttggaaacg agattgacat agagtcaaaa      240
tttgctaaat ttgatccctc ccatcgcaag ataatcttcc ctcaaggtta tcatgattat      300
caggatggcg aaaggatacg ctaaaaattc aataaaaaat tcaatataat tttcgtttcc      360
caagaactaa cttggaaggt tatacatggg tacataaatg c                          401
```

```
<210> SEQ ID NO 16
<211> LENGTH: 400
<212> TYPE: DNA
<213> ORGANISM: Saccharomyces cerevisiae

<400> SEQUENCE: 16 agtgcttta actaagaatt attagtcttt tctgcttatt ttttcatcat agtttagaac      60
actttatatt aacgaatagt ttatgaatct atttaggttt aaaaattgat acagtttat      120 aagttacttt ttcaaagact cgtgctgtct attgcataat gcactggaag gggaaaaaaa      180
aggtgcacac gcgtggcttt ttcttgaatt tgcagtttga aaaataacta catggatgat      240
aagaaaacat ggagtacagt cactttgaga accttcaatc agctggtaac gtcttcgtta      300
attggatact caaaaaagat ggatagcatg aatcacaaga tggaaggaaa tgcgggccac      360
gaccacagtg atatgcatat gggagatgga gatgatacct                           400
```

```
<210> SEQ ID NO 17
<211> LENGTH: 399
<212> TYPE: DNA
<213> ORGANISM: Saccharomyces cerevisiae

<400> SEQUENCE: 17
gcgatttaat ctctaattat tagttaaagt tttataagca tttttatgta acgaaaaata      60
aattggttca tattattact gcactgtcac ttaccatgga aagaccagac aagaagttgc      120
cgacagtctg ttgaattggc ctggttaggc ttaagtctgg gtccgcttct ttacaaattt      180
ggagaatttc tcttaaacga tatgtatatt cttttcgttg aaaagatgt cttccaaaaa      240 aaaaaccgat gaattagtgg aaccaaggaa aaaaaaagag gtatccttga ttaaggaaca      300
ctgtttaaac agtgtggttt ccaaaaccct gaaactgcat tagtgtaata gaagactaga      360
cacctcgata caaataatgg ttactcaatt caaaactgc                            399
```

```
<210> SEQ ID NO 18
<211> LENGTH: 200
<212> TYPE: DNA
<213> ORGANISM: Saccharomyces cerevisiae

<400> SEQUENCE: 18
gttaattcaa attaattgat atagttttt aatgagtatt gaatctgttt agaaataatg      60
gaatattatt tttatttatt tatttatatt attggtcggc tcttttcttc tgaaggtcaa      120
tgacaaaatg atatgaagga aataatgatt tctaaaattt tacaacgtaa gatattttta      180
caaaagccta gctcatcttt                                                 200
```

```
<210> SEQ ID NO 19
<211> LENGTH: 1000
<212> TYPE: DNA
<213> ORGANISM: Saccharomyces cerevisiae
```

<400> SEQUENCE: 19
cctttcttta ccaaatgaaa ggatttaata gtacctatga aacaatagtt cgaactttg      60 ccatttcccg gttttttg  ccagcttgta taaaagtgca ccttacccctt atattgggct      120 cttattgaat gccttccgaa gaactgacta ttcaaaaat agaaacaagt acgtcaataa      180
aaaattttgc aattctacga ataattattc ctgtttcttt aacctggtaa aaaaaagtac      240
aaacacttaa gcttttgaa acagctttat tttgcttcat taaatagcta ggataagaaa      300
tccctcatcc gaaaggtttt gtatctaact accctagaga acatttgtcc tgatcaggtt      360
catttggagt ttatattttt tagaagctca aagtttgttg gactcattac catggaagaa      420
aaaaagaaga tactacgaaa tattggtttc tcaggttaaa taagggacac catttttccta      480 ttaggctagt cgagcttagt tcttctaatt tcttcagatc ttctataatt tcctatcttc      540
tacctgatgt gtgcatgata tatctatgag ctcctgatat tgcttgtttt actttagctt      600
gcatgacttg caataatcta atcatatatg ttcccgatta atatactgtg cacaaattgc      660
aggacatata attttttccgt ggattatatc ttcgattaac gtccgcgggt ctcataaaaa      720
gcaaaccaac ttcgcaattc cctagaaata cctcaataga aagttatttg taatgagatt      780
agtaatgaga ttagcaatga gattagtaat gagattagta atgagattag taatgtgatt      840
agtaatgcat agcggtataa atggtagtac taataagtaa gatagtatac cagttataat      900
aaataggcgg cgatgcttca aaactaattt ttgacgtttt taagaataaa gcctttacca      960
gtggcataaa tcagtagaat tctaagcaaa caaagtcgat      1000

<210> SEQ ID NO 20
<211> LENGTH: 8297
<212> TYPE: DNA
<213> ORGANISM: Artificial
<220> FEATURE:
<223> OTHER INFORMATION: pRS426 Firefly-Luci-FBA1

<400> SEQUENCE: 20
gacgaaaggg cctcgtgata cgcctatttt tataggttaa tgtcatgata ataatggttt      60
cttagtatga tccaatatca aaggaaatga tagcattgaa ggatgagact aatccaattg      120
aggagtggca gcatatagaa cagctaaagg gtagtgctga aggaagcata cgatacccg      180 catggaatgg gataatatca caggaggtac tagactacct ttcatcctac ataaatagac      240
gcatataagt acgcatttaa gcataaacac gcactatgcc gttcttctca tgtatatata      300
tatacaggca acacgcagat ataggtgcga cgtgaacagt gagctgtatg tgcgcagctc      360
gcgttgcatt ttcggaagcg ctcgttttcg gaaacgcttt gaagttccta ttccgaagtt      420
cctattctct agaaagtata ggaacttcag agcgcttttg aaaaccaaaa gcgctctgaa      480
gacgcacttt caaaaaacca aaaacgcacc ggactgtaac gagctactaa aatattgcga      540
ataccgcttc cacaaacatt gctcaaaagt atctctttgc tatatatctc tgtgctatat      600
ccctatataa cctacccatc cacctttcgc tccttgaact tgcatctaaa ctcgacctct      660
acatttttta tgtttatctc tagtattact ctttagacaa aaaaattgta gtaagaacta      720
ttcatagagt gaatcgaaaa caatacgaaa atgtaaacat ttcctatacg tagtatatag      780
agacaaaata gaagaaaccg ttcataattt tctgaccaat gaagaatcat caacgctatc      840
actttctgtt cacaaagtat gcgcaatcca catcggtata gaatataatc ggggatgcct      900
ttatcttgaa aaaatgcacc cgcagcttcg ctagtaatca gtaaacgcgg gaagtggagt      960
caggcttttt ttatggaaga gaaaatagac accaaagtag ccttcttcta accttaacgg      1020

```
acctacagtg caaaaagtta tcaagagact gcattataga gcgcacaaag gagaaaaaaa    1080
gtaatctaag atgctttgtt agaaaaatag cgctctcggg atgcattttt gtagaacaaa    1140
aaagaagtat agattctttg ttggtaaaat agcgctctcg cgttgcattt ctgttctgta    1200
aaaatgcagc tcagattctt tgtttgaaaa attagcgctc tcgcgttgca tttttgtttt    1260
acaaaaatga agcacagatt cttcgttggt aaaatagcgc tttcgcgttg catttctgtt    1320
ctgtaaaaat gcagctcaga ttctttgttt gaaaaattag cgctctcgcg ttgcattttt    1380
gttctacaaa atgaagcaca gatgcttcgt tcaggtggca ctttttcgggg aaatgtgcgc    1440 ggaacccta tttgtttatt tttctaaata cattcaaata tgtatccgct catgagacaa    1500 taacctgat aaatgcttca ataatattga aaaaggaaga gtatgagtat tcaacatttc    1560
cgtgtcgccc ttattcctt ttttgcggca ttttgcttc ctgttttgc tcacccagaa      1620 acgctggtga agtaaaaga tgctgaagat cagttgggtg cacgagtggg ttacatcgaa    1680
ctggatctca acagcggtaa gatccttgag agttttcgcc ccgaagaacg ttttccaatg    1740
atgagcactt ttaaagttct gctatgtggc gcggtattat cccgtattga cgccgggcaa    1800
gagcaactcg gtcgccgcat acactattct cagaatgact tggttgagta ctcaccagtc    1860
acagaaaagc atcttacgga tggcatgaca gtaagagaat tatgcagtgc tgccataacc    1920
atgagtgata acactgcggc caacttactt ctgacaacga tcggaggacc gaaggagcta    1980
accgcttttt tgcacaacat ggggggatcat gtaactcgcc ttgatcgttg ggaaccggag    2040
ctgaatgaag ccataccaaa cgacgagcgt gacaccacga tgcctgtagc aatggcaaca    2100
acgttgcgca aactattaac tggcgaacta cttactctag cttcccggca acaattaata    2160
gactggatgg aggcggataa agttgcagga ccacttctgc gctcggccct tccggctggc    2220
tggtttattg ctgataaatc tggagccggt gagcgtgggt ctcgcggtat cattgcagca    2280
ctggggccag atggtaagcc ctcccgtatc gtagttatct acacgacggg gagtcaggca    2340
actatggatg aacgaaatag acagatcgct gagataggtg cctcactgat taagcattgg    2400
taactgtcag accaagttta ctcatatata ctttagattg atttaaaact tcatttttaa    2460
tttaaaagga tctaggtgaa gatcctttt gataatctca tgaccaaaat cccttaacgt      2520
gagttttcgt tccactgagc gtcagacccc gtagaaaaga tcaaaggatc ttcttgagat    2580
cctttttttc tgcgcgtaat ctgctgcttg caaacaaaaa aaccaccgct accagcggtg    2640
gtttgtttgc cggatcaaga gctaccaact cttttttccga aggtaactgg cttcagcaga    2700
gcgcagatac caaatactgt ccttctagtg tagccgtagt taggccacca cttcaagaac    2760
tctgtagcac cgcctacata cctcgctctg ctaatcctgt taccagtggc tgctgccagt    2820
ggcgataagt cgtgtcttac cgggttggac tcaagacgat agttaccgga taaggcgcag    2880
cggtcgggct gaacgggggg ttcgtgcaca gcccagct tggagcgaac gacctacacc      2940
gaactgagat acctacagcg tgagctatga aaagcgcca cgcttcccga agggagaaag      3000
gcggacaggt atccggtaag cggcagggtc ggaacaggag agcgcacgag ggagcttcca    3060
gggggaaacg cctggtatct ttatagtcct gtcgggtttc gccacctctg acttgagcgt    3120
cgatttttgt gatgctcgtc agggggcgg agcctatgga aaaacgccag caacgcggcc    3180
tttttacggt tcctggcctt ttgctggcct tttgctcaca tgttctttcc tgcgttatcc    3240
cctgattctg tggataaccg tattaccgcc tttgagtgag ctgataccgc tcgccgcagc    3300
cgaacgaccg agcgcagcga gtcagtgagc gaggaagcgg aagagcgccc aatacgcaaa    3360
```

-continued

```
ccgcctctcc ccgcgcgttg gccgattcat taatgcagct ggcacgacag gtttcccgac    3420
tggaaagcgg gcagtgagcg caacgcaatt aatgtgagtt acctcactca ttaggcaccc    3480
caggctttac actttatgct tccggctcct atgttgtgtg gaattgtgag cggataacaa    3540
tttcacacag gaaacagcta tgaccatgat tacgccaagc gcgcaattaa ccctcactaa    3600
agggaacaaa agctggagct ccaactggc accgctggct tgaacaacaa taccagcctt    3660
ccaacttctg taaataacgg cggtacgcca gtgccaccag taccgttacc tttcggtata    3720
cctcctttcc ccatgtttcc aatgcccttc atgcctccaa cggctactat cacaaatcct    3780
catcaagctg acgcaagccc taagaaatga ataacaatac tgacagtact aaataattgc    3840
ctacttggct tcacatacgt tgcatacgtc gatatagata ataatgataa tgacagcagg    3900
attatcgtaa tacgtaatag ttgaaaatct caaaaatgtg tgggtcatta cgtaaataat    3960
gataggaatg ggattcttct attttttcctt tttccattct agcagccgtc gggaaaacgt    4020
ggcatcctct ctttcgggct caattggagt cacgctgccg tgagcatcct ctctttccat    4080
atctaacaac tgagcacgta accaatggaa aagcatgagc ttagcgttgc tccaaaaaag    4140
tattggatgg ttaataccat ttgtctgttc tcttctgact ttgactcctc aaaaaaaaaa    4200
aatctacaat caacagatcg cttcaattac gccctcacaa aaacttttttt ccttcttctt    4260 cgcccacgtt aaattttatc cctcatgttg tctaacggat ttctgcactt gatttattat    4320
aaaaagacaa agacataata cttctctatc aatttcagtt attgttcttc cttgcgttat    4380
tcttctgttc ttcttttttct tttgtcatat ataaccataa ccaagtaata catattcaaa    4440
atggaagacg ccaaaaacat aaagaaaggc ccggcgccat tctatcctct tgaggatgga    4500
accgctggag agcaactgca taaggctatg aagagatacg ccctggttcc tggaacaatt    4560
gcttttacag atgcacatat cgaggtgaac atcacgtacg cggaatactt cgaaatgtcc    4620
gttcggttgg cagaagctat gaaacgatat gggctgaata caaatcacag aatcgtcgta    4680
tgcagtgaaa actctcttca attctttatg ccggtgttgg gcgcgttatt tatcggagtt    4740
gcagttgcgc ccgcgaacga catttataat gaacgtgaat tgctcaacag tatgaacatt    4800
tcgcagccta ccgtagtgtt tgtttccaaa aaggggttgc aaaaaatttt gaacgtgcaa    4860
aaaaaattac caataatcca gaaaattatt atcatggatt ctaaaacgga ttaccaggga    4920
tttcagtcga tgtacacgtt cgtcacatct catctacctc ccggttttaa tgaatacgat    4980
tttgtaccag agtcctttga tcgtgacaaa acaattgcac tgataatgaa ctcctctgga    5040
tctactgggt tacctaaggg tgtggccctt ccgcatagaa ctgcctgcgt cagattctcg    5100
catgccagag atcctatttt tggcaatcaa atcattccgg atactgcgat tttaagtgtt    5160
gttccattcc atcacggttt tggaatgttt actacactcg gatatttgat atgtggattt    5220
cgagtcgtct taatgtatag atttgaagaa gagctgtttt tacgatccct tcaggattac    5280
aaaattcaaa gtgcgttgct agtaccaacc ctattttcat tcttcgccaa aagcactctg    5340
attgacaaat acgatttatc taatttacac gaaattgctt ctggggggcgc acctctttcg    5400 aaagaagtcg gggaagcggt tgcaaaacgc ttccatcttc cagggatacg acaaggatat    5460
gggctcactg agactacatc agctattctg attacacccg agggggatga taaaccgggc    5520
gcggtcggta aagttgttcc attttttgaa gcgaaggttg tggatctgga taccgggaaa    5580
acgctgggcg ttaatcagag aggcgaatta tgtgtcagag gacctatgat tatgtccggt    5640
tatgtaaaca atccggaagc gaccaacgcc ttgattgaca aggatggatg gctacattct    5700
ggagacatag cttactggga cgaagacgaa cacttcttca tagttgaccg cttgaagtct    5760
```

-continued

```
ttaattaaat acaaaggata tcaggtggcc cccgctgaat tggaatcaat attgttacaa    5820
caccccaaca tcttcgacgc gggcgtggca ggtcttcccg acgatgacgc cggtgaactt    5880
cccgccgccg ttgttgtttt ggagcacgga aagacgatga cggaaaaaga gatcgtggat    5940
tacgtcgcca gtcaagtaac aaccgcgaaa aagttgcgcg gaggagttgt gtttgtggac    6000
gaagtaccga aaggtcttac cggaaaactc gacgcaagaa aaatcagaga gatcctcata    6060
aaggccaaga agggcggaaa gtccaaattg taagttaatt caaattaatt gatatagttt    6120
tttaatgagt attgaatctg tttagaaata atggaatatt atttttattt atttatttat    6180
attattggtc ggctcttttc ttctgaaggt caatgacaaa atgatatgaa ggaaataatg    6240
atttctaaaa ttttacaacg taagatattt ttacaaaagc ctagctcatc tttccaattc    6300
gccctatagt gagtcgtatt acgcgcgctc actggccgtc gttttacaac gtcgtgactg    6360
ggaaaaccct ggcgttaccc aacttaatcg ccttgcagca catccccctt tcgccagctg    6420
gcgtaatagc gaagaggccc gcaccgatcg cccttcccaa cagttgcgca gcctgaatgg    6480
cgaatggcgc gacgcgccct gtagcggcgc attaagcgcg gcgggtgtgg tggttacgcg    6540
cagcgtgacc gctacacttg ccagcgccct agcgcccgct cctttcgctt tcttcccttc    6600
ctttctcgcc acgttcgccg gctttccccg tcaagctcta aatcgggggc tccctttagg    6660
gttccgattt agtgctttac ggcacctcga ccccaaaaaa cttgattagg gtgatggttc    6720
acgtagtggg ccatcgccct gatagacggt ttttcgccct ttgacgttgg agtccacgtt    6780
ctttaatagt ggactcttgt tccaaactgg aacaacactc aaccctatct cggtctattc    6840
ttttgattta taggggattt tgccgatttc ggcctattgg ttaaaaaatg agctgattta    6900
acaaaaattt aacgcgaatt ttaacaaaat attaacgttt acaatttcct gatgcggtat    6960
tttctcctta cgcatctgtg cggtatttca caccgcatag ggtaataact gatataatta    7020
aattgaagct ctaatttgtg agtttagtat acatgcattt acttataata cagttttta    7080 gttttgctgg ccgcatcttc tcaaatatgc ttcccagcct gcttttctgt aacgttcacc    7140
ctctacctta gcatcccttc cctttgcaaa tagtcctctt ccaacaataa taatgtcaga    7200
tcctgtagag accacatcat ccacggttct atactgttga cccaatgcgt ctcccttgtc    7260
atctaaaccc acaccgggtg tcataatcaa ccaatcgtaa ccttcatctc ttccacccat    7320
gtctctttga gcaataaagc cgataacaaa atctttgtcg ctcttcgcaa tgtcaacagt    7380
acccttagta tattctccag tagataggga gcccttgcat gacaattctg ctaacatcaa    7440
aaggcctcta ggttcctttg ttacttcttc tgccgcctgc ttcaaaccgc taacaatacc    7500
tgggcccacc acaccgtgtg cattcgtaat gtctgcccat tctgctattc tgtatacacc    7560
cgcagagtac tgcaatttga ctgtattacc aatgtcagca aattttctgt cttcgaagag    7620
taaaaaattg tacttggcgg ataatgcctt tagcggctta actgtgccct ccatggaaaa    7680
atcagtcaag atatccacat gtgttttag taaacaaatt ttgggaccta atgcttcaac    7740
taactccagt aattccttgg tggtacgaac atccaatgaa gcacacaagt ttgtttgctt    7800
ttcgtgcatg atattaaata gcttggcagc aacaggacta ggatgagtag cagcacgttc    7860
cttatatgta gctttcgaca tgatttatct tcgtttcctg caggtttttg ttctgtgcag    7920
ttgggttaag aatactgggc aatttcatgt ttcttcaaca ctacatatgc gtatatatac    7980
caatctaagt ctgtgctcct tccttcgttc ttccttctgt tcggagatta ccgaatcaaa    8040
aaaatttcaa agaaaccgaa atcaaaaaaa agaataaaaa aaaaatgatg aattgaattg    8100
```

-continued

```
aaaagctgtg gtatggtgca ctctcagtac aatctgctct gatgccgcat agttaagcca        8160
gccccgacac ccgccaacac ccgctgacgc gccctgacgg gcttgtctgc tcccggcatc        8220
cgcttacaga caagctgtga ccgtctccgg gagctgcatg tgtcagaggt tttcaccgtc        8280
atcaccgaaa cgcgcga                                                      8297

<210> SEQ ID NO 21
<211> LENGTH: 14487
<212> TYPE: DNA
<213> ORGANISM: Artificial
<220> FEATURE:
<223> OTHER INFORMATION: pRS426_URA3_LuxCDE-frp

<400> SEQUENCE: 21
gacgaaaggg cctcgtgata cgcctatttt tataggttaa tgtcatgata ataatggttt         60
cttagtatga tccaatatca aaggaaatga tagcattgaa ggatgagact aatccaattg        120
aggagtggca gcatatagaa cagctaaagg gtagtgctga aggaagcata cgatacccccg       180 catggaatgg gataatatca caggaggtac tagactacct ttcatcctac ataaatagac        240
gcatataagt acgcatttaa gcataaacac gcactatgcc gttcttctca tgtatatata        300
tatacaggca cacgcagat ataggtgcga cgtgaacagt gagctgtatg tgcgcagctc        360
gcgttgcatt ttcggaagcg ctcgttttcg gaaacgcttt gaagttccta ttccgaagtt        420
cctattctct agaaagtata ggaacttcag agcgcttttg aaaaccaaaa gcgctctgaa        480
gacgcacttt caaaaaacca aaacgcacc ggactgtaac gagctactaa aatattgcga        540
ataccgcttc cacaaacatt gctcaaaagt atctctttgc tatatatctc tgtgctatat        600
ccctatataa cctacccatc cacctttcgc tccttgaact tgcatctaaa ctcgacctct        660 acattttta tgtttatctc tagtattact ctttagacaa aaaaattgta gtaagaacta        720
ttcatagagt gaatcgaaaa caatacgaaa atgtaaacat ttcctatacg tagtatatag        780
agacaaaata gaagaaaccg ttcataattt tctgaccaat gaagaatcat caacgctatc        840
actttctgtt cacaaagtat gcgcaatcca catcggtata gaatataatc ggggatgcct        900
ttatcttgaa aaaatgcacc cgcagcttcg ctagtaatca gtaaacgcgg gaagtggagt        960
caggcttttt ttatggaaga gaaaatagac accaaagtag ccttcttcta accttaacgg       1020
acctacagtg caaaaagtta tcaagagact gcattataga gcgcacaaag gagaaaaaaa       1080
gtaatctaag atgctttgtt agaaaaatag cgctctcggg atgcatttttt gtagaacaaa       1140 aaagaagtat agattctttg ttggtaaaat agcgctctcg cgttgcattt ctgttctgta       1200
aaaatgcagc tcagattctt tgtttgaaaa attagcgctc tcgcgttgca ttttttgtttt       1260 acaaaaatga agcacagatt cttcgttggt aaaatagcgc tttcgcgttg catttctgtt       1320
ctgtaaaaat gcagctcaga ttctttgttt gaaaaattag cgctctcgcg ttgcattttt       1380
gttctacaaa atgaagcaca gatgcttcgt tcaggtggca cttttcgggg aaatgtgcgc       1440 ggaacccta tttgtttatt tttctaaata cattcaaata tgtatccgct catgagacaa       1500
taaccctgat aaatgcttca ataatattga aaaggaaga gtatgagtat tcaacatttc       1560
cgtgtcgccc ttattccctt ttttgcggca ttttgccttc ctgttttttgc tcacccagaa       1620 acgctggtga aagtaaaaga tgctgaagat cagttgggtg cacgagtggg ttacatcgaa       1680
ctggatctca acagcggtaa gatccttgag agttttcgcc ccgaagaacg ttttccaatg       1740
atgagcactt ttaaagttct gctatgtggc gcggtattat cccgtattga cgccgggcaa       1800
gagcaactcg gtcgccgcat acactattct cagaatgact tggttgagta ctcaccagtc       1860
```

-continued

```
acagaaaagc atcttacgga tggcatgaca gtaagagaat tatgcagtgc tgccataacc    1920
atgagtgata acactgcggc caacttactt ctgacaacga tcggaggacc gaaggagcta    1980
accgcttttt tgcacaacat gggggatcat gtaactcgcc ttgatcgttg ggaaccggag    2040
ctgaatgaag ccataccaaa cgacgagcgt gacaccacga tgcctgtagc aatggcaaca    2100
acgttgcgca aactattaac tggcgaacta cttactctag cttcccggca acaattaata    2160
gactggatgg aggcggataa agttgcagga ccacttctgc gctcggccct tccggctggc    2220
tggtttattg ctgataaatc tggagccggt gagcgtgggt ctcgcggtat cattgcagca    2280
ctggggccag atggtaagcc ctcccgtatc gtagttatct acacgacggg gagtcaggca    2340
actatggatg aacgaaatag acagatcgct gagataggtg cctcactgat taagcattgg    2400
taactgtcag accaagttta ctcatatata ctttagattg atttaaaact tcattttttaa    2460 tttaaaagga tctaggtgaa gatccttttt gataatctca tgaccaaaat cccttaacgt    2520
gagttttcgt tccactgagc gtcagacccc gtagaaaaga tcaaaggatc ttcttgagat    2580 ccttttttc tgcgcgtaat ctgctgcttg caaacaaaaa aaccaccgct accagcggtg     2640
gtttgtttgc cggatcaaga gctaccaact cttttccga aggtaactgg cttcagcaga     2700
gcgcagatac caaatactgt ccttctagtg tagccgtagt taggccacca cttcaagaac    2760
tctgtagcac cgcctacata cctcgctctg ctaatcctgt taccagtggc tgctgccagt    2820
ggcgataagt cgtgtcttac cgggttggac tcaagacgat agttaccgga taaggcgcag    2880
cggtcgggct gaacggggggg ttcgtgcaca gcccagct tggagcgaac gacctacacc    2940
gaactgagat acctacagcg tgagctatga aaagcgcca cgcttcccga agggagaaag    3000
gcggacaggt atccggtaag cggcagggtc ggaacaggag agcgcacgag ggagcttcca    3060
gggggaaacg cctggtatct ttatagtcct gtcgggtttc gccacctctg acttgagcgt    3120
cgatttttgt gatgctcgtc aggggggcgg agcctatgga aaaacgccag caacgcggcc    3180
tttttacggt tcctggcctt ttgctggcct tttgctcaca tgttctttcc tgcgttatcc    3240
cctgattctg tggataaccg tattaccgcc tttgagtgag ctgataccgc tcgccgcagc    3300
cgaacgaccg agcgcagcga gtcagtgagc gaggaagcgg aagagcgccc aatacgcaaa    3360
ccgcctctcc ccgcgcgttg gccgattcat taatgcagct ggcacgacag gtttcccgac    3420
tggaaagcgg gcagtgagcg caacgcaatt aatgtgagtt acctcactca ttaggcaccc    3480
caggctttac actttatgct tccggctcct atgttgtgtg gaattgtgag cggataacaa    3540
tttcacacag gaaacagcta tgaccatgat tacgccaagc gcgcaattaa ccctcactaa    3600
agggaacaaa agctggagct ggggccgtat acttacatat agtagatgtc aagcgtaggc    3660
gcttcccctg ccggctgtga gggcgccata accaaggtat ctatagaccg ccaatcagca    3720
aactacctcc gtacattcat gttgcaccca cacatttata cacccagacc gcgacaaatt    3780
acccataagg ttgtttgtga cggcgtcgta caagagaacg tgggaacttt ttaggctcac    3840
caaaaaagaa agaaaaaata cgagttgctg acagaagcct caagaaaaaa aaaattcttc    3900
ttcgactatg ctggaggcag agatgatcga gccggtagtt aactatatat agctaaattg    3960
gttccatcac cttctttct ggtgtcgctc cttctagtgc tatttctggc ttttcctatt     4020 ttttttttc catttttctt tctctctttc taatatataa attctcttgc attttctatt    4080
tttctctcta tctattctac ttgtttattc ccttcaaggt ttttttttaa ggagtacttg    4140
tttttagaat atacggtcaa cgaactataa ttaactaaac atgactaaaa aaatttcatt    4200
```

-continued

```
cattattaac ggccaggttg aaattttttcc cgaaagtgat gatttagtgc aatccattaa    4260
ttttggtgat aatagtgttt acctgccaat attgaataat tctcatgtaa aaaacattat    4320
tgattataat gaaaataata aattacggtt gcataatatt gtcaatttc tctatacggt     4380 agggcaaaga tggaaaaatg aagaatattc aagacgcagg acatacattc gtgatttaaa    4440
aaaatatatg ggatattcag aagcaatggc caagttagag gccaactgga tatctatgat    4500
tttatgttct aaaggtggcc tttatgatgt tgtagaaaat gaacttggtt ctcgccatat    4560
catggatgaa tggctacctc aggatgaaag ttatattaag gcttttccga aaggtaagtc    4620
tatacatctg ttggcaggta atgttccatt atctgggatc atgtctatat tacgcgcaat    4680
tttaaccaag aatcagtgta ttataaaaac atcgtcaacc gatcccttta ccgctaatgc    4740
attagcgtta agctttatcg atgtagaccc taatcatccg ataacgcgct ctttgtctgt    4800
tgtatattgg ccacaccaag gtgatacatc actcgcaaaa gaaattatgc aacatatgga    4860
tgttattgtc gcttggggag gggaagatgc gattaattgg gctgtagaac atgcaccacc    4920
ctatgctgac gtgattaaat ttggctctaa aaagagtttt tgcattattg ataatccagt    4980
tgatttaacg tcagcagcta ccggtgcggc tcatgatatt tgttttttacg atcagcgcgc    5040 ttgttttttct gcccaaaaca tatattacat gggaaatcag tatgaggaat ttaagttagc    5100
gttgatagaa aaacttaatc tatatgcgca tatattacca aacgccaaaa aagattttga    5160
tgaaaaggcg gcctattctt tagtccaaaa agagagctta tttgctggat taaaagtaga    5220
ggtggatgtt catcaacgtt ggatgattat tgagtcaaat gcgggtgtgg aatttaatca    5280
accacttggc agatgtgtgt atcttcatca cgtcgataat attgagcaag tattgcctta    5340
tgttcaaaaa aataagacac aaaccatatc tattttttcct tgggaatccg catttaagta    5400
tcgagatgcg ttggcattaa gaggtgcgga aaggattgta gaagcaggaa tgaataatat    5460
atttcgagtt ggtggatctc atgacggaat gaggccgtta caacgattag tgacatatat    5520
ttctcatgag aggccatctc attatactgc taaggatgtt gcggttgaaa tagaacagac    5580
tcgattcctg gaagaagata agttccttgt atttgtcccg taagagtaat aattattgct    5640
tccatataat atttttatat acctcttatt tttatgtatt agttaattaa gtattttttat    5700 ctatctgctt atcattttct tttcatatag ggggggttgg tgtttcttg cccatcagat     5760 tgatgtcctc caactcggca ctattttaca aagggttttt ttgtaagaga aggagaagac    5820
agatactaaa ccatacgtta ctcgaaacaa aaaaaaaaaa aatggaaaaa gctgctatca    5880
acaaaagacg gcctcatcaa acctaaagaa accatgtcag cgtatgtata taccttgtaa    5940
tttacgtttc cttaaatctt ctttctacta acgttttcat tattctatac tctatgacca    6000
ataaaaacag actgtacttt caaaatttac ccagtaggcc agcaaataaa gaaaattata    6060
ccagattact tctgaaacac attaatccca acaacaagta tgccattaat ccgtcgctac    6120
cccaatgcta gtattttgga gattaatctc agtacaaaac aatattaaaa agaggtgaat    6180 tattttttccc cccttatttt tttttttgtta gaattgatcc aaatgtaaat aaacaatcac    6240
aaggaaaaaa aaaaaaaaaa aaaaaatagc cgccatgacc ccggatcgtc ggttgtgata    6300
cggtcagggt agcgccctgg tcaaacttca gaactaaaaa aataataagg aagaaaaaaa    6360
tagctaattt ttccggcaga aagattttcg ctacccgaaa gttttttccgg caagctaaat    6420 ggaaaaagga aagattattg aaagagaaag aaagaaaaaa aaaaaatgta cacccagaca    6480
tcgggcttcc acaatttcgg ctctattgtt ttccatctct cgcaacgcgc ggattcctct    6540
atggcgtgtg atgtctgtat ctgttactta atccagaaac tggcacttga cccaactctg    6600
```

-continued

```
ccacgtgggt cgttttgcca tcgacagatt gggagatttt catagtagaa ttcagcatga    6660
tagctacgta aatgtgttcc gcaccgtcac aaagtgtttt ctactgttct ttcttctttc    6720
gttcattcag ttgagttgag tgagtgcttt gttcaatgga tcttagctaa aatgcatatt    6780 tttttctcttg gtaaatgaat gcttgtgatg tcttccaagt gatttccttt ccttcccata    6840
tgatgctagg tacctttagt gtcttcctaa aaaaaaaaaa aggctcgcca tcaaaacgat    6900
attcgttggc ttttttttct gaattataaa tactctttgg taacttttca tttccaagaa    6960
cctctttttt ccagttatat catggtcccc tttcaaagtt attctctact cttttttcata   7020 ttcattcttt ttcatccttt ggtttttttat tcttaacttg tttattattc tctcttgttt   7080
ctatttacaa gacaccaatc aaaacaaata aaacatcatc acaatggaaa ataaatccaa    7140
atataaaacc atcgaccatg ttctttgtgt tgaaggaaat aaaaaaattc atgtttggga    7200
aacgctgcca gaagaaaaca gcccaaagag aaagaatacc attattattg cgtcgggttt    7260
tgcccgaagg atggatcatt ttgctggttt agcggaatat ttatcgcgga atgggtttca    7320
tgtgattcgc tatgattcac ttcaccacgt tgggttgagt tcaggacaa ttgatgaatt     7380 tacaatgtct ataggaaaac agagcctatt agccgtggtt gattggttaa atacacgaaa    7440
aataaataac cgtggtattt tggcttcaag cttatctgca cggatagttt atgcaagtct    7500
atctgaaatt aatgtttcat ttttaatcac cgcagtcggt gttgttaact taagatatac    7560
gcttgaaaga gctttaggat ttgattatct cagtttaccc attaatgaat tgccgaataa    7620
tttggatttt gaaggccata aattgggtgc tgaagtcttt gcgagagatt gccttgattt    7680
tggctgggaa gatttaactt ctacaatcaa tagcatgatg tatcttgata taccgtttat    7740
tgcttttact gcaaataacg acaattgggt aaagcaagat gaagttatca cattgttatc    7800
aaatattcgt agtaatcgat gcaagatata ttctttgcta gggagttcgc atgacttggg    7860
tgaaaactta gtggtcctgc gcaattttta tcaatcggtt acgaaggctg ctatcgcgat    7920
ggataatgat cgtctggata ttgatgttga tattattgaa ccatcattcg aacatctaac    7980
tattgcgaca gtcaatgaac gtcgaatgaa aattgagatt gaaaatcaag cgatttcgct    8040
gtcttaaaaa aagaatcatg attgaatgaa gatattattt ttttgaatta tattttttaa    8100
attttatata aagacatggt ttttcttttc aactcaaata aagatttata agttacttaa    8160
ataacataca ttttataagg tattctataa aaagagtatt atgttattgt taacctttttt   8220 gtctccaatt gtcgtcataa cgatgaggtg ttgcattttt ggaaacgaga ttgacataga    8280
gtcaaaattt gctaaatttg atccctccca tcgcaagata atcttccctc aaggttatca    8340
tgattatcag gatggcgaaa ggatacgcta aaaattcaat aaaaaattca atataatttt    8400
cgtttcccaa gaactaactt ggaaggttat acatgggtac ataaatgcgt gtcgacgctg    8460
cgggtataga aagggttctt tactctatag tacctcctcg ctcagcatct gcttcttccc    8520
aaagatgaac gcggcgttat gtcactaacg acgtgcacca acttgcggaa agtggaatcc    8580
cgttccaaaa ctggcatcca ctaattgata catctacaca ccgcacgcct ttttctgaa     8640 gcccactttc gtggactttg ccatatgcaa aattcatgaa gtgtgatacc aagtcagcat    8700
acacctcact agggtagttt ctttggttgt attgatcatt tggttcatcg tggttcatta    8760 atttttttttc tccattgctt tctggctttg atcttactat catttggatt tttgtcgaag    8820
gttgtagaat tgtatgtgac aagtggcacc aagcatatat aaaaaaaaaa agcattatct    8880
tcctaccaga gttgattgtt aaaaacgtat ttatagcaaa cgcaattgta attaattctt    8940
```

-continued

```
attttgtatc ttttcttccc ttgtctcaat ctttttatttt tattttattt ttcttttcttt    9000 agtttctttc ataacaccaa gcaactaata ctataacata caataataat gacttcatat    9060
gttgataaac aagagatcat agcaagctca gaaattgatg atttgatttt ttccagcgat    9120
ccattagctt ggtcttacga tgaacaggaa aaaatcagaa acaaatttgt tcttgatgca    9180
tttcgtaatc actataaaca ttgtcaagaa taccgtcact actgtcaggt acacaaagta    9240
gacgacaata ttacggaaat tgatgacata cctgtattcc caacatcagt ttttaagttt    9300
actcgcttat taacttctca ggagaacgag attgaaagtt ggtttaccag cagcggcacg    9360
agtggtttaa aaagtcaggt ggcgcgtaac agactaagta ttgagagact cttaggctct    9420
gtgagttatg gcatgaaata tgttggtagt tggtttgatc atcaaataga gttggtcaac    9480
ttagggccag atagatttaa tgctcataac atttggttta aatatgttat gagcttggta    9540
gaattattat atcccacgac atttaccgta atggaagaac gaatagattt tgttaagaca    9600
ttgaatagcc ttgagcgaat aaaaaatcaa ggaaaagata tttgtcttat cggctcacca    9660
tactttattt atttgctctg ccagtatatg aaagataaaa atatctcatt ttatggggat    9720
aaaaaccttt atatcataac gggggcggc tggaaaagtt atgaaaaaga gtccctaaaa    9780
cgcgatgatt tcaatcatct tttattcgac acgttcaacc tcaataatat tagtcaaatc    9840
cgcgatatat ttaatcaagt tgaactcaac acttgtttct ttgaggatga aatgcaacgt    9900
aaacgtgttc cgccgtgggt atatgcgcga gcacttgatc ctgaaacatt gaaacctgta    9960
cctgatggaa tgccgggttt gatgagttat atggatgcgt catcaacgag ttatccggca    10020
tttattgtta ccgatgatgt cgggataatg agcagagaat atggtcaata tcctggtgta    10080
cttgttgaga ttttacgtcg cgtcaatacg agggcacaga aagggtgtgc tttaagctta    10140
aaccaagcat ttaatagttg aagtgctttt aactaagaat tattagtctt ttctgcttat    10200
tttttcatca tagtttagaa cactttatat taacgaatag tttatgaatc tatttaggtt    10260
taaaaattga tacagtttta taagttactt tttcaaagac tcgtgctgtc tattgcataa    10320
tgcactggaa ggggaaaaaa aaggtgcaca cgcgtggctt tttcttgaat ttgcagtttg    10380
aaaaataact acatggatga taagaaaaca tggagtacag tcactttgag aaccttcaat    10440
cagctggtaa cgtcttcgtt aattggatac tcaaaaaaga tggatagcat gaatcacaag    10500
atggaaggaa atgcgggcca cgaccacagt gatatgcata tgggagatgg agatgatacc    10560
tcatgcgact gggtgagcat atgttccgct gatgtgatgt gcaagataaa caagcaaggc    10620
agaaactaac ttcttcttca tgtaataaac acaccccgcg tttatttacc tatctctaaa    10680
cttcaacacc ttatatcata actaatattt cttgagataa gcacactgca cccataacctt    10740 ccttaaaaac gtagcttcca gttttttggtg gttccggctt ccttcccgat tccgcccgct    10800
aaacgcatat ttttgttgcc tggtggcatt tgcaaaatgc ataacctatg catttaaaag    10860
attatgtatg ctcttctgac ttttcgtgtg atgaggctcg tggaaaaaat gaataatttta    10920 tgaatttgag aacaattttg tgttgttacg gtattttact atggaataat caatcaattg    10980
aggattttat gcaaatatcg tttgaatatt tttccgaccc tttgagtact tttcttcata    11040
attgcataat attgtccgct gccccttttt ctgttagacg gtgtcttgat ctacttgcta    11100
tcgttcaaca ccaccttatt ttctaactat ttttttttta gctcatttga atcagcttat    11160
ggtgatggca catttttgca taaacctagc tgtcctcgtt gaacatagga aaaaaaaata    11220
tataaacaag gctctttcac tctccttgca atcagatttg ggtttgttcc ctttattttc    11280
atatttcttg tcatattcct ttctcaatta ttattttcta ctcataacct cacgcaaaat    11340
```

```
aacacagtca aatcaatcaa aatgaacaat acgattgaaa ccattcttgc tcatcgctct  11400
atccgaaaat tcaccgcagt tcctattact gatgaacaaa gacaaaccat cattcaagca  11460
ggtttagctg cgtcttcttc tagtatgctt caagtcgtct caatcgttcg agtgactgac  11520
tctgaaaagc gtaacgaatt ggctcaattt gctggtaacc aagcttatgt tgaaagtgcg  11580
gctgagttct tagtgttttg tattgattat cagcgccatg caaccatcaa tcctgatgta  11640
caggcagact ttacagaact aactctgatt ggagcagtag attctggaat catggcacaa  11700
aactgcttgc ttgcagccga gtctatggga ttaggtggcg tatatattgg aggactaagg  11760
aatagcgcag ctcaagttga tgagctattg ggcttaccgg aaaatagcgc ggtgttgttt  11820
ggtatgtgct tagggcatcc cgatcaaaat cccgaagtaa agccacgcct acctgcacat  11880
gtggttgttc atgaaaatca ataccaagag ctaaatttag atgatattca gagctacgat  11940
caaactatgc aagcgtatta tgcgagccgt acaagcaatc aaaaactgag tacatggtcg  12000
caagaagtca ctgggaagct tgctggtgag tcgcgacctc atattctgcc gtacttgaac  12060
agtaaggggc tagcaaaacg ctaagcgatt taatctctaa ttattagtta aagttttata  12120
agcattttta tgtaacgaaa aataaaattgg ttcatattat tactgcactg tcacttacca  12180
tggaaagacc agacaagaag ttgccgacag tctgttgaat tggcctggtt aggcttaagt  12240
ctgggtccgc ttctttacaa atttggagaa tttctcttaa acgatatgta tattcttttc  12300
gttggaaaag atgtcttcca aaaaaaaaac cgatgaatta gtggaaccaa ggaaaaaaaa  12360
agaggtatcc ttgattaagg aacactgttt aaacagtgtg gtttccaaaa ccctgaaact  12420
gcattagtgt aatagaagac tagacacctc gatacaaata atggttactc aattcaaaac  12480
tgcccaattc gccctatagt gagtcgtatt acgcgcgctc actggccgtc gttttacaac  12540
gtcgtgactg ggaaaaccct ggcgttaccc aacttaatcg ccttgcagca catccccctt  12600
tcgccagctg gcgtaatagc gaagaggccc gcaccgatcg cccttcccaa cagttgcgca  12660
gcctgaatgg cgaatggcgc gacgcgccct gtagcggcgc attaagcgcg gcgggtgtgg  12720
tggttacgcg cagcgtgacc gctacacttg ccagcgccct agcgcccgct cctttcgctt  12780
tcttcccttc ctttctcgcc acgttcgccg gctttccccg tcaagctcta atcgggggc  12840 tccctttagg gttccgattt agtgctttac ggcacctcga ccccaaaaaa cttgattagg  12900
gtgatggttc acgtagtggg ccatcgccct gatagacggt ttttcgccct ttgacgttgg  12960
agtccacgtt ctttaatagt ggactcttgt tccaaactgg aacaacactc aaccctatct  13020
cggtctattc ttttgattta aagggattt tgccgatttc ggcctattgg ttaaaaaatg  13080
agctgattta acaaaaattt aacgcgaatt ttaacaaaat attaacgttt acaatttcct  13140
gatgcggtat tttctcctta cgcatctgtg cggtatttca caccgcatag ggtaataact  13200
gatataatta aattgaagct ctaatttgtg agtttagtat acatgcattt acttataata  13260
cagtttttta gttttgctgg ccgcatcttc tcaaatatgc ttcccagcct gcttttctgt  13320
aacgttcacc ctctacctta gcatcccttc cctttgcaaa tagtcctctt ccaacaataa  13380
taatgtcaga tcctgtagag accacatcat ccacggttct atactgttga cccaatgcgt  13440
ctcccttgtc atctaaaccc acaccgggtg tcataatcaa ccaatcgtaa ccttcatctc  13500
ttccacccat gtctctttga gcaataaagc cgataacaaa atctttgtcg ctcttcgcaa  13560
tgtcaacagt acccttagta tattctccag tagataggga gcccttgcat gacaattctg  13620
ctaacatcaa aaggcctcta ggttcctttg ttacttcttc tgccgcctgc ttcaaaccgc  13680
```

-continued

```
taacaatacc tgggcccacc acaccgtgtg cattcgtaat gtctgcccat tctgctattc    13740
tgtatacacc cgcagagtac tgcaatttga ctgtattacc aatgtcagca aattttctgt    13800
cttcgaagag taaaaaattg tacttggcgg ataatgcctt tagcggctta actgtgccct    13860
ccatggaaaa atcagtcaag atatccacat gtgtttttag taaacaaatt ttgggaccta    13920
atgcttcaac taactccagt aattccttgg tggtacgaac atccaatgaa gcacacaagt    13980
ttgtttgctt ttcgtgcatg atattaaata gcttggcagc aacaggacta ggatgagtag    14040
cagcacgttc cttatatgta gctttcgaca tgatttatct tcgtttcctg caggtttttg    14100
ttctgtgcag ttgggttaag aatactgggc aatttcatgt ttcttcaaca ctacatatgc    14160
gtatatatac caatctaagt ctgtgctcct tccttcgttc ttccttctgt tcggagatta    14220
ccgaatcaaa aaaatttcaa agaaaccgaa atcaaaaaaa agaataaaaa aaaaatgatg    14280
aattgaattg aaaagctgtg gtatggtgca ctctcagtac aatctgctct gatgccgcat    14340
agttaagcca gccccgacac ccgccaacac ccgctgacgc gccctgacgg gcttgtctgc    14400
tcccggcatc cgcttacaga caagctgtga ccgtctccgg gagctgcatg tgtcagaggt    14460
tttcaccgtc atcaccgaaa cgcgcga                                       14487
```

<210> SEQ ID NO 22
<211> LENGTH: 9390
<212> TYPE: DNA
<213> ORGANISM: Artificial
<220> FEATURE:
<223> OTHER INFORMATION: pRS426_LEU2_LuxAB

<400> SEQUENCE: 22

```
gacgaaaggg cctcgtgata cgcctatttt tataggttaa tgtcatgata ataatggttt       60
cttagtatga tccaatatca aaggaaatga tagcattgaa ggatgagact aatccaattg      120
aggagtggca gcatatagaa cagctaaagg gtagtgctga aggaagcata cgatacccccg     180 catggaatgg dataatatca caggaggtac tagactacct ttcatcctac ataaatagac      240
gcatataagt acgcatttaa gcataaacac gcactatgcc gttcttctca tgtatatata      300
tatacaggca acacgcagat ataggtgcga cgtgaacagt gagctgtatg tgcgcagctc      360
gcgttgcatt ttcggaagcg ctcgttttcg gaaacgcttt gaagttccta ttccgaagtt      420
cctattctct agaaagtata ggaacttcag agcgcttttg aaaaccaaaa gcgctctgaa      480
gacgcacttt caaaaaacca aaaacgcacc ggactgtaac gagctactaa aatattgcga      540
ataccgcttc cacaaacatt gctcaaaagt atctctttgc tatatatctc tgtgctatat      600
ccctatataa cctacccatc cacctttcgc tccttgaact tgcatctaaa ctcgacctct      660
acatttttta tgtttatctc tagtattact ctttagacaa aaaaattgta gtaagaacta      720
ttcatagagt gaatcgaaaa caatacgaaa atgtaaacat ttcctatacg tagtatatag      780
agacaaaata gaagaaaccg ttcataattt tctgaccaat gaagaatcat caacgctatc      840
actttctgtt cacaaagtat gcgcaatcca catcggtata gaatataatc ggggatgcct      900
ttatcttgaa aaaatgcacc cgcagcttcg ctagtaatca gtaaacgcgg gaagtggagt      960 caggctttttt ttatggaaga gaaaatagac accaaagtag ccttcttcta accttaacgg     1020
acctacagtg caaaaagtta tcaagagact gcattataga gcgcacaaag gagaaaaaaa     1080
gtaatctaag atgctttgtt agaaaaatag cgctctcggg atgcatttt gtagaacaaa      1140 aaagaagtat agattctttg ttggtaaaat agcgctctcg cgttgcattt ctgttctgta     1200
aaaatgcagc tcagattctt tgtttgaaaa attagcgctc tcgcgttgca ttttttgtttt    1260
```

-continued

```
acaaaaatga agcacagatt cttcgttggt aaaatagcgc tttcgcgttg catttctgtt    1320
ctgtaaaaat gcagctcaga ttctttgttt gaaaaattag cgctctcgcg ttgcattttt    1380
gttctacaaa atgaagcaca gatgcttcgt tcaggtggca cttttcgggg aaatgtgcgc    1440 ggaacccta tttgtttatt tttctaaata cattcaaata tgtatccgct catgagacaa     1500
taaccctgat aaatgcttca ataatattga aaaggaaga gtatgagtat tcaacatttc     1560
cgtgtcgccc ttattccctt ttttgcggca ttttgccttc ctgttttgc tcacccagaa     1620 acgctggtga agtaaaaga tgctgaagat cagttgggtg cacgagtggg ttacatcgaa     1680
ctggatctca acagcggtaa gatccttgag agttttcgcc ccgaagaacg ttttccaatg     1740
atgagcactt ttaaagttct gctatgtggc gcggtattat cccgtattga cgccgggcaa     1800
gagcaactcg gtcgccgcat acactattct cagaatgact tggttgagta ctcaccagtc     1860
acagaaaagc atcttacgga tggcatgaca gtaagagaat tatgcagtgc tgccataacc     1920
atgagtgata acactgcggc caacttactt ctgacaacga tcggaggacc gaaggagcta     1980 accgctttt tgcacaacat gggggatcat gtaactcgcc ttgatcgttg ggaaccggag      2040
ctgaatgaag ccataccaaa cgacgagcgt gacaccacga tgcctgtagc aatggcaaca     2100
acgttgcgca aactattaac tggcgaacta cttactctag cttcccggca acaattaata     2160
gactggatgg aggcggataa agttgcagga ccacttctgc gctcggccct tccggctggc     2220
tggtttattg ctgataaatc tggagccggt gagcgtgggt ctcgcggtat cattgcagca     2280
ctggggccag atggtaagcc ctcccgtatc gtagttatct acacgacggg gagtcaggca     2340
actatggatg aacgaaatag acagatcgct gagataggtg cctcactgat taagcattgg     2400
taactgtcag accaagttta ctcatatata ctttagattg atttaaaact tcatttttaa     2460
tttaaaagga tctaggtgaa gatcctttt gataatctca tgaccaaaat cccttaacgt      2520
gagttttcgt tccactgagc gtcagacccc gtagaaaaga tcaaaggatc ttcttgagat     2580
cctttttttc tgcgcgtaat ctgctgcttg caaacaaaaa aaccaccgct accagcggtg     2640
gtttgtttgc cggatcaaga gctaccaact ctttttccga aggtaactgg cttcagcaga     2700
gcgcagatac caaatactgt ccttctagtg tagccgtagt taggccacca cttcaagaac     2760
tctgtagcac cgcctacata cctcgctctg ctaatcctgt taccagtggc tgctgccagt     2820
ggcgataagt cgtgtcttac cgggttggac tcaagacgat agttaccgga taaggcgcag     2880
cggtcgggct gaacggggg ttcgtgcaca gcccagct tggagcgaac gacctacacc       2940
gaactgagat acctacagcg tgagctatga aaagcgcca cgcttcccga agggagaaag     3000
gcggacaggt atccggtaag cggcagggtc ggaacaggag agcgcacgag ggagcttcca     3060
gggggaaacg cctggtatct ttatagtcct gtcgggtttc gccacctctg acttgagcgt     3120 cgattttgt gatgctcgtc aggggggcgg agcctatgga aaaacgccag caacgcggcc      3180
tttttacggt tcctggcctt ttgctggcct tttgctcaca tgttctttcc tgcgttatcc     3240
cctgattctg tggataaccg tattaccgcc tttgagtgag ctgataccgc tcgccgcagc     3300
cgaacgaccg agcgcagcga gtcagtgagc gaggaagcgg aagagcgccc aatacgcaaa     3360
ccgcctctcc ccgcgcgttg gccgattcat taatgcagct ggcacgacag gtttcccgac     3420
tggaaagcgg gcagtgagcg caacgcaatt aatgtgagtt acctcactca ttaggcaccc     3480
caggctttac actttatgct tccggctcct atgttgtgtg gaattgtgag cggataacaa     3540
tttcacacag gaaacagcta tgaccatgat tacgccaagc gcgcaattaa ccctcactaa     3600
```

-continued

```
agggaacaaa agctggagct tccaactggc accgctggct tgaacaacaa taccagcctt    3660
ccaacttctg taaataacgg cggtacgcca gtgccaccag taccgttacc tttcggtata    3720
cctcctttcc ccatgtttcc aatgcccttc atgcctccaa cggctactat cacaaatcct    3780
catcaagctg acgcaagccc taagaaatga ataacaatac tgcacagtact aaataattgc    3840 ctacttggct tcacatacgt tgcatacgtc gatatagata ataatgataa tgacagcagg    3900
attatcgtaa tacgtaatag ttgaaaatct caaaaatgtg tgggtcatta cgtaaataat    3960
gataggaatg ggattcttct attttttcctt tttccattct agcagccgtc gggaaaacgt    4020
ggcatcctct ctttcgggct caattggagt cacgctgccg tgagcatcct ctctttccat    4080
atctaacaac tgagcacgta accaatggaa aagcatgagc ttagcgttgc tccaaaaaag    4140
tattggatgg ttaataccat ttgtctgttc tcttctgact ttgactcctc aaaaaaaaaa    4200
aatctacaat caacagatcg cttcaattac gccctcacaa aaactttttt ccttcttctt    4260
cgcccacgtt aaattttatc cctcatgttg tctaacggat ttctgcactt gatttattat    4320
aaaaagacaa agacataata cttctctatc aatttcagtt attgttcttc cttgcgttat    4380
tcttctgttc ttcttttct tttgtcatat ataaccataa ccaagtaata catattcaaa    4440
atgaaatttg gaaacttttt gcttacatac caacccccccc aattttctca aacagaagta    4500
atgaaacgtt tggttaaatt aggtcgtatt tctgaggagt gtggttttga tactgtatgg    4560
ttactggagc atcatttcac ggagtttggt ttgcttggta accttatgt cgctgctgca    4620 tatttacttg gtgcaaccaa aaaattgaat gtagggactg cggctattgt tcttcccacc    4680
gctcatccag tgcgccaact tgaagatgtg aatttattgg atcaaatgtc aaaaggacga    4740
tttcggtttg gtatttgtcg ggggctttac aataaagact ttcgcgtatt tggcacggat    4800
atgaataaca gtcgcgcttt aacggagtgc tggtacgggt tgataaaaaa tggcatgaca    4860
gagggatata tggaagctga taatgaacat atcaagttcc ataaggtaaa agtaaacccg    4920
acagcatata gtaaaggtgg agccctgtt tatgtggttg ctgaatcagc ctcgacaact    4980
gaatgggccg ctcaatttgg tttaccgatg atattaagtt ggattataaa tactaacgaa    5040
aagaaagcac agcttgagct ttataacgag gtggctcaag aatatgggca cgatattcat    5100
aatatcgacc attgcttatc atatataaca tctgtaaatt atgactcaaa taaagcgcaa    5160
gagatttgtc gggattttct agggcattgg tatgattctt atgtgaatgc cacgaccatt    5220
tttgatgatt cagacaaaac aagaggttat gatttcaata aagggcagtg gcgtgacttt    5280
gtattaaagg gacatagaga tactaatcgc cgcattgatt acagttacga aatcaatccc    5340
gtgggaaccc cgcaggaatg cattgacata attcaaaaag acattgatgc cacgggaata    5400
tcaaatatct gttgtgggtt tgaagcgaat ggaacagtag acgaaattat tgcttccatg    5460
aagctcttcc agtctgatgt catgccgttt cttaaagaaa acaacgttc gctattatct    5520 agaatgaaat ttggattgtt cttccttaac ttcatcaatt caacaactgt tcaagaacaa    5580
agtatagttc gcatgcagga aataacagag tatgttgata agttgaattt tgaacagatt    5640
ttggtgtatg aaaatcattt ttcaggtaat ggtgttgtcg gtgctcctct gactgtttct    5700 ggtttttttgc tcggtttaac agaaaaaatt aaaattggct cattgaatca catcattaca    5760
actcatcatc ctgtccgaat agcggaggag gcttgcttat tggatcaatt aagcgaaggg    5820
agatttattt tagggtttag tgattgtgaa aaaaagatg aaatgcgtct ttttaatcgc    5880
cctgttgaat atcaacagca actatttgaa gagtgttatg aaatcattaa cgatgcttta    5940
acaacaggct attgtaatcc cgataatgat ttttatagtt tccctaaaat atcggtaaac    6000
```

-continued

```
ccccacgctt atacccaagg cgggcctcgg agatatgtca cagcaaccag tcatcatatt    6060
gttgagtggg cggctaaaaa aggcattcct ctcatcttta agtgggatga ctccaatgat    6120
gttagatatg aatatgctga aaggtataaa gccgttgctg ataaatatgg tattgactta    6180
tcagcgatag atcatcagtt aatggtattg gttaactata acgaagatag tcacaaagct    6240
aaacaagaga cgcgtgcatt tatccgtgat tatgttcttg aaatgtatcc taatgaaaat    6300
ctcgaaaata aacttgaaga gataatcaca gaaaacgctg tcggagatta tacggaatgt    6360
atagctgcgg ctaagctggc aattgaaaag tgcggtgcaa aaagtgtatt gttatctttt    6420
gaaccaatga atgacttgat gcaccaaaaa aacgtaatca atattgttaa tgataatatt    6480
aaaaagtacc acatgtaggt taattcaaat taattgatat agtttttttaa tgagtattga    6540 atctgtttag aaataatgga atattatttt tattttattta tttatattat tggtcggctc    6600
ttttcttctg aaggtcaatg acaaaatgat atgaaggaaa taatgatttc taaaattttta    6660 caacgtaaga tattttttaca aaagcctagc tcatctttcc aattcgccct atagtgagtc    6720
gtattacgcg cgctcactgg ccgtcgtttt acaacgtcgt gactgggaaa accctggcgt    6780
tacccaactt aatcgccttg cagcacatcc cccttttcgcc agctggcgta atagcgaaga    6840
ggcccgcacc gatcgccctt cccaacagtt gcgcagcctg aatggcgaat ggcgcgacgc    6900
gccctgtagc ggcgcattaa gcgcggcggg tgtggtggtt acgcgcagcg tgaccgctac    6960
acttgccagc gccctagcgc ccgctccttt cgctttcttc ccttcctttc tcgccacgtt    7020
cgccggcttt ccccgtcaag ctctaaatcg ggggctccct ttagggttcc gatttagtgc    7080
tttacggcac ctcgacccca aaaaacttga ttagggtgat ggttcacgta gtgggccatc    7140
gccctgatag acggttttttc gcccttttgac gttggagtcc acgttcttta atagtggact    7200
cttgttccaa actggaacaa cactcaaccc tatctcggtc tattcttttg atttataagg    7260
gattttgccg atttcggcct attggttaaa aaatgagctg atttaacaaa aatttaacgc    7320
gaattttaac aaaatattaa cgtttacaat ttcctgatgc ggtattttct ccttacgcat    7380
ctgtgcggta tttcacaccg catagcgaat ttcttatgat ttatgatttt tattattaaa    7440
taagttataa aaaaaataag tgtatacaaa ttttaaagtg actcttaggt tttaaaacga    7500
aaattcttat tcttgagtaa ctctttcctg taggtcaggt tgctttctca ggtatagcat    7560
gaggtcgctc ttattgacca cacctctacc ggccggtcga aattccccta ccctatgaac    7620
atattccatt ttgtaatttc gtgtcgtttc tattatgaat ttcatttata aagtttatgt    7680
acaaatatca taaaaaaaga gaatcttttt aagcaaggat tttcttaact tcttcggcga    7740
cagcatcacc gacttcggtg gtactgttgg aaccacctaa atcaccagtt ctgatacctg    7800
catccaaaac cttttttaact gcatcttcaa tggccttacc ttcttcaggc aagttcaatg    7860
acaatttcaa catcattgca gcagacaaga tagtggcgat agggttgacc ttattctttg    7920
gcaaatctgg agcagaaccg tggcatggtt cgtacaaacc aaatgcggtg ttcttgtctg    7980
gcaaagaggc caaggacgca gatggcaaca aacccaagga acctgggata acggaggctt    8040
catcggagat gatatcacca aacatgttgc tggtgattat aataccattt aggtgggttg    8100
ggttcttaac taggatcatg gcggcagaat caatcaattg atgttgaacc ttcaatgtag    8160
gaaattcgtt cttgatggtt tcctccacag ttttttctcca taatcttgaa gaggccaaaa    8220
cattagcttt atccaaggac caaataggca atgtggctc atgttgtagg gccatgaaag    8280
cggccattct tgtgattctt tgcacttctg gaacggtgta ttgttcacta tcccaagcga    8340
```

-continued

```
caccatcacc atcgtcttcc tttctcttac caaagtaaat acctcccact aattctctga  8400
caacaacgaa gtcagtacct ttagcaaatt gtggcttgat tggagataag tctaaaagag  8460
agtcggatgc aaagttacat ggtcttaagt tggcgtacaa ttgaagttct ttacggattt  8520
ttagtaaacc ttgttcaggt ctaacactac ctgtacccca tttaggacca cccacagcac  8580
ctaacaaaac ggcatcagcc ttcttggagg cttccagcgc ctcatctgga agtgggacac  8640
ctgtagcttc gatagcagca ccaccaatta aatgattttc gaaatcgaac ttgacattgg  8700
aacgaacatc agaaatagct ttaagaacct taatggcttc ggctgtgatt tcttgaccaa  8760
cgtggtcacc tggcaaaacg acgatcttct taggggcaga cattagaatg gtatatcctt  8820
gaaatatata tatatattgc tgaaatgtaa aaggtaagaa aagttagaaa gtaagacgat  8880
tgctaaccac ctattggaaa aaacaatagg tccttaaata atattgtcaa cttcaagtat  8940
tgtgatgcaa gcatttagtc atgaacgctt ctctattcta tatgaaaagc cggttccggc  9000
gctctcacct ttccttttc tcccaatttt tcagttgaaa aaggtatatg cgtcaggcga  9060
cctctgaaat taacaaaaaa tttccagtca tcgaatttga ttctgtgcga tagcgcccct  9120
gtgtgttctc gttatgttga ggaaaaaaat aatggttgct aagagattcg aactcttgca  9180
tcttacgata cctgagtatt cccacagttt gcactctcag tacaatctgc tctgatgccg  9240
catagttaag ccagccccga cacccgccaa cacccgctga cgcgccctga cgggcttgtc  9300
tgctcccggc atccgcttac agacaagctg tgaccgtctc cgggagctgc atgtgtcaga  9360
ggttttcacc gtcatcaccg aaacgcgcga                                   9390
```